US012559791B2

(12) United States Patent
Kühnemund

(10) Patent No.: US 12,559,791 B2
(45) Date of Patent: Feb. 24, 2026

(54) METHODS AND COMPOSITIONS FOR IN SITU ANALYSIS OF V(D)J SEQUENCES

(71) Applicant: 10x Genomics, Inc., Pleasanton, CA (US)

(72) Inventor: Malte Kühnemund, Stockholm (SE)

(73) Assignee: 10X GENOMICS, INC., Pleasanton, CA (US)

( * ) Notice: Subject to any disclaimer, the term of this patent is extended or adjusted under 35 U.S.C. 154(b) by 229 days.

(21) Appl. No.: 18/313,256

(22) Filed: May 5, 2023

(65) Prior Publication Data

US 2024/0026427 A1      Jan. 25, 2024

Related U.S. Application Data

(60) Provisional application No. 63/339,390, filed on May 6, 2022.

(51) Int. Cl.
*C12Q 1/6841* (2018.01)
*C12Q 1/682* (2018.01)
*C12Q 1/6876* (2018.01)

(52) U.S. Cl.
CPC ........... *C12Q 1/6841* (2013.01); *C12Q 1/682* (2013.01); *C12Q 1/6876* (2013.01)

(58) Field of Classification Search
CPC ...... C12Q 1/68; C12Q 1/6841; C12Q 1/6882; C12Q 2531/125
See application file for complete search history.

(56) References Cited

U.S. PATENT DOCUMENTS

| | | | |
|---|---|---|---|
| 4,318,846 A | 3/1982 | Khanna et al. | |
| 4,757,141 A | 7/1988 | Fung et al. | |
| 4,849,336 A | 7/1989 | Miyoshi et al. | |
| 5,066,580 A | 11/1991 | Lee | |
| 5,091,519 A | 2/1992 | Cruickshank | |
| 5,151,507 A | 9/1992 | Hobbs et al. | |
| 5,188,934 A | 2/1993 | Menchen | |
| 5,198,537 A | 3/1993 | Huber et al. | |
| 5,344,757 A | 9/1994 | Holtke et al. | |
| 5,354,657 A | 10/1994 | Boehringer et al. | |
| 5,366,860 A | 11/1994 | Bergot et al. | |
| 5,635,352 A | 6/1997 | Urdea et al. | |
| 5,688,648 A | 11/1997 | Mathies | |
| 5,695,940 A | 12/1997 | Drmanac et al. | |
| 5,702,888 A | 12/1997 | Holtke et al. | |
| 5,800,996 A | 9/1998 | Lee et al. | |
| 5,847,162 A | 12/1998 | Lee et al. | |
| 5,919,626 A | 7/1999 | Shi et al. | |
| 5,990,479 A | 11/1999 | Weiss et al. | |
| 6,207,392 B1 | 3/2001 | Weiss et al. | |
| 6,251,303 B1 | 6/2001 | Bawendi et al. | |
| 6,306,597 B1 | 10/2001 | Macevicz | |
| 6,319,426 B1 | 11/2001 | Bawendi et al. | |
| 6,322,901 B1 | 11/2001 | Bawendi et al. | |
| 6,391,937 B1 | 5/2002 | Beuhler et al. | |
| 6,423,551 B1 | 7/2002 | Weiss et al. | |

| | | | |
|---|---|---|---|
| 6,426,513 B1 | 7/2002 | Bawendi et al. | |
| 6,444,143 B2 | 9/2002 | Bawendi et al. | |
| 6,534,266 B1 | 3/2003 | Singer | |
| 6,576,291 B2 | 6/2003 | Bawendi et al. | |
| 7,255,994 B2 | 8/2007 | Lao | |
| 7,345,159 B2 | 3/2008 | Ju et al. | |
| 7,473,767 B2 | 1/2009 | Dimitrov | |
| 7,534,991 B2 | 5/2009 | Miller et al. | |
| 7,544,794 B1 | 6/2009 | Benner | |
| 7,555,155 B2 | 6/2009 | Levenson et al. | |
| 7,566,537 B2 | 7/2009 | Balasubramanian et al. | |
| 7,655,898 B2 | 2/2010 | Miller | |
| 7,893,227 B2 | 2/2011 | Wu et al. | |
| 7,910,304 B2 | 3/2011 | Drmanac | |
| 7,941,279 B2 | 5/2011 | Hwang et al. | |
| 7,989,166 B2 | 8/2011 | Koch et al. | |
| 8,124,751 B2 | 2/2012 | Pierce et al. | |
| 8,133,672 B2 | 3/2012 | Bjornson et al. | |
| 8,199,999 B2 | 6/2012 | Hoyt et al. | |
| 8,257,954 B2 | 9/2012 | Clark et al. | |
| 8,268,554 B2 | 9/2012 | Schallmeiner | |
| 8,330,087 B2 | 12/2012 | Domenicali | |
| 8,343,746 B2 | 1/2013 | Rank et al. | |
| 8,415,102 B2 | 4/2013 | Geiss et al. | |
| 8,431,691 B2 | 4/2013 | McKernan et al. | |
| 8,460,865 B2 | 6/2013 | Chee et al. | |
| 8,462,981 B2 | 6/2013 | Determan et al. | |
| 8,481,258 B2 | 7/2013 | Church et al. | |
| 8,519,115 B2 | 8/2013 | Webster et al. | |
| 8,551,710 B2 | 10/2013 | Bernitz et al. | |
| 8,632,975 B2 | 1/2014 | Vander Horn et al. | |
| 8,658,361 B2 | 2/2014 | Wu et al. | |
| 8,658,365 B2 | 2/2014 | Bjornson et al. | |
| 8,771,950 B2 | 7/2014 | Church et al. | |
| 8,921,086 B2 | 12/2014 | Hanzel et al. | |
| 8,986,926 B2 | 3/2015 | Ferree et al. | |
| 9,201,063 B2 | 12/2015 | Sood et al. | |
| 9,273,349 B2 | 3/2016 | Nguyen et al. | |

(Continued)

FOREIGN PATENT DOCUMENTS

| | | |
|---|---|---|
| WO | WO 1991/017160 | 11/1991 |
| WO | WO 2017/143155 | 8/2017 |

(Continued)

OTHER PUBLICATIONS

Gao et al., Trends in Analytical Chemistry 121:11570 (Year: 2019).*

(Continued)

*Primary Examiner* — Ethan C Whisenant
(74) *Attorney, Agent, or Firm* — WILSON SONSINI GOODRICH & ROSATI

(57) ABSTRACT

The present disclosure relates in some aspects to methods for analyzing antigen receptor transcripts in a biological sample. In some aspects, nucleic acid molecules are generated from V(D)J transcripts in situ in the biological sample to enrich molecules comprising V(D)J joins. In some aspects, the presence, amount, and/or identity of a plurality of V(D)J transcripts are analyzed in situ. Also provided are oligonucleotides, sets of oligonucleotides, compositions, and kits for use in accordance with the methods.

20 Claims, 7 Drawing Sheets

(56)　　　　　References Cited

U.S. PATENT DOCUMENTS

| | | |
|---|---|---|
| 9,279,155 B2 | 3/2016 | Bjornson et al. |
| 9,371,563 B2 | 6/2016 | Geiss et al. |
| 9,371,598 B2 | 6/2016 | Chee |
| 9,376,717 B2 | 6/2016 | Gao et al. |
| 9,512,422 B2 | 12/2016 | Barnard et al. |
| 9,541,504 B2 | 1/2017 | Hoyt |
| 9,551,032 B2 | 1/2017 | Landegren et al. |
| 9,617,591 B2 | 4/2017 | Moysey et al. |
| 9,624,538 B2 | 4/2017 | Church et al. |
| 9,650,406 B2 | 5/2017 | Zhou et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,758,823 B2 | 9/2017 | Moysey et al. |
| 9,778,155 B2 | 10/2017 | Gradinaru et al. |
| 9,783,841 B2 | 10/2017 | Nolan et al. |
| 9,797,009 B2 | 10/2017 | Heron et al. |
| 9,889,422 B2 | 2/2018 | Smith et al. |
| 9,909,167 B2 | 3/2018 | Samusik et al. |
| 10,032,064 B2 | 7/2018 | Hoyt |
| 10,059,990 B2 | 8/2018 | Boyden et al. |
| 10,126,242 B2 | 11/2018 | Miller et al. |
| 10,179,932 B2 | 1/2019 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,385,382 B2 | 8/2019 | Moysey et al. |
| 10,415,080 B2 | 9/2019 | Dunaway et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,545,075 B2 | 1/2020 | Deisseroth et al. |
| 10,580,128 B2 | 3/2020 | Miller |
| 10,640,816 B2 | 5/2020 | Beechem et al. |
| 10,640,826 B2 | 5/2020 | Church et al. |
| 10,669,569 B2 | 6/2020 | Gullberg et al. |
| 10,724,078 B2 | 7/2020 | Van Driel et al. |
| 10,746,981 B2 | 8/2020 | Tomer et al. |
| 10,774,372 B2 | 9/2020 | Chee et al. |
| 10,774,374 B2 | 9/2020 | Frisén et al. |
| 10,794,802 B2 | 10/2020 | Gradinaru et al. |
| 10,802,262 B2 | 10/2020 | Tomer et al. |
| 10,808,234 B2 | 10/2020 | Zhang et al. |
| 10,815,519 B2 | 10/2020 | Husain et al. |
| 10,829,814 B2 | 11/2020 | Fan et al. |
| 10,844,426 B2 | 11/2020 | Daugharthy et al. |
| 10,858,698 B2 | 12/2020 | Church et al. |
| 10,872,679 B2 | 12/2020 | Cai et al. |
| 10,964,001 B2 | 3/2021 | Miller |
| 11,155,860 B2 | 10/2021 | White et al. |
| 11,174,281 B1 | 11/2021 | Graham et al. |
| 11,180,741 B2 | 11/2021 | Heron et al. |
| 11,287,422 B2 | 3/2022 | Previte et al. |
| 11,434,525 B2 | 9/2022 | Glezer |
| 11,459,603 B2 | 10/2022 | Tyagi et al. |
| 11,499,185 B2 | 11/2022 | Vijayan et al. |
| 11,643,679 B2 | 5/2023 | Glezer et al. |
| 11,999,999 B2 | 6/2024 | Ju et al. |
| 2001/0024812 A1* | 9/2001 | Guegler ............. C12N 15/1096 |
| | | 435/91.5 |
| 2002/0045045 A1 | 4/2002 | Adams et al. |
| 2002/0062017 A1* | 5/2002 | Hecker .............. C12N 15/1096 |
| | | 435/7.1 |
| 2002/0110807 A1* | 8/2002 | Pilarski ................ C12Q 1/6886 |
| | | 435/6.16 |

| | | |
|---|---|---|
| 2003/0017264 A1 | 1/2003 | Treadway et al. |
| 2004/0253598 A1* | 12/2004 | Baughn .................. C07K 14/47 |
| | | 435/325 |
| 2005/0064465 A1* | 3/2005 | Dettloff ................. B01L 3/5027 |
| | | 435/5 |
| 2006/0154286 A1* | 7/2006 | Kong ...................... C12P 19/34 |
| | | 435/6.12 |
| 2010/0055733 A1 | 3/2010 | Lutolf et al. |
| 2011/0223585 A1 | 9/2011 | Gullberg et al. |
| 2013/0288249 A1 | 10/2013 | Gullbert |
| 2013/0323729 A1 | 12/2013 | Landegren et al. |
| 2014/0120534 A1* | 5/2014 | Bernitz ................ C12Q 1/6809 |
| | | 435/6.11 |
| 2015/0225801 A1* | 8/2015 | Cai ...................... C12Q 1/6888 |
| | | 506/9 |
| 2016/0024555 A1 | 1/2016 | Church et al. |
| 2016/0108458 A1 | 4/2016 | Frei et al. |
| 2016/0138086 A1* | 5/2016 | Seelig .................. C12Q 1/6855 |
| | | 506/26 |
| 2016/0305856 A1 | 10/2016 | Boyden et al. |
| 2016/0376642 A1 | 12/2016 | Landegren et al. |
| 2017/0009278 A1 | 1/2017 | Söderberg et al. |
| 2017/0067096 A1* | 3/2017 | Wassie ...................... G01N 1/36 |
| 2017/0081489 A1 | 3/2017 | Rodriques et al. |
| 2017/0101672 A1 | 4/2017 | Luo et al. |
| 2017/0219465 A1 | 8/2017 | Desseroth et al. |
| 2017/0220733 A1 | 8/2017 | Zhuang et al. |
| 2017/0253918 A1 | 9/2017 | Kohman |
| 2018/0052081 A1 | 2/2018 | Kohman |
| 2018/0080876 A1 | 3/2018 | Rockel et al. |
| 2018/0208967 A1 | 7/2018 | Larman et al. |
| 2018/0237864 A1 | 8/2018 | Imler et al. |
| 2018/0251833 A1 | 9/2018 | Daugharthy et al. |
| 2018/0320226 A1 | 11/2018 | Church et al. |
| 2019/0017106 A1 | 1/2019 | Frisen et al. |
| 2019/0032128 A1 | 1/2019 | Chen et al. |
| 2019/0055594 A1 | 2/2019 | Samusik et al. |
| 2019/0112599 A1 | 4/2019 | Church et al. |
| 2019/0119735 A1 | 4/2019 | Deisseroth et al. |
| 2019/0155835 A1 | 5/2019 | Daugharthy et al. |
| 2019/0161796 A1 | 5/2019 | Hauling et al. |
| 2019/0177718 A1 | 6/2019 | Church et al. |
| 2019/0194709 A1 | 6/2019 | Church et al. |
| 2019/0218608 A1 | 7/2019 | Daugharthy et al. |
| 2019/0249248 A1 | 8/2019 | Beechem et al. |
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2019/0339203 A1 | 11/2019 | Miller et al. |
| 2019/0367997 A1 | 12/2019 | Bent et al. |
| 2020/0010891 A1 | 1/2020 | Beechem et al. |
| 2020/0071751 A1 | 3/2020 | Daugharthy et al. |
| 2020/0123597 A1 | 4/2020 | Daniel |
| 2020/0140920 A1 | 5/2020 | Pierce et al. |
| 2020/0224243 A1 | 7/2020 | Desai et al. |
| 2020/0224244 A1 | 7/2020 | Nilsson et al. |
| 2020/0239946 A1 | 7/2020 | Dewal |
| 2020/0354774 A1 | 11/2020 | Church et al. |
| 2020/0354782 A1 | 11/2020 | Dewal |
| 2020/0362398 A1 | 11/2020 | Kishi et al. |
| 2020/0393343 A1 | 12/2020 | Kennedy-Darling et al. |
| 2021/0017587 A1 | 1/2021 | Cai et al. |
| 2021/0115504 A1 | 4/2021 | Cai et al. |
| 2021/0238662 A1 | 8/2021 | Bava |
| 2021/0238674 A1 | 8/2021 | Bava |
| 2021/0254140 A1 | 8/2021 | Stahl et al. |
| 2021/0262018 A1 | 8/2021 | Bava et al. |
| 2021/0277460 A1 | 9/2021 | Bava |
| 2021/0340618 A1 | 11/2021 | Kuhnemund et al. |
| 2021/0340621 A1 | 11/2021 | Daugharthy et al. |
| 2021/0388423 A1 | 12/2021 | Bava et al. |
| 2021/0388424 A1 | 12/2021 | Bava |
| 2022/0010358 A1 | 1/2022 | Kuhnemund et al. |
| 2022/0049302 A1 | 2/2022 | Daugharthy et al. |
| 2022/0049303 A1 | 2/2022 | Busby et al. |
| 2022/0064697 A1 | 3/2022 | Zhuang et al. |
| 2022/0083832 A1 | 3/2022 | Shah |
| 2022/0084628 A1 | 3/2022 | Shah |
| 2022/0084629 A1 | 3/2022 | Shah |

(56) References Cited

U.S. PATENT DOCUMENTS

| | | |
|---|---|---|
| 2022/0136049 A1 | 5/2022 | Bava et al. |
| 2022/0186300 A1 | 6/2022 | Bava |
| 2022/0195498 A1 | 6/2022 | Kuhnemund et al. |
| 2022/0213529 A1 | 7/2022 | Kuhnemund et al. |
| 2022/0228200 A1 | 7/2022 | Bava |
| 2022/0235403 A1 | 7/2022 | Costa |
| 2022/0282306 A1 | 9/2022 | Bava et al. |
| 2022/0282316 A1 | 9/2022 | Bava |
| 2022/0282319 A1 | 9/2022 | Verheyen |
| 2022/0372570 A1 | 11/2022 | Costa |
| 2022/0380838 A1 | 12/2022 | Kuhnemund et al. |
| 2022/0403458 A1 | 12/2022 | Bava |
| 2023/0002808 A1 | 1/2023 | Mignardi |
| 2023/0012607 A1 | 1/2023 | Kuhnemund et al. |
| 2023/0013775 A1 | 1/2023 | Chen et al. |
| 2023/0015226 A1 | 1/2023 | Chen et al. |
| 2023/0026886 A1 | 1/2023 | Chen |
| 2023/0031305 A1 | 2/2023 | Hernandez Neuta et al. |
| 2023/0031996 A1 | 2/2023 | Hernandez Neuta et al. |
| 2023/0035685 A1 | 2/2023 | Hernandez Neuta et al. |
| 2023/0037182 A1 | 2/2023 | Bava et al. |
| 2023/0039148 A1 | 2/2023 | Verheyen |
| 2023/0039899 A1 | 2/2023 | Larman et al. |
| 2023/0041485 A1 | 2/2023 | Hernandez Neuta et al. |
| 2023/0044650 A1 | 2/2023 | Dockter |
| 2023/0057571 A1 | 2/2023 | Costa et al. |
| 2023/0061542 A1 | 3/2023 | Kuhnemund |
| 2023/0084407 A1 | 3/2023 | Hernandez Neuta et al. |
| 2023/0159997 A1 | 5/2023 | Belhocine et al. |
| 2023/0160794 A1 | 5/2023 | Dockter et al. |
| 2023/0183787 A1 | 6/2023 | Bava et al. |
| 2023/0242974 A1 | 8/2023 | Costa et al. |
| 2023/0279465 A1 | 9/2023 | He et al. |
| 2023/0279475 A1 | 9/2023 | Kuhnemund et al. |
| 2023/0279480 A1 | 9/2023 | Kuhnemund |
| 2023/0287478 A1 | 9/2023 | Bava |
| 2023/0314327 A1 | 10/2023 | Hoffman |
| 2023/0314328 A1 | 10/2023 | Costa |
| 2023/0323427 A1 | 10/2023 | Schnall-Levin |
| 2023/0323430 A1 | 10/2023 | Shastry |
| 2023/0323437 A1 | 10/2023 | Chen et al. |
| 2023/0374573 A1 | 11/2023 | Qian et al. |
| 2023/0374580 A1 | 11/2023 | Costa |
| 2023/0416821 A1 | 12/2023 | Bava et al. |
| 2024/0002902 A1 | 1/2024 | Jakobsen et al. |
| 2024/0026426 A1 | 1/2024 | Bava |
| 2024/0026427 A1 | 1/2024 | Kuhnemund et al. |
| 2024/0026439 A1 | 1/2024 | Sasaki |
| 2024/0026448 A1 | 1/2024 | Costa |
| 2024/0035070 A1 | 2/2024 | Christopherson |
| 2024/0035071 A1 | 2/2024 | Delaney et al. |
| 2024/0035072 A1 | 2/2024 | Christopherson |
| 2024/0043910 A1 | 2/2024 | Shastry |
| 2024/0043914 A1 | 2/2024 | Chen et al. |
| 2024/0060119 A1 | 2/2024 | Bava |
| 2024/0084373 A1 | 3/2024 | Shastry |
| 2024/0084378 A1 | 3/2024 | Marks et al. |
| 2024/0101978 A1 | 3/2024 | Boghospor et al. |
| 2024/0132938 A1 | 4/2024 | Kuhnemund |
| 2024/0141418 A1 | 5/2024 | Mielinis |
| 2024/0150816 A1 | 5/2024 | Feng et al. |
| 2024/0158852 A1 | 5/2024 | Belhocine et al. |
| 2024/0167081 A1 | 5/2024 | Bava et al. |
| 2024/0175082 A1 | 5/2024 | Costa |
| 2024/0175083 A1 | 5/2024 | Bava et al. |
| 2024/0191297 A1 | 6/2024 | Christopherson et al. |
| 2024/0209330 A1 | 6/2024 | Shastry et al. |
| 2024/0218424 A1 | 7/2024 | Costa et al. |
| 2024/0218437 A1 | 7/2024 | Belhocine et al. |
| 2024/0263219 A1 | 8/2024 | Kuhnemund |
| 2024/0263220 A1 | 8/2024 | Olofsson |
| 2024/0263222 A1* | 8/2024 | Lawson ............... C12Q 1/6841 |
| 2024/0264155 A1 | 8/2024 | Costa |

FOREIGN PATENT DOCUMENTS

| | | |
|---|---|---|
| WO | WO 2019/010486 | 1/2019 |
| WO | WO 2019/199579 | 10/2019 |
| WO | WO 2020/076976 | 4/2020 |
| WO | WO 2020/076979 | 4/2020 |
| WO | WO 2020/096687 | 5/2020 |
| WO | WO 2020/099640 | 5/2020 |
| WO | WO 2020/117914 | 6/2020 |
| WO | WO 2020/123316 | 6/2020 |
| WO | WO 2020/123742 | 6/2020 |
| WO | WO 2020/142490 | 7/2020 |
| WO | WO 2020/240025 | 12/2020 |
| WO | WO 2020/254519 | 12/2020 |
| WO | WO 2021/123282 | 6/2021 |
| WO | WO 2021/123286 | 6/2021 |
| WO | WO 2021/138676 | 7/2021 |
| WO | WO 2021/155063 | 8/2021 |
| WO | WO 2021/168326 | 8/2021 |
| WO | WO 2021/247568 | 12/2021 |
| WO | WO 2023/108139 | 6/2023 |
| WO | WO 2023/141476 | 7/2023 |
| WO | WO 2023/172915 | 9/2023 |
| WO | WO 2023/192302 | 10/2023 |
| WO | WO 2024/148300 | 7/2024 |

OTHER PUBLICATIONS

Logan et al. PNAS 108(52) : 21194-21199 (Year: 2011).*

Whitting et al. ,Journal of Virology 68(8) : 4747-4758 (Year: 1994).*

Allawi et al., "Thermodynamics and NMR of internal G.T mismatches in DNA," Biochemistry, (1997) 36:10581-94.

Archer et al., "Selective and flexible depletion of problematic sequences from RNA-seq libraries at the cDNA stage," BMC Genomics. (2014) 15(1):401.

Barnes et al., "A Single Amino Acid Change to Taq DNA Polymerase Enables Faster PCR, Reverse Transcription and Strand-Displacement," Front Bioeng Biotechnol. (2021) 8:553474. doi: 10.3389/fbioe.2020.553474.

Bibikova et al., "Quantitative gene expression profiling in formalin-fixed, paraffin-embedded tissues using universal bead arrays," Am J Pathol. Nov. 2004; 165(5):1799-807.

Bolognesi et al., "Multiplex Staining by Sequential Immunostaining and Antibody Removal on Routine Tissue Sections," J. Histochem. Cytochem. (2017); 65(8): 431-444.

Calis et al., "Characterizing immune repertoires by high throughput sequencing: strategies and applications," Trends Immunol+. Dec. 2014;35(12):581-590.

Capodieci et al., "Gene expression profiling in single cells within tissue," Nat Methods. (2005) 2(9): 663-5.

Chen et al., "Nanoscale imaging of RNA with expansion microscopy," Nat Methods. (2016) 13:679-684.

Chen et al., "Expansion Microscopy," Science (2015) 347(6221):543-548.

Conze et al., "Single molecule analysis of combinatorial splicing," Nucleic Acids Res. (2010) 38(16): e163.

Femino et al., "Visualization of single RNA transcripts in situ," Science. (1998) 280(5363): 585-90.

Gavrilovic et al., "Automated classification of multicolored rolling circle products in dual-channel wide-field fluorescence microscopy," Cytometry A. (2011) 79(7): 518-27.

Geiss et al., "Direct multiplexed measurement of gene expression with color-coded probe pairs," Nat Biotechnol. (2008) 26(3): 317-25.

Glass et al., "SIMPLE: a sequential immunoperoxidase labeling and erasing method," J Histochem Cytochem. (2009) 57(10); 899-905.

Goh, J.J.L. et al. (Jul. 2020, e-pub. Jun. 15, 2020). "Highly Specific Multiplexed RNA Imaging In Tissues With Split-FISH," Nat Methods 17(7):689-693. doi: 10.1038/s41592-020-0858-0. Epub Jun. 15, 2020.

Goransson et al., "A single molecule array for digital targeted molecular analyses," Nucleic Acids Res. 2009 37(1):e7. doi: 10.1093/nar/gkn921.

(56)        References Cited

OTHER PUBLICATIONS

Gunderson et al. "Decoding randomly ordered DNA arrays." Genome research 14.5 (2004): 870-877.

Han et al., "Quantum-dot-tagged microbeads for multiplexed optical coding of biomolecules," Nat Blotechnol. (2001) 19(7): 631-5.

Henegariu et al., "Custom fluorescent-nucleotide synthesis as an alternative method for nucleic acid labeling," Nature Biotechnol. (2000) 18:345.

Itzkovitz et al., "Single-molecule transcript counting of stem-cell markers in the mouse intestine," Nat Cell Biol. (2011) 14(1): 106-14.

Itzkovitz et al., "Validating Transcripts with Probes and Imaging Technology," Nat Methods. (2011) 8(4 Suppl): S12-S19.

Jamur et al., "Permeabilization of cell membranes," Method Mol. Biol. (2010) 588: 63-66 (abstract only).

Kanehisa, "Use of statistical criteria for screening potential homologies in nucleic acid sequences," Nucleic Acids Res. (1984) 12:203-213.

Lagunavicius et al., "Novel application of Phi29 DNA polymerase: RNA detection and analysis in vitro and in situ by target RNA-primed RCA," RNA. (2009) 15(5):765-71.

Larsson et al. "In situ detection and genotyping of individual mRNA molecules," Nat Methods. (2010) 7(5):395-397.

Levsky et al., "Fluorescence in situ hybridization: past, present and future," J Cell Sci. (2003) 116(Pt 14): 2833-8.

Levsky et al., "Single-cell gene expression profiling," Science. (2002) 297(5582): 836-40.

Lin et al., "Highly multiplexed imaging of single cells using a high-throughput cyclic immunofluorescence method," Nat Commun. (2015) 6:8390.

Liu et al. Barcoded oligonucleotides ligated on RNA amplified for multiplexed and parallel in situ analyses. Nucleic Acids Res. (2021) 49(10):e58, 15 pages. doi: 10.1093/nar/gkab120.

Maierhorfer et al., "Multicolor deconvolution microscopy of thick biological specimens," Am J Pathol. (2003) 162(2): 373-9.

Martín-Alonso et al., "Defective Strand-Displacement DNA Synthesis Due to Accumulation of Thymidine Analogue Resistance Mutations in HIV-2 Reverse Transcriptase," ACS Infect. Dis. (2020) 6, 5, 1140-1153.

McGinn et al., "New technologies for DNA analysis—a review of the READNA Project," N Biotechnol. (2016) 33(3): 311-30. doi: 10.1016/j.nbt.2015.10.003.

Meade et al. "Multiplexed DNA detection using spectrally encoded porous SiO2 photonic crystal particles," Anal Chem. (2009) 81(7): 2618-25.

Payne et al. "In situ genome sequencing resolves DNA sequence and structure in intact biological samples," Science. (2021) 371(6532): eaay3446. doi: 10.1126/science.aay3446. Epub Dec. 31, 2020.

Pirici et al., "Antibody elution method for multiple immunohistochemistry on primary antibodies raised in the same species and of the same subtype," J Histochem Cytochem. (2009) 57(6); 567-75.

Raj et al., "Imaging individual mRNA molecules using multiple singly labeled probes," Nat Methods. (2008) 5(10): 877-879.

Rouhanifard et al. "ClampFISH detects individual nucleic acid molecules using click chemistry-based amplification," Nat Biotechnol. (2018) 17 pages. doi: 10.1038/nbt.4286.

Sun et al., "Composite organic-inorganic nanoparticles as Raman labels for tissue analysis," Nano Lett. (2007) 7(2): 351-6.

Takei et al., (Feb. 2021, e-pub Jan. 27, 2021). "Integrated Spatial Genomics Reveals Global Architecture Of Single Nuclei," Nature 590(7845):344-350, 53 pages. doi: 10.1038/s41586-020-03126-2.

Vandernoot et al., "cDNA normalization by hydroxyapatite chromatography to enrich transcriptome diversity in RNA-seq applications," Biotechniques, (2012) 53(6) 373-80.

Wählby et al., "Sequential immunofluorescence staining and image analysis for detection of large numbers of antigens in individual cell nuclei," Cytometry. (2002) 47(1): 32-41.

Weibrecht et al., "Simultaneous visualization of both signaling cascade activity and end-point gene expression in single cells," PLoS One. (2011) 6(5): e20148.

Wetmur, "Dna Probes: Applications of the Principles of Nucleic Acid Hybridization," Critical Reviews in Biochemistry and Molecular Biology, (1991) 26(91); 227-259.

Wilson et al., "Encoded microcarriers for high-throughput multiplexed detection," Angew Chem Int Ed Engl. (2006) 18;45(37): 6104-17.

Wu, C. et al. "RollFISH Achieves Robust Quantification Of Single-Molecule RNA Biomarkers In Paraffin-Embedded Tumor Tissue Samples," Commun Biol. (2018) 1:(209):1-8. doi: 10.1038/s42003-018-0218-0.

Yershov et al., "DNA analysis and diagnostics on oligonucleotide microchips," Proc Natl Acad Sci USA. (1996) 93(10): 4913-4918.

Zhang et al., "Multiplex ligation-dependent probe amplification (MLPA) for ultrasensitive multiplexed microRNA detection using ribonucleotide-modified DNA probes," Chem Commun (Camb). (2013) 49(85): 10013-5.

Zhao et al., "Advances of multiplex and high throughput biomolecular detection technologies based on encoding microparticles," Sci China Chem. (2011) 54(8):1185.

Chen et al., "Efficient in situ barcode sequencing using padlock probe-based BaristaSeq," Nucleic Acids Res. (2018) 46(4): e22.

Sun et al., "Integrating barcoded neuroanatomy with spatial transcriptional profiling enables identification of gene correlates of projections," Nat Neurosci. (2021) 24(6):873-885.

* cited by examiner

*FIG. 1*

METHODS AND COMPOSITIONS FOR IN SITU ANALYSIS OF V(D)J SEQUENCES

CROSS-REFERENCE TO RELATED APPLICATION

This application claims priority to U.S. Provisional Patent Application No. U.S. 63/339,390, filed May 6, 2022, entitled "METHODS AND COMPOSITIONS FOR IN SITU ANALYSIS OF V(D)J SEQUENCES," which is herein incorporated by reference in its entirety for all purposes.

FIELD

The present disclosure relates in some aspects to methods and compositions for analysis of a target nucleic acid in a sample (e.g., in situ), such as in situ immunoprofiling.

BACKGROUND

Adaptive immunity is based on clonal selection and expansion from a repertoire of T and B lymphocytes bearing a diversity of cell-surface receptors and antibodies that recognize specific antigens. The enormous diversity of lymphocyte receptors and antibodies expressed from a relatively small number of gene segments is largely made possible through V(D)J recombination. The hypervariable recombined V(D)J transcripts in turn determine the affinity of the Complementary Determining Regions (CDRs) in antigen receptors to bind to specific epitopes. While the spatial distribution of antigen receptor proteins such as T cell receptors (TCRs) and B cell receptors (BCRs) in a biological sample can be detected using reagents (e.g., antibodies) recognizing the receptor proteins, detecting V(D)J transcripts in situ and analyzing their spatial distribution in cell or tissue samples remains challenging. Provided herein are methods, compositions, and kits that address such and other needs.

BRIEF SUMMARY

Insights into antigen receptor diversity, including the spatial distribution of antigen receptor transcripts in cells and tissues, are crucial to understanding disease development and establishing new treatment strategies.

In some embodiments, provided herein is a method for analyzing a biological sample, comprising generating a nucleic acid molecule, wherein the generation comprises reverse transcribing an antigen receptor transcript at a location in the biological sample, and immobilizing the nucleic acid molecule at the location, wherein the nucleic acid molecule comprises a V(D)J join comprising a V (variable) segment and a J (joint) segment. In some embodiments, the nucleic acid molecule comprises a VDJ join comprising a D (diversity) segment between the V and J segments. In some embodiments, the method further comprises circularizing the nucleic acid molecule or a circularizable probe or probe set hybridized to the nucleic acid molecule to generate a circularized molecule. In some embodiments, the method further comprises generating a rolling circle amplification (RCA) product of the circularized molecule. In some embodiments, the method further comprises detecting a signal associated with the RCA product, thereby detecting the antigen receptor transcript or a sequence thereof at the location in the biological sample.

In any of the embodiments herein, the nucleic acid molecule can comprise a cDNA sequence complementary to a sequence of the antigen receptor transcript, or a complement of the cDNA sequence.

In any of the embodiments herein, the antigen receptor transcript can be reverse transcribed using a polymerase having strand displacement activity. In any of the embodiments herein, the antigen receptor transcript can be reverse transcribed in the presence of a helicase having strand displacement activity.

In any of the embodiments herein, the antigen receptor transcript can be reverse transcribed using one or more primers that hybridize to a C (constant) region sequence in the antigen receptor transcript. In some embodiments, the one or more primers each comprises a 5' overhang upon hybridization to the antigen receptor transcript.

In any of the embodiments herein, the antigen receptor transcript can be reverse transcribed using at least two, at least three, at least four, at least five, or more primers that hybridize to adjacent sequences in the C (constant) region in the antigen receptor transcript. In some embodiments, the adjacent sequences are non-overlapping with one another.

In any of the embodiments herein, extension of a particular 5' primer can displace an extension product of one or more 3' primers hybridized to the antigen receptor transcript. In some embodiments, the extension products of the primers are covalently or non-covalently linked to one or more molecules at the location. In some embodiments, the extension products of the primers comprise functional groups capable of reacting with each other and/or with functional groups in the one or more molecules. In any of the embodiments herein, the one or more molecules may be endogenous in the biological sample or may be in a matrix in or embedding the biological sample.

In any of the embodiments herein, modified nucleotides can be incorporated into the extension products of the one or more primers during reverse transcription, and functional groups in the modified nucleotides are capable of reacting with each other and/or with functional groups in a cellular matrix and/or a polymeric matrix in or embedding the biological sample.

In any of the embodiments herein, the antigen receptor transcript can comprise a sequence 5' to the V segment. In any of the embodiments herein, the antigen receptor transcript can comprise an L (leader) sequence 5' to the V segment. In any of the embodiments herein, the antigen receptor transcript can comprise an adaptor sequence 5' to the V segment and/or 5' to the L (leader) sequence. In some embodiments, the adaptor sequence is an invariable sequence ligated to the 5' end of the V segment in the antigen receptor transcript.

In any of the embodiments herein, the antigen receptor transcript can be reverse transcribed to generate a cDNA molecule. In some embodiments, the cDNA molecule comprises 3' poly-C, and a template switching oligonucleotide comprising an adaptor sequence and 3' poly-G is hybridized to the cDNA molecule to introduce a complement of the adaptor sequence into the cDNA molecule. In some embodiments, the method further comprises amplifying the cDNA molecule using one or more PCR primers, wherein the amplification products are immobilized at the location in the biological sample. In some embodiments, modified nucleotides can be incorporated into the amplification products, and functional groups in the modified nucleotides are capable of reacting with each other and/or with functional groups in a cellular matrix and/or a polymeric matrix in or embedding the biological sample, thereby immobilizing the amplification products at the location in the biological sample.

In some embodiments, provided herein is a method for analyzing a biological sample, comprising generating a nucleic acid molecule, wherein the generation comprises reverse transcribing an antigen receptor transcript at a location in the biological sample; immobilizing the nucleic acid molecule at the location, wherein the nucleic acid molecule is a cDNA comprising a V(D)J join comprising a V (variable) segment and a J (joint) segment; and contacting the biological sample with a circularizable probe or probe set that hybridizes to the nucleic acid molecule. In some embodiments, provided herein is a method for analyzing a biological sample, comprising generating a nucleic acid molecule, wherein the generation comprises reverse transcribing an antigen receptor transcript at a location in the biological sample; immobilizing the nucleic acid molecule at the location, wherein the nucleic acid molecule is a cDNA comprising a V(D)J join comprising a V (variable) segment, a J (joint) segment, and a D (diversity) segment between the V and J segments; and contacting the biological sample with a circularizable probe or probe set that hybridizes to the nucleic acid molecule. In some embodiments, the method further comprises ligating the circularizable probe or probe set using the nucleic acid molecule as a template to generate a circularized probe. In some embodiments, the V(D)J join is a VDJ join and the circularized probe comprises complements of the V segment, the D segment, and the J segment. In some embodiments, the method further comprises generating a rolling circle amplification (RCA) product of the circularized probe, and the RCA product comprises multiple copies of the VDJ join. In some embodiments, the method further comprises detecting a signal associated with the VDJ join in the RCA product, thereby detecting the antigen receptor transcript or a sequence thereof at the location in the biological sample.

In any of the embodiments herein, the circularizable probe or probe set can comprises a 3' region that hybridizes to a sequence in and/or 3' to the V segment of the nucleic acid molecule (e.g., a cDNA comprising a V(D)J sequence); and a 5' region that hybridizes to a sequence in and/or 5' to the J segment of the nucleic acid molecule. In some embodiments, the 3' region hybridizes to a sequence in the V segment and the 5' region hybridizes to a sequence in the J segment. In some embodiments, the 3' region hybridizes to a sequence 3' to the V segment and the 5' region hybridizes to a sequence 5' to the J segment. In some embodiments, the sequence 3' to the V segment is an invariable adaptor sequence and the sequence 5' to the J segment is a C (constant) region sequence.

In any of the embodiments herein, the method can comprise using a polymerase to extend the 3' region (of the circularizable probe or probe set) using the nucleic acid molecule as a template and using a ligase to ligate the extended 3' region to the 5' region (of the circularizable probe or probe set) using the nucleic acid molecule as a template, thereby filling a gap between the 3' region and the 5' region hybridized to the nucleic acid molecule. In some embodiments, the extended 3' region comprises a sequence complementary to the V(D)J join or a portion thereof. In some embodiments, the extended 3' region comprises a sequence complementary to the D segment of the nucleic acid molecule. In some embodiments, the extended 3' region comprises a sequence complementary to the D segment of the nucleic acid molecule and a sequence complementary to the V segment (or a portion thereof) and/or a sequence complementary to the J segment (or a portion thereof) of the nucleic acid molecule.

In any of the embodiments herein, the method can comprise hybridizing an oligonucleotide to the nucleic acid molecule between the 3' region and the 5' region of the circularizable probe or probe set, and using a ligase to ligate the 3' region and the 5' region to the 5' end and the 3' end, respectively, of the oligonucleotide, thereby filling a gap between the 3' region and the 5' region hybridized to the nucleic acid molecule. In some embodiments, the oligonucleotide comprises a sequence complementary to the V(D)J join or a portion thereof. In some embodiments, the oligonucleotide comprises a sequence complementary to the D segment of the nucleic acid molecule. In some embodiments, the oligonucleotide comprises a sequence complementary to the D segment of the nucleic acid molecule, and a sequence complementary to the V segment (or a portion thereof) and/or a sequence complementary to the J segment (or a portion thereof) of the nucleic acid molecule. In some embodiments, the oligonucleotide is in a library of oligonucleotides contacted with the biological sample. In some embodiments, the library comprises at least about 1,000, at least about 5,000, at least about 10,000, or more oligonucleotides of different sequences. In any of the embodiments herein, the library can be randomly or partially randomly generated. In any of the embodiments herein, the library can comprise oligonucleotides comprising one or more degenerate sequences.

In any of the embodiments herein, the circularizable probe or probe set can comprise a barcode region comprising one or more barcode sequences.

In some embodiments, provided herein is a method for analyzing a biological sample, comprising generating a nucleic acid molecule, wherein the generation comprises reverse transcribing an antigen receptor transcript at a location in the biological sample; circularizing the nucleic acid molecule at the location, wherein the nucleic acid molecule comprises a V(D)J join comprising a V (variable) segment, a J (joint) segment, and optionally a D (diversity) segment between the V and J segments. In some embodiments, the V(D)J join is a VDJ join and the circularized nucleic acid molecule comprises the V segment, the D segment, and the J segment. In some embodiments, the method further comprises generating a rolling circle amplification (RCA) product of the circularized nucleic acid molecule, and the RCA product comprises multiple copies of a complement of the VDJ join. In some embodiments, the method further comprises detecting a signal associated with the complement of the VDJ join in the RCA product, thereby detecting the antigen receptor transcript or a sequence thereof at the location in the biological sample.

In any of the embodiments herein, the nucleic acid molecule can be circularized using template-independent ligation. In some embodiments, the template-independent ligation is click chemistry ligation or enzymatic ligation. In any of the embodiments herein, the nucleic acid molecule can be circularized using a single-stranded DNA (ssDNA) ligase. In some embodiments, the ssDNA ligase is a bacteriophage TS2126 RNA ligase or an archaebacterium RNA ligase or a variant or derivative thereof. In any of the embodiments herein, the nucleic acid molecule can be circularized using *Methanobacterium thermoautotrophicum* RNA ligase 1, CircLigase I, CircLigase II, T4 RNA ligase 1, or T4 RNA ligase 2, or a variant or derivative thereof.

In any of the embodiments herein, the nucleic acid molecule can be circularized using template-dependent ligation. In some embodiments, the template-dependent ligation is click chemistry ligation or enzymatic ligation.

In any of the embodiments herein, the nucleic acid molecule can be circularized using a splint that hybridizes to both ends of the nucleic acid molecule. In some embodiments, the nucleic acid molecule is a cDNA molecule and the splint comprises: a 3' region that hybridizes to a sequence in and/or 3' to the V segment of the cDNA molecule; and a 5' region that hybridizes to a sequence in and/or 5' to the J segment of the cDNA molecule. In some embodiments, the 3' region of the splint hybridizes to a sequence in the V segment of the cDNA molecule and/or the 5' region of the splint hybridizes to a sequence in the J segment of the cDNA molecule. In some embodiments, the 3' region of the splint hybridizes to a sequence 3' to the V segment of the cDNA molecule and the 5' region of the splint hybridizes to a sequence 5' to the J segment of the cDNA molecule. In some embodiments, the sequence 3' to the V segment is an invariable adaptor sequence and the sequence 5' to the J segment is a C (constant) region sequence.

In any of the embodiments herein, the splint can be or comprise a single-stranded splint, and the nucleic acid molecule can be circularized with or without gap filling prior to ligation. In any of the embodiments herein, the splint can comprise single-stranded 3' and 5' regions flanking a double-stranded region, and the nucleic acid molecule can be circularized with or without gap filling prior to ligation. In any of the embodiments herein, the splint can comprise a barcode region comprising one or more barcode sequences.

In any of the embodiments herein, the antigen receptor transcript can be a T cell receptor (TCR) transcript or an immunoglobulin (Ig) transcript. In some embodiments, the TCR transcript comprises a TCRα VJ join, a TCRβ VDJ join, a TCRγ VJ join, a TCRδ VDJ join, an Igκ VJ join, an Igλ VJ join, or an IgH VDJ join. In some embodiments, the TCR transcript comprises an TCRβ VDJ join. In some embodiments, the TCR transcript comprises an IgH VDJ join.

In any of the embodiments herein, the circularized molecule (e.g., the circularized nucleic acid molecule or the circularized probe) comprises a D segment of the antigen receptor transcript or a complement thereof. In some embodiments, the circularized molecule (e.g., the circularized nucleic acid molecule or the circularized probe) comprises a TCRβ VDJ join (or a portion of the TCRβ VDJ join comprising the D segment) of a TCRβ transcript or a complement thereof. In some embodiments, the circularized molecule (e.g., the circularized nucleic acid molecule or the circularized probe) comprises an IgH VDJ join (or a portion of the IgH VDJ join comprising the D segment) of an IgH transcript or a complement thereof.

In any of the embodiments herein, the RCA product can be generated in situ in the biological sample or a matrix embedding the biological sample. In any of the embodiments herein, the method can comprise imaging the biological sample to detect the RCA product in situ in the biological sample or a matrix embedding the biological sample. In any of the embodiments herein, the method can comprise detecting the RCA product using sequential hybridization of detectable probes, sequencing by hybridization, sequencing by ligation, sequencing by synthesis, sequencing by binding, or a combination thereof.

In some embodiments, disclosed herein is a method for analyzing a biological sample, comprising: a) reverse transcribing a plurality of antigen receptor transcripts at locations in the biological sample, wherein the antigen receptor transcript at a particular location in the biological sample is reverse transcribed to generate multiple cDNA molecules, and wherein each cDNA molecule comprises a VDJ join comprising a V (variable) segment, a D (diversity) segment, and a J (joint) segment; b) immobilizing the multiple cDNA molecules at the particular location; c) circularizing cDNA molecules for the plurality of antigen receptor transcripts or circularizable probes or probe sets each hybridized to one of the cDNA molecules to generate circularized molecules; d) generating rolling circle amplification (RCA) products of the circularized molecules; and e) detecting signals associated with the RCA products, thereby detecting the plurality of antigen receptor transcripts or sequences thereof at the locations in the biological sample. In some embodiments, each RCA product comprises multiple copies of a unit sequence comprising a sequence of the VDJ join or a complement thereof. In some embodiments, the unit sequence comprises the D segment of the VDJ join. In some embodiments, the unit sequence comprises the V segment or a portion thereof and/or the J segment or a portion thereof of the VDJ join.

In any of the embodiments herein, the unit sequence can be detected using sequential hybridization of detectable probes, sequencing by ligation, sequencing by synthesis, sequencing by binding, sequencing by hybridization, or a combination thereof.

In some embodiments, the unit sequence is sequenced using in situ sequencing by ligation (SBL) in the biological sample, thereby detecting a sequence of the VDJ join and detecting the corresponding antigen receptor transcript at one or more locations in the biological sample.

In some embodiments, the unit sequence is sequenced using in situ sequencing by synthesis (SBS) in the biological sample, thereby detecting a sequence of the VDJ join and detecting the corresponding antigen receptor transcript at one or more locations in the biological sample.

In some embodiments, the unit sequence is sequenced using in situ sequencing by binding (SBB) in the biological sample, thereby detecting a sequence of the VDJ join and detecting the corresponding antigen receptor transcript at one or more locations in the biological sample.

In some embodiments, a sequence of the VDJ join in the unit sequence is assigned a signal code sequence, and detecting the sequence of the VDJ join comprises: i) contacting the biological sample with a first detectable probe and a first detectably labeled oligonucleotide to generate a first complex comprising the first detectable probe hybridized to the unit sequence of the RCA product and the first detectably labeled oligonucleotide hybridized to the first detectable probe, wherein the first detectable probe comprises: a recognition sequence complementary to the unit sequence, and a first overhang sequence, and wherein the first detectably labeled oligonucleotide comprises: a sequence complementary to the first overhang sequence, and a first optically detectable moiety; ii) imaging the biological sample to detect a first signal from the first optically detectable moiety, wherein the first signal corresponds to a first signal code in the signal code sequence; iii) contacting the biological sample with a second detectable probe and a second detectably labeled oligonucleotide to generate a second complex comprising the second detectable probe hybridized to the unit sequence of the RCA product and the second detectably labeled oligonucleotide hybridized to the second detectable probe, wherein the second detectable probe comprises: a recognition sequence complementary to the unit sequence, and a second overhang sequence, and wherein the second detectably labeled oligonucleotide comprises: a sequence complementary to the second overhang sequence, and a second optically detectable moiety; and iv) imaging the biological sample to detect a second signal from the second optically detectable moiety, wherein the second signal corresponds to a second signal code in the signal code sequence, wherein the signal code sequence comprising at least the first signal code and the second signal code is determined at a location in the biological sample, thereby detecting the sequence of the VDJ join in the unit sequence and detecting the corresponding antigen receptor transcript at the location in the biological sample.

In any of the embodiments herein, the VDJ join can be among a plurality of VDJ joins, and the contacting in i) can comprise contacting the biological sample with a first pool of detectable probes and a universal pool of detectably labeled oligonucleotides, wherein the first pool of detectable probes comprises the first detectable probe and the universal pool of detectably labeled oligonucleotides comprises the first detectably labeled oligonucleotide and the second detectably labeled oligonucleotide, wherein each detectable probe in the first pool of detectable probe comprises (i) a recognition sequence complementary to one of the plurality of VDJ joins and (ii) an overhang sequence complementary to a detectably labeled oligonucleotide of the universal pool of detectably labeled oligonucleotides; and wherein the contacting in iii) can comprise contacting the biological sample with a second pool of detectable probes and the universal pool of detectably labeled oligonucleotides, wherein the second pool of detectable probes comprises the second detectable probe, and wherein each detectable probe in the second pool of detectable probes comprises (i) a recognition sequence complementary to one of the plurality of VDJ joins and (ii) an overhang sequence complementary to a detectably labeled oligonucleotide of the universal pool of detectably labeled oligonucleotides.

In any of the embodiments herein, the method can comprise identifying multiple different antigen receptor transcripts present at locations in the biological sample, wherein the VDJ join in each different antigen receptor transcript can be assigned a different signal code sequence and correspond to an oligonucleotide of a library of oligonucleotides.

In some embodiments, the plurality of VDJ joins comprises at least about 100, at least about 500, at least about 1,000, at least about 5,000, at least about 10,000, or more VDJ joins of different sequences, and/or the library of oligonucleotides comprises at least about 100, at least about 500, at least about 1,000, at least about 5,000, at least about 10,000, or more oligonucleotides comprising different VDJ sequences. In some embodiments, the biological sample is contacted with the library of oligonucleotides for ligation to the circularizable probes or probe sets to generate the circularized molecules. In some embodiments, the recognition sequence in each detectable probe comprises a sequence in a corresponding oligonucleotide in the library of oligonucleotides. In some embodiments, the number of different detectably labeled oligonucleotides in the universal pool is four.

In any of the embodiments herein, the first pool of detectable probes, a second pool of detectable probes, and one or more subsequent pools of detectable probes can be contacted with the sample in sequential cycles in a predetermined sequence which corresponds to the signal code sequence assigned to the sequence of the VDJ join, wherein detectable probes in the one or more subsequent pools each comprises (i) a recognition sequence complementary to one of the plurality of VDJ joins and (ii) an overhang sequence complementary to one of the detectably labeled oligonucleotides in the universal pool of detectably labeled oligonucleotides. In some embodiments, the sequential cycles comprise 5, 10, 15, 20, or more cycles.

In some embodiments, provided herein is a method for analyzing a biological sample, comprising: a) contacting the biological sample with a circularizable probe or probe set, wherein the biological sample comprises an antigen receptor transcript at a location, wherein the antigen receptor transcript comprises a V (variable) segment, a D (diversity) segment, and a J (joint) segment, and wherein the circularizable probe or probe set comprises: i) a 5' region that hybridizes to a sequence in and/or 5' to the V segment of the antigen receptor transcript; and ii) a 3' region that hybridizes to a sequence in and/or 3' to the J segment of the antigen receptor transcript; b) circularizing the circularizable probe or probe set hybridized to the antigen receptor transcript to generate a circularized probe; c) generating a rolling circle amplification (RCA) product of the circularized probe; and d) detecting a signal associated with the RCA product, thereby detecting the antigen receptor transcript or a sequence thereof at the location in the biological sample. In some embodiments, the method comprises prior to the circularizing in b), a step of extending the 3' region of the circularizable probe or probe set by a polymerase using the antigen receptor transcript as a template. In some embodiments, the polymerase is a reverse transcriptase with no or limited strand displacement activity.

In any of the embodiments herein, the biological sample can be a cell or tissue sample comprising cells or cellular components. In any of the embodiments herein, the biological sample can be a tissue section. In any of the embodiments herein, the biological sample can be a formalin-fixed, paraffin-embedded (FFPE) sample, a frozen tissue sample, or a fresh tissue sample. In any of the embodiments herein, the biological sample can be fixed and/or permeabilized. In any of the embodiments herein, the biological sample can be crosslinked and/or embedded in a matrix. In some embodiments, the matrix comprises a hydrogel. In any of the embodiments herein, the biological sample can be cleared.

BRIEF DESCRIPTION OF THE DRAWINGS

The drawings illustrate certain embodiments of the features and advantages of this disclosure. These embodiments are not intended to limit the scope of the appended claims in any manner.

FIG. 1 shows an exemplary method of reverse transcription of an antigen receptor transcript using a plurality of primers targeting sequences in the constant region and a strand displacing polymerase (e.g., a reverse transcriptase with strand displacing activity). The extension of a primer displaces the extension product of a 3' primer hybridized to the antigen receptor transcript. The cDNA products comprise VDJ sequences and may comprise poly-C sequences on their 3' ends.

DETAILED DESCRIPTION

Figure 2:
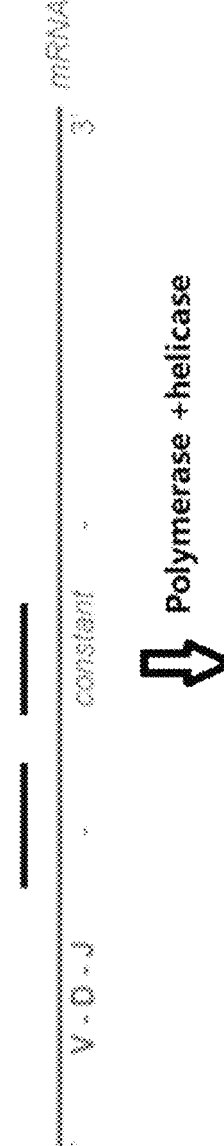
FIG. 2 shows an exemplary method of reverse transcription of an antigen receptor transcript using a plurality of primers targeting sequences in the constant region, a polymerase, and a helicase for displacing cDNA products.
Figure 2:

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

The practice of the techniques described herein may employ, unless otherwise indicated, conventional techniques and descriptions of organic chemistry, polymer technology, molecular biology (comprising recombinant techniques), cell biology, biochemistry, and sequencing technology, which are within the skill of those who practice in the art. Such conventional techniques comprise polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2003), *PCR Primer: A Laboratory Manual*; Bowtell and Sambrook (2003), *DNA Microarrays: A Molecular Cloning Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), *Molecular Cloning: A Laboratory Manual* (all from Cold Spring Harbor Laboratory Press); Stryer, L. (1995) *Biochemistry* (4th Ed.) W. H. Freeman, New York N.Y.; Gait, "*Oligonucleotide Synthesis: A Practical Approach*" 1984, IRL Press, London; Nelson and Cox (2000), Lehninger, *Principles of Biochemistry* 3rd Ed., W. H. Freeman Pub., New York, N.Y.; and Berg et al. (2002) *Biochemistry*, 5$^{th}$ Ed., W. H. Freeman Pub., New York, N.Y., all of which are herein incorporated in their entirety by reference for all purposes.

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Overview

Quick and cost-effectively measurement of antigen receptor diversity in a biological sample comprising immune cells is desirable. Immunoprofiling involving detection of antigen receptor transcripts can be used; however, current immunoprofiling approaches can suffer from low sensitivity, specificity, and/or detection efficiency at least partly due to the diverse nature of V(D)J sequences and the low copy number of transcript in a single cell. Thus, improved methods for analyzing V(D)J transcripts in a biological sample are needed. Provided herein are methods and compositions that address such and other needs.

In TCR and BCR RNA transcripts, the V(D)J sequences are 5' to the constant region exon(s) and the 3' poly(A) tail of the transcript. In cases where reverse transcription is performed using poly(T) as a primer, the efficiency of reverse transcription may not be sufficient to reach the 5' V(D)J sequences and generate cDNA molecules comprising complements of the V(D)J joins. It remains challenging to reverse transcribe V(D)J sequences in situ in a cell or tissue sample, particularly in crosslinked tissues. The number of V(D)J transcripts of a particular V(D)J join sequence in a sample comprising T cells or B cells of various antigen specificities can be low, and due to inefficient cDNA synthesis in situ, sequence information in particular V(D)J joins can be lost and become unavailable for subsequent in situ detection.

In some embodiments, provided herein is a method comprising enriching V(D)J sequences in situ in a cell or tissue sample. In some embodiments, nucleic acid molecules comprising V(D)J sequences or complements thereof, particularly the D segment sequences or complements thereof, are generated and immobilized in situ, for example, via crosslinking to one another and/or to other molecules in the sample or a matrix embedding the sample.

In some embodiments, the sample can be contacted with multiple primers targeting a constant region of an antigen receptor transcript, such that the primers are tiled on the transcript. In some embodiments, a polymerase with strand displacement activity can be used to reverse transcribe the antigen receptor transcript from the multiple primers. In some embodiments, a reverse transcriptase (e.g., one having no or limited strand displacement activity) and a helicase can be used, where the helicase can unwind a cDNA product from its template (the V(D)J transcript). In some embodiments, from a particular primer, multiple cDNA molecules can be generated, and each cDNA molecule can comprise a complement of the V(D)J sequence in the transcript. Moreover, the cDNA products of the particular primer can be displaced by primer extension from one or more 5' primers targeting the constant region. Likewise, primer extension from the particular primer can displace cDNA products of one or more 3' primers targeting the constant region. In some embodiments, each of the cDNA products of the 3' primer (s), the particular primer, and the 5' primer(s) can comprise a complement of the V(D)J sequence in the transcript, thereby enriching cDNA molecules that can be detected in situ in order to detect the V(D)J sequence in the transcript.

In some embodiments, the cDNA molecules are kept in place and prevented from diffusing away, once the cDNA molecules branch off from the transcript and become displaced. In some embodiments, reverse transcription from the primers is allowed to proceed for a short time, thereby limiting the number of cDNA molecules that can branch off and diffuse, followed by fixing and/or crosslinking the sample to keep the cDNA molecules in place. In some embodiments, modified nucleotides comprising functional groups (e.g., crosslinking moieties) can be incorporated into the cDNA molecules during the reverse transcription. In some embodiments, the modified nucleotides account for between about 1% and about 10% of total nucleotides added to the sample for reverse transcription. In some embodiments, the modified nucleotides, once incorporated into cDNA molecules, are crosslinked to each other and/or to other molecules. In some embodiments, the modified nucleotides are crosslinked after the reverse transcription. In some embodiments, the modified nucleotides are crosslinked during the reverse transcription. In some embodiments, the modified nucleotides are crosslinked to a high molecular weight molecule or complex, such as PEG or the like, which comprises functional groups that can react with the modified nucleotides. The high molecular weight molecule or complex can be added during the reverse transcription. After the cDNA molecules are crosslinked to the high molecular weight molecule or complex, diffusion can be made slower and/or sterically hindered.

In some embodiments, after the reverse transcription and crosslinking, the cDNA molecules can be targeted with different sets of probes for in situ detection. In some embodiments, the sets of probes comprise circularizable probes. In some embodiments, the cDNA molecules themselves can be circularized (e.g., through CircLigase™ or through selector probes in situ). In some embodiments, the circularized probes or the circularized cDNA can be amplified (e.g., using RCA) and the amplicons can be detected in situ.

In some embodiments, probes for in situ analysis can be gapfill circularizable probes that target more conserved regions in the V and J sequences and can be gapfilled to fill in the D sequence in order to identify the D region sequences. In some embodiments, gaps can be filled by polymerization, e.g., primer extension by a DNA polymerase using the 3' end of a circularizable probe as a primer and a cDNA comprising a VDJ join as a template. In some embodiments, gaps can be filled by splint ligation, using a diversity library of gapfill oligonucleotides that comprises numerous possible D sequence variants. In some embodiments, the library of oligonucleotides are incubated with the sample for hybridization to cDNA molecules comprising VDJ joins, allowing the best matching oligonucleotide to outcompete other oligonucleotides in the library and hybridize to the corresponding VDJ sequence. After washing the sample, the best matching oligonucleotides can be ligated into the gapfill circularizable probes and the circularized probes can be amplified.

In some embodiments, amplicons (e.g., RCA products) comprising V(D)J sequences or complements thereof are detected in situ using sequencing by synthesis (SBS), sequencing by ligation (SBL), sequencing by hybridization (SBH), or sequential hybridization of detectable probes. In some embodiments, the RCA products are sequentially contacted with pools of detectable probes, where each detectable probe comprises (i) a recognition sequence that comprises the same sequence as a corresponding gapfill oligonucleotide in the library of oligonucleotides used to circularize the gapfill circularizable probes and (ii) an overhang sequence for hybridization of a detectably labeled oligonucleotide. The diversity of the VDJ sequences, in particular the D sequences, can be analyzed using combinatorial decoding.

Methods, compositions, kits, and systems for performing the aforementioned in situ detection of V(D)J sequences are provided. In some embodiments, the present disclosure provides methods for high-throughput profiling of V(D)J transcripts in a large number of clonal T cell populations comprising TCRs with varying antigenic specificities. The methods and compositions disclosed herein may be used in research, diagnostics, and drug target discovery. Analyzing the spatial distribution of V(D)J transcripts in situ in various tissues could be used for development of therapeutic and/or prophylactic agents, e.g., TCR therapeutic treatment modalities and/or anti-disease vaccination.

II. Enrichment of V(D)J Sequences In Situ

A nucleic molecule comprising a V(D)J join sequence disclosed herein, e.g., a cDNA, can be a product of a TCR transcript. There are two subsets of T cells based on the exact pair of receptor chains expressed. These are either the alpha ($\alpha$) and beta ($\beta$) chain pair, or the gamma ($\gamma$) and delta ($\delta$) chain pair, identifying the $\alpha\beta$ or $\gamma\delta$ T cells, respectively. The expression of the $\beta$ and $\delta$ chain is limited to one chain in each of their respective subsets and this is referred to as allelic exclusion. These two chains are also characterized by the use of an additional DNA segment—the diversity (D) region—during the rearrangement process. The D region is flanked by N nucleotides which constitutes the NDN region of the CDR3 in these two chains. In some aspects, the CDR3 of each of the two receptor chains defines the T cell clonotype of cells expressing TCRs comprising the CDR3. For $\alpha\beta$ T cells the CDR3 is in most contact with the peptide bound to the MHC; as such, CDR3 sequences are generally a focus for analyzing immunological sequences. In some embodiments, the TCR transcript disclosed herein comprises a TCR$\alpha$ VJ join. In some embodiments, the TCR transcript disclosed herein comprises a TCR$\beta$ VDJ join. In some embodiments, the TCR transcript disclosed herein comprises a TCR$\gamma$ VJ join. In some embodiments, the TCR transcript disclosed herein comprises a TCR$\delta$ VDJ join.

A nucleic molecule comprising a V(D)J join sequence disclosed herein, e.g., a cDNA, can be a product of a BCR or immunoglobulin transcript. B cells are highly diverse, each expressing a practically unique BCR or immunoglobulin. There are approximately $10^{10}$-$10^{11}$ B cells in a human adult. Each B cell in an organism (e.g., human) expresses a different BCR that allows it to recognize a particular set of molecular patterns. Individual B cells gain this specificity during their development in the bone marrow, where they undergo a somatic rearrangement process that combines multiple germline-encoded gene segments to procures the BCR. Human BCR and antibody molecules are composed of heavy and light chains (each of which contains both constant (C) and variable (V) regions), which are encoded by genes on three loci: the immunoglobulin heavy locus IgH, containing the gene segments for the immunoglobulin heavy chain; the immunoglobulin kappa ($\kappa$) locus (Ig$\kappa$), containing the gene segments for the $\kappa$ light chain; and the immunoglobulin lambda ($\lambda$) locus (Ig $\lambda$), containing the gene segments for the $\lambda$ light chain. Each heavy chain and light chain gene contains multiple copies of three different types of gene segments for the variable regions of the antibody proteins. For example, the human immunoglobulin heavy chain region contains Constant (e.g., Cμ and Cδ) gene segments and 44 Variable (V) gene segments plus 27 Diversity (D) gene segments and 6 Joining (J) gene segments. The light chains also possess Constant (e.g., Cμ and Cδ) gene segments and numerous V and J gene segments, but do not have D gene segments. DNA rearrangement causes one copy of each type of gene segment to go in any given lymphocyte, generating an enormous antibody repertoire, although some are removed due to self-reactivity.

Because of the rearrangement undergone of the V(D)J segment in T cells and B cells, only parts of the V(D)J segments (the V, D, and J segments) can be traced back to segments encoded in highly repetitive regions of the germline that are not typically sequenced directly from the germ line DNA. Furthermore, the V, D, and J segments can be significantly modified during the V(D)J rearrangement process and through, in the case of B cells, somatic hypermutation (SHM). As such, there are typically no pre-existing full-length templates to align to sequence reads of the V(D)J segments of T cell receptors and B cell immunoglobulins. In some embodiments, clonal grouping or clonotyping can involve clustering the set of V(D)J sequences into clones, which are defined as a group of cells that are descended from a common ancestor. Unlike the case of T cells, members of a B cell clone may differ in their V(D)J sequences due to SHM.

In addition to V(D)J recombination and SHM, gene rearrangements editing the immunoglobulin (Ig) genes include class switch recombination (CSR). Like V(D)J recombination, CSR requires the formation of DNA double strand breaks (DSBs) as the key initiating step. Under physiological conditions, DSBs are introduced at the Ig genes by the activity of B lymphocyte cell specific enzymes such as recombinase activating gene 1/2 (RAG1/2, for V(D)J recombination) and activation-induced cytidine deaminase (AID, for CSR). During CSR, AID generates DSBs in the Ig locus by targeting repetitive sequences in the switch (S) regions that precede each Ig heavy (IgH) coding sequence. Paired DSBs in the switch regions are then joined by the classical and alternative non-homologous end joining (NHEJ) pathways to generate a switch of the IgH. This long range joining is thought to be part of a general mechanism of DNA repair where two DSBs are joined in cis over long chromosome distances.

In the immature B cell's antibody immunoglobulin (Ig) heavy chain (IgH) locus, the order of arrangement of the nucleic acid sequence encoding the heavy chain segments (order of the heavy chain exons) are as follows: for human, they are μ (for IgM), δ (for IgD), γ3 (for IgG3), γ1 (for IgG1), α1 (for IgA1), γ2 (for IgG2), γ4 (for IgG4), c (for IgE), and α2 (for IgA2); and for mouse, they are μ (for IgM), δ (for IgD), γ3 (for IgG3), γ1 (for IgG1), γ2b (for IgG2b), γ2a (for IgG2a), ε (for IgE), and α (for IgA). Class switching occurs after the activation of a mature B cell via its membrane-bound antibody molecule (BCRs) to generate the different classes of antibodies. Ligand or antigen binding to the cell surface BCR triggers an intracellular cell signaling process that brings about CSR and produces the various classes of antibodies. The various classes of antibodies all have the same variable domains as the original antibody generated in the immature B cell during the process of V(D)J recombination, but possessing distinct constant domains in their heavy chains.

In some embodiments, disclosed herein is a method involving detecting V(D)J transcripts in a biological sample.

In some embodiments, since the sensitivity and efficiency of V(D)J transcript detection can be limited by the available copy number of the antigen receptor transcripts of interest in the sample, a method disclosed herein comprises enriching nucleic acid molecules comprising V(D)J sequences or complements thereof. In some embodiments, V(D)J sequences include those in V(D)J transcripts comprising V(D)J joins. In some embodiments, V(D)J sequences include those s in cDNA generated from V(D)J transcripts comprising V(D)J joins. In some embodiments, V(D)J sequences include those in probes that hybridize to V(D)J transcripts or in probes that hybridize to cDNA of V(D)J transcripts. In some embodiments, V(D)J sequences include those in circularized probes generated during gapfill polymerization or gapfill oligonucleotide ligation. In some embodiments, V(D)J sequences include those in amplification products of V(D)J transcripts, amplification products of cDNA of V(D)J transcripts, or amplification products of the probes that hybridize to V(D)J transcripts or cDNA of V(D)J transcripts.

In some aspects, the copy number of antigen receptor transcripts of particular sequences in each immune cell is affected by the diverse nature of V(D)J sequences. Generally, the V(D)J transcripts are highly diverse in sequence in the 5' region, rendering efficient primer targeting and cDNA synthesis from the 3' poly(A) tail difficult. In some aspects, methods provided herein comprise enriching nucleic acid molecules comprising V(D)J sequences or complements thereof in situ. In some aspects, methods provided herein further comprise immobilizing the nucleic acid molecules in the sample to preserve the spatial distribution of the V(D)J transcripts in samples, such that the V(D)J sequences can be detected with high efficiency in situ. In some aspects, methods provided herein further comprise circularizing the nucleic acid molecules comprising V(D)J sequences, and/or circularizing circularizable probes or probe sets hybridized to the nucleic acid molecules. In some aspects, methods provided herein further comprise generating rolling circle amplification (RCA) products of the circularized nucleic acid molecules or probes. The circularized nucleic acid molecules or probes or products thereof (e.g., RCA products) can be detected for analyzing the spatial organization of V(D)J sequences in samples (e.g., tissues such as tumors comprising infiltrating immune cells). Such insights can be crucial to understanding disease development and establishing new treatment strategies.

In some embodiments, a primer disclosed herein (e.g., a primer that hybridizes to a 3' region of a V(D)J transcript) includes a sequence complementary to a region of a target nucleic acid sequence encoding a constant region of an antibody or a fragment thereof. In some embodiments, a primer disclosed herein comprises a sequence complementary to a region of a target nucleic acid sequence encoding a constant region of an immune cell receptor. In some embodiments, a primer disclosed herein includes a sequence complementary to a region of a target nucleic acid sequence encoding a constant region of a B cell receptor. In some embodiments, a primer disclosed herein includes a sequence complementary to a region of a target nucleic acid sequence encoding a constant region of a T cell receptor.

In some embodiments, a method disclosed herein comprises contacting a sample with one or more primers targeting a constant (C) region of an antigen receptor transcript for reverse transcription. In some embodiments, the sample is contacted with one or more primers targeting an IgH C region sequence, such as a sequence in Cμ, Cδ, Cγ3, Cγ1, Cα1, Cγ2, Cγ4, Cε, Cα2, or a combination thereof (for human), or a sequence in Cµ, Cδ, Cγ3, Cγ1, Cγ2b, Cγ2a, Cε, Cα, or a combination thereof (for mouse). In some embodiments, the sample is contacted with one or more primers targeting an Igκ C region sequence. In some embodiments, the sample is contacted with one or more primers targeting an Igλ, C region sequence. In some embodiments, the sample is contacted with one or more primers targeting a TCRα C region sequence, such as a sequence in Ca. In some embodiments, the sample is contacted with one or more primers targeting a TCRβ C region sequence, such as a sequence in Cβ1, Cβ2, or a combination thereof. In some embodiments, the sample is contacted with one or more primers targeting a TCRγ C region sequence. In some embodiments, the sample is contacted with one or more primers targeting a TCRδ C region sequence.

In some embodiments, the sample is contacted with one primer targeting the C region and the primer is extended by an enzyme having a reverse transcriptase activity, using the antigen receptor transcript as a template. In some embodiments, the sample is contacted with a plurality of primers targeting the C region and at least two or more or all of the primers are extended by an enzyme having a reverse transcriptase activity, using the antigen receptor transcript as a template. In some embodiments, a polymerase with strand displacement activity can be used to reverse transcribe the antigen receptor transcript from the multiple primers. In some embodiments, the plurality of primers comprises recognition sequences that are complementary to adjacent sequences in the C region of the antigen receptor transcript. In some embodiments, each of the plurality of primers is hybridized to a different sequence along the antigen receptor transcript, and the different sequences are not overlapping. In some embodiments, any two or more of the plurality of primers can hybridize to at least partially overlapping sequences in the antigen receptor transcript.

In some embodiments, the reverse transcription step comprises using at least two, at least three, at least four, at least five, or more primers that hybridize to a C region sequence in an antigen receptor transcript. In some embodiments, 5, 6, 7, 8, 9, 10, or more different primers can be tiled along the antigen receptor transcript.

A primer disclosed herein can be of any suitable length. Primers in the plurality of primers targeting the C region of the antigen receptor transcript can vary in length. For example, any one or more of the primers can be about 6 nucleotides to about 120 nucleotides, e.g., about 25 nucleotides in length. In some embodiments, a primer comprises a recognition sequence that hybridizes to a C region sequence or a portion thereof. In some embodiments, the recognition sequence of the primer is complementary to a portion of the C region of the antigen receptor transcript. In some embodiments, the recognition sequence of the primer is about 4, about 6, about 8, about 10, about 12, about 14, about 16, about 18, about 20, about 22, about 24, about 26, about 28, about 30, about 32, about 34, about 36, about 38, about 40, or more nucleotides in length. In some embodiments, two or more of the plurality of primers targeting the same C region can comprise recognition sequences of the same length. In some embodiments, two or more of the plurality of primers targeting the same C region can comprise recognition sequences of different lengths.

A primer disclosed herein can be of any suitable nucleotide composition. In some embodiments, one or more of the primers disclosed herein can include deoxyribonucleotides, ribonucleotides, and/or any synthetic or modified nucleotide residues that are capable of participating in Watson-Crick type or analogous base pair interactions. In some aspects, one or more of the primers are composed of DNA residues. In some aspects, one or more of the primers are chimeric DNA/RNA primers. In some aspects, one or more of the primers are ribonucleotide-modified DNA primers. For exemplary oligonucleotides that can be used as primers disclosed herein, see, e.g., Zhang et al., Chem Commun 2013 Nov. 4; 49(85):10013-5; U.S. Pat. No. 9,371,598; U.S. Patent Application Publication Nos. 2019/0367997 and 2018/0237864. In some embodiments, one or more of the primers disclosed herein can include one or more modified nucleic acids including but not limited to 2-aminopurine, 2,6-diaminopurine (2-amino-dA), inverted dT, 5-methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' fluoro bases (e.g., Fluoro C, Fluoro U, Fluoro A, and Fluoro G), or any combination of the foregoing. In some embodiments, one or more of the primers disclosed herein can comprise one or more functional groups (e.g., as part of a modified nucleotide residue) that can be linked to one another, other molecules (e.g., PEG comprising functional groups) in the sample, and/or a matrix embedding the sample. The deoxyribonucleotides, ribonucleotides, and/or synthetic or modified nucleotide residues described herein can be at any positions in the primer (e.g., in the recognition sequence that hybridizes to the antigen receptor transcript), as long as the primer can hybridize to the antigen receptor transcript and be extended by an enzyme comprising reverse transcriptase activity using the antigen receptor transcript as a template.

In some embodiments, one or more of the primers disclosed herein are specific to a C region sequence. Thus, in some examples, specific primers targeting the C region are contacted with the sample to allow specific hybridization to the C region, and unhybridized and/or nonspecifically hybridized primers can be removed from the sample, e.g., by washing the sample under stringent conditions.

In some embodiments, one or more of the primers disclosed herein can comprise a random sequence or a partially random sequence, e.g., at the 3' end of the primer which may hybridize to a J segment sequence or a portion thereof, a D segment sequence or a portion thereof, and/or a portion of a V segment sequence in an antigen receptor transcript. In some embodiments, one or more of the primers disclosed herein can comprise a random sequence with a higher GC content, a partial random sequence with fixed G or C at specific positions, the use of guanosines, the use of locked nucleic acids, or any combination thereof. In some embodiments, the random sequence includes a random hexamer. In some embodiments, the random sequence includes a random decamer.

In some embodiments, one or more of the primers disclosed herein can be provided as a single oligonucleotide molecule. In some embodiments, one or more of the primers disclosed herein can be provided in two or more molecules, which can be connected to one another to form a single probe molecule, for example, upon hybridization of the two or more molecules to an antigen receptor transcript. In some embodiments, the two or more molecules are ligated using the antigen receptor transcript as a template, with or without gap filling prior to the ligation. Exemplary RNA-templated ligation methods include those disclosed in US 2018/0208967A1 and US 2020/0224244A1 which are hereby incorporated by reference in their entirety.

In some aspects, one or more of the primers disclosed herein are single stranded. In some aspects, one or more of the primers disclosed herein are partially double stranded, for example, at the 5' of the recognition sequence of the primer. In some aspects, one or more of the primers disclosed herein comprise a 5' overhang upon hybridization to the antigen receptor transcript. In some embodiments, the 5' overhang is about 2, about 4, about 6, about 8, about 10, about 12, about 14, about 16, or more nucleotides in length. In some embodiments, the 5' overhang comprises deoxyribonucleotides, ribonucleotides, and/or any synthetic or modified nucleotide residues described herein. In some embodiments, the 5' overhang comprises one or more functional groups (e.g., as part of a modified nucleotide residue) that can be linked to one another, other molecules (e.g., PEG comprising functional groups) in the sample, and/or a matrix embedding the sample.

Figure 1:
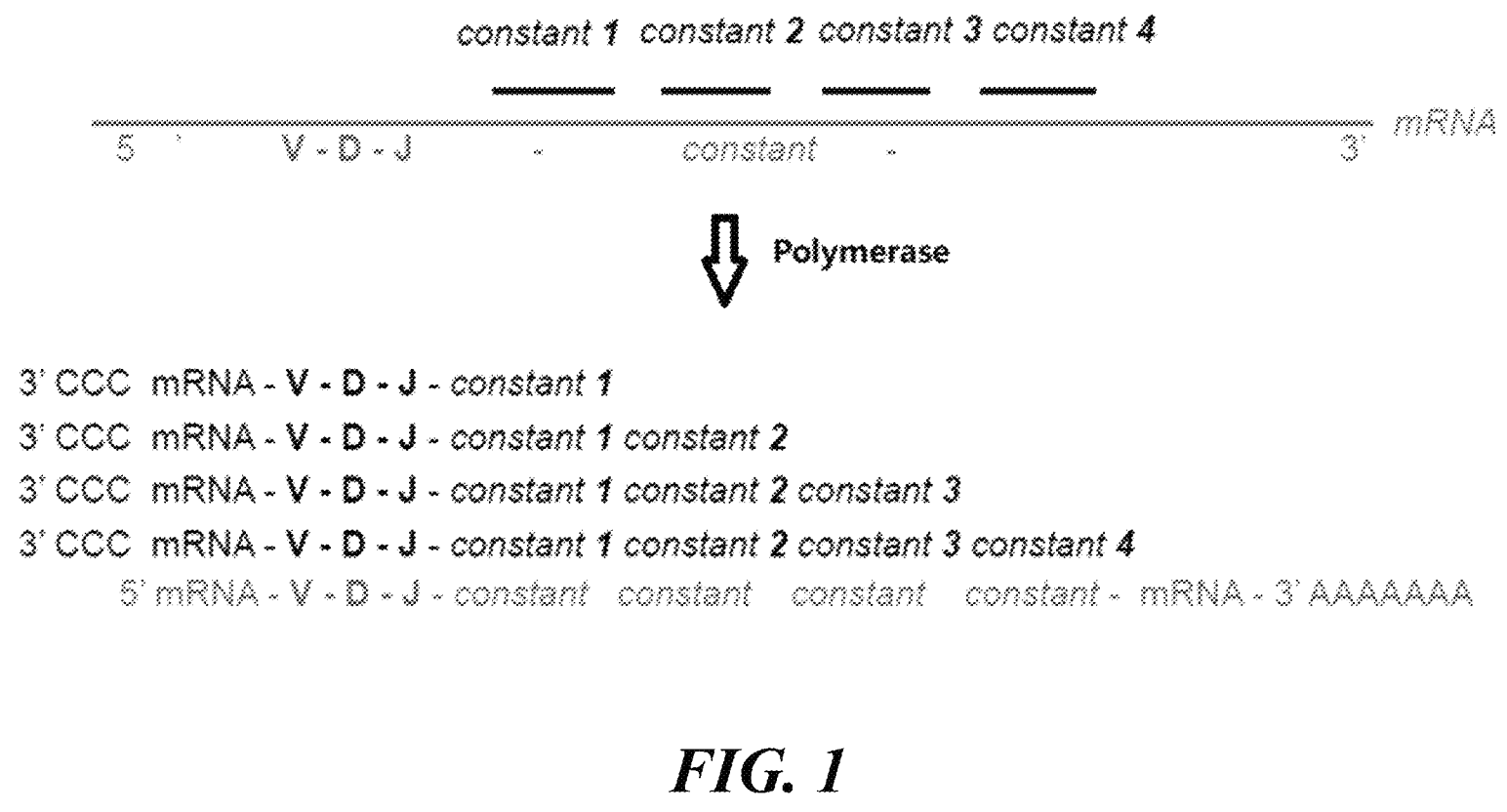

As exemplified by FIG. 1, primers targeting adjacent sequences of the constant region of a VDJ transcript are contacted with a sample, and upon hybridization to the VDJ transcript, any one or more of the primers can each comprise a 5' overhang (not shown in the figure). The adjacent sequences can be non-overlapping with one another, or any two adjacent sequences can be partially overlapping with each another. The primers may be extended by an enzyme having a reverse transcriptase activity and a strand displacement activity. For example, the constant 4 region primer can hybridize to the VDJ transcript and be extended by the enzyme to produce a cDNA molecule as the primer extension product comprising sequences complementary to constant 4, constant 3, constant 2, constant 1, and the VDJ join. Likewise, the constant 3 region primer can produce a cDNA molecule comprising sequences complementary to constant 3, constant 2, constant 1, and the VDJ join; the constant 2 region primer can produce a cDNA molecule comprising sequences complementary to constant 2, constant 1, and the VDJ join; and the constant 1 region primer can produce a cDNA molecule comprising sequences complementary to constant 1 and the VDJ join. Since the enzyme also has a strand displacement activity, the cDNA molecules generated by the enzyme (e.g., from the constant 1 region primer, the constant 2 region primer, the constant 3 region primer, and/or the constant 4 region primer) can be displaced from the antigen receptor transcript, allowing additional molecules of the primers to hybridize to the antigen receptor transcript and be extended to generate more cDNA molecules. Thus, in some aspects, the extension of a 5' primer by reverse transcription can displace a cDNA product of one or more 3' primers hybridized to the antigen receptor transcript. The reverse transcription and cDNA displacement can be repeated multiple times to enrich nucleic acid molecules (e.g., cDNA) that comprise complements of the VDJ sequence of the antigen receptor transcript.

The desired reverse transcriptase activity can be provided by one or more enzymes including a reverse transcriptase, suitable examples of which include, but are not limited to: M-MLV reverse transcriptase, MuLV reverse transcriptase, AMV reverse transcriptase, HIV reverse transcriptase (e.g., HIV-1 reverse transcriptase), ArrayScript™ enzyme, Multi-Scribe™ enzyme, ThermoScript™ enzyme, and Super-Script® I, II, III, and IV enzymes. "Reverse transcriptase" includes not only naturally occurring enzymes, but all such modified derivatives thereof, including also derivatives of naturally-occurring reverse transcriptase enzymes.

In addition, reverse transcription can be performed using sequence-modified derivatives or mutants of M-MLV, MuLV, AMV, and HIV reverse transcriptase enzymes, including mutants that retain at least some of the functional, e.g. reverse transcriptase, activity of the wild-type sequence. The reverse transcriptase enzyme can be provided as part of a composition that includes other components, e.g. stabilizing components that enhance or improve the activity of the reverse transcriptase enzyme, such as RNase inhibitor(s), inhibitors of DNA-dependent DNA synthesis, e.g., actinomycin D. Many sequence-modified derivative or mutants of reverse transcriptase enzymes, e.g., M-MLV, and compositions including unmodified and modified enzymes are commercially available, e.g., ArrayScript™, MultiScribe™, ThermoScript™, and SuperScript® I, II, III, and IV enzymes.

Certain reverse transcriptase enzymes (e.g., Avian Myeloblastosis Virus (AMV) Reverse Transcriptase and Moloney Murine Leukemia Virus (M-MuLV, MMLV) Reverse Transcriptase) can synthesize a complementary DNA strand using both RNA (cDNA synthesis) and single-stranded DNA (ssDNA) as a template. Thus, in some embodiments, the reverse transcription reaction can use an enzyme (reverse transcriptase) that is capable of using both RNA and ssDNA as the template for an extension reaction, e.g., an AMV or MMLV reverse transcriptase.

In some embodiments, enzymes including reverse transcriptases disclosed herein can have a strand displacement activity. In some embodiments, a reverse transcriptase disclosed herein catalyzes polymerization of DNA on an RNA template, with an ability to displace a non-template strand concomitantly with polymerization.

In some embodiments, the desired reverse transcriptase activity and strand displacement activity can be provided by one or more enzymes including DNA polymerases. In some embodiment, a DNA polymerase disclosed herein has the ability to displace downstream nucleic acid (e.g., DNA) encountered during polymerization, as well as the ability to reverse transcribe an RNA such as an antigen receptor transcript. Exemplary strand-displacing DNA polymerases with reverse transcriptase activities include but are not limited to phi29 DNA polymerase, Bst DNA polymerase (e.g., Bst DNA Polymerase, Large Fragment), Bsm DNA polymerase, and BcaBEST DNA polymerase. In some embodiments, an enzyme disclosed herein can be engineered to provide the desired reverse transcriptase activity and strand displacement activity. For instance, while Taq DNA polymerase has been known to degrade an encountered downstream strand via a 5→3" exonuclease activity instead of strand displacement of the downstream strand, a gain of function mutant (Taq D732N DNA polymerase) has been shown to have strand-displacement ability and reverse transcriptase activity. See, e.g., Barnes et al., Front. Bioeng. Biotechnol. (2021) 8; doi: 10.3389/fbioe.2020.553474, incorporated herein by reference in its entirety.

In some embodiments, an enzyme having the ability to reverse transcribe an RNA such as an antigen receptor transcript is a high processivity polymerase, e.g., a high processivity reverse transcriptase or a high processivity DNA polymerase with reverse transcriptase activity. In some embodiments, the processivity of a polymerase can be measured by the average number of nucleotides incorporated in a single binding event (e.g., a single association/disassociation event) of the enzyme to a template, and polymerases having higher processivity can synthesize longer cDNA strands in a shorter reaction time. In some embodiments, a polymerase disclosed herein is capable of incorporating at least about 100, at least about 250, at least about 500, at least about 750, at least about 1,000, at least about 1,250, at least about 1,500, at least about 1,750, at least about 2,000, at least about 2,500, at least about 3,000, at least about 4,000, at least about 5,000, at least about 10,000, at least about 20,000, at least about 30,000, at least about 40,000, at least about 50,000, or more nucleotides in a single binding event before dissociating from a template strand (e.g., an antigen receptor transcript). In some embodiments, a polymerase disclosed herein is capable of incorporating at least about 100, at least about 200, at least about 300, at least about 400, at least about 500, at least about 600, at least about 700, at least about 800, at least about 900, at least about 1,000, at least about 1,250, at least about 1,500, at least about 1,750, at least about 2,000, or more nucleotides per second. In some embodiments, a polymerase disclosed herein can be engineered to provide a desired reverse transcriptase processivity and/or speed of nucleotide incorporation.

In some embodiments, an enzyme having the ability to reverse transcribe an RNA such as an antigen receptor transcript has a low error rate and high fidelity. In some embodiments, a polymerase disclosed herein has an error rate of no more than one error in more than or about 500,000, more than or about 450,000, more than or about 400,000, more than or about 350,000, more than or about 300,000, more than or about 250,000, more than or about 200,000, more than or about 150,000, more than or about 100,000, more than or about 90,000, more than or about 80,000, more than or about 70,000, more than or about 60,000, more than or about 50,000, more than or about 40,000, more than or about 30,000, more than or about 20,000, more than or about 15,000, or more than or about 10,000 nucleotides incorporated.

In some embodiments, a polymerase disclosed herein exhibits a reverse transcriptase activity and optionally a strand displacement activity at a temperature between about 4° C. and about 8° C., between about 8° C. and about 12° C., between about 12° C. and about 16° C., between about 16° C. and about 20° C., between about 20° C. and about 24° C., between about 24° C. and about 28° C., between about 28° C. and about 32° C., between about 32° C. and about 36° C., between about 36° C. and about 40° C., between about 40° C. and about 44° C., between about 44° C. and about 48° C., between about 48° C. and about 52° C., between about 52° C. and about 56° C., between about 56° C. and about 60° C., or higher than 60° C., such as at 65° C. In some embodiments, the ability of a reverse transcriptase to withstand high temperatures is useful, since elevated reaction temperatures may help denature RNA with strong secondary structures and/or high GC content, allowing polymerases to read through the sequence. In some embodiments, reverse transcription at higher temperatures enhances specificity of a primer's binding to a template (e.g., an antigen receptor transcript). In some embodiments, reverse transcription at higher temperatures enables synthesis of longer cDNA molecules (e.g., full-length cDNA synthesis of a transcript) and higher yields, which may lead to better representation of an RNA population by the cDNA molecules. In some embodiments, a polymerase disclosed herein can be engineered to withstand a higher temperature while the enzyme remains stable and retains a reverse transcriptase activity and optionally a strand displacement activity.

In some embodiments, a polymerase disclosed herein exhibits a reverse transcriptase activity and optionally a strand displacement activity even in the presence of an inhibitor that may be present in the sample. Examples of reverse transcriptase inhibitors include heparin and bile salts from blood and stool, humic acid and polyphenols, and formalin and paraffin from formalin-fixed, paraffin-embedded (FFPE) samples. These inhibitors may bind to RNA and/or reduce polymerization activity, and in some embodiments, a polymerase disclosed herein (e.g., highly processive reverse transcriptases) is capable of overcoming such inhibition.

In some embodiments, a polymerase (e.g., a reverse transcriptase having no or limited strand displacement activity) and a helicase can be used, where the polymerase can extend a primer to generate a cDNA product and the helicase can unwind the cDNA product from an RNA template (e.g., a V(D)J transcript). In some embodiments, a polymerase having a strand displacement activity can be used in conjunction with a helicase, where the helicase can unwind the cDNA product from the RNA template. In some embodiments, unwinding and/or displacement of the cDNA product from the template allows additional molecules of one or more primers to bind the V(D)J transcript and prime reverse transcription to generate additional cDNA molecules comprising V(D)J sequences.

In some embodiments, the reverse transcriptase has strand displacement activity. In some embodiments, the strand displacement activity of the reverse transcriptase displaces one or more primers of the plurality of primers from the target nucleic acid (e.g., a V(D)J transcript). In some embodiments, the strand displacement activity of the reverse transcriptase displaces the one or more extension products from the target nucleic acid.

In some embodiments, extension is performed using a reverse transcriptase and a helicase. In some embodiments, the method includes use of one or more single-stranded DNA binding proteins. In some embodiments, the one or more single-stranded DNA binding proteins includes one or more of: Tth RecA, E. coli RecA, T4 gp32 and ET-SSB. In some embodiments, the helicase has stand displacement activity. In some embodiments, extension is performed using a superhelicase and a reverse transcriptase. In some embodiments, the superhelicase is selected from the group consisting of: Rep, PrcA, UvrB, RecBCD, and Tte-Uvrd. In some embodiments, the superhelicase has strand displacement activity.

FIG. 2 shows an exemplary approach of generating copies of nucleic acids comprising V(D)J sequences using a polymerase (e.g., a reverse transcriptase) in the presence of an enzyme with or having a helicase activity (e.g., a helicase) having a strand displacement activity. In some examples, constant 2 and constant 1 are adjacent sequences in the antigen receptor transcript constant region which are non-overlapping with one another. In some examples, constant 2 and constant 1 can be partially overlapping with one another. Any one or both primers can comprise a 5' overhang (not shown in the figure) upon hybridization to constant 2 or constant 1. Multiple cDNA molecules from the same primer may be generated, and each cDNA molecule can comprise a complement of the V(D)J sequence in the transcript. Moreover, the cDNA products of the particular primer (e.g., a primer that binds to constant 1) can be displaced by primer extension from one or more 5' primers (e.g., a primer that binds to constant 2) targeting the constant region. Likewise, primer extension from the particular primer can displace cDNA products of one or more 3' primers targeting the constant region. In some embodiments, each of the cDNA products of the 3' primer(s), the particular primer, and the 5' primer(s) can comprise a complement of the V(D)J sequence in the transcript, thereby enriching cDNA molecules that can be detected in situ in order to detect the V(D)J sequence in the transcript.

In some embodiments, reverse transcription of target nucleic acids is performed with a plurality of primers. In some examples, reverse transcription is performed using a reverse transcriptase with strand displacement activity. In some examples, reverse transcription is performed with a reverse transcriptase and a helicase. In some examples, reverse transcription is performed with a reverse transcriptase and a superhelicase. In some examples, reverse transcription is performed with one or more single-stranded DNA binding proteins.

An enzyme with or having a helicase activity can be any enzyme capable of unwinding a double stranded nucleic acid, such as a DNA/RNA duplex. In some embodiments, the enzyme functions to unwind double stranded nucleic acids, thus obviating the need for repeated melting cycles. Exemplary enzymes capable of unwinding a double stranded nucleic acid include but are not limited to *E. coli* helicase I, II, III, and IV, Rep, DnaB, PriA, PcrA, T4 Gp41 helicase, T4 Dda helicase, T7 Gp4 helicases, SV40 Large T antigen, yeast RAD, RecQ helicase, thermostable UvrD helicases from *T. tengcongensis* and *T. thermophilus*, thermostable DnaB helicase from *T. aquaticus*, and MCM helicase from archaeal and eukaryotic organisms. Additional exemplary helicases may be, or may be derived from, a RecD helicase, such as a Hel308 helicase, a TraI helicase, or a Twc helicase, an XPD helicase, or a Dda helicase. The helicase may be Hel308 Mbu, Hel308 Csy Hel308 Tga, Hel308 Mhu, TraI Eco, XPD Mbu, or a mutant or a derivative thereof. Exemplary enzymes include but are not limited to those described in U.S. Pat. Nos. 9,617,591; 9,758,823; 9,797,009; 10,385,382; 10,724,018; 10,808,231; 11,155,860; 11,180,741; and US 2019/0352709, all of which are incorporated herein by reference in their entirety.

In some embodiments, an enzyme with or having a helicase activity can be an ATP-dependent helicase. In some embodiments, an enzyme with or having a helicase activity can be an RNA helicase. In some embodiments, an enzyme with or having a helicase activity can be a DNA helicase. In some embodiments, an enzyme with or having a helicase activity can be an active helicase. In some embodiments, an enzyme with or having a helicase activity can be a passive helicase.

Figures 3, 4A:
FIG. 3 shows that several cDNA products from the same primer binding site may be generated and displaced by a strand displacing polymerase and/or a helicase.
FIG. 4A shows that cDNA products from the plurality of primers are crosslinked (indicated by "X") to one another, to other molecules in the sample, and/or to a matrix embedding the sample, thereby preventing the cDNA products from diffusing away from the antigen receptor transcript. Detectable V(D)J sequences are enriched, and circularizable probes may be used for in situ detection.

FIG. 3 shows an example of the extension product of a 5' primer displacing a 3' primer and its extension product from an antigen receptor transcript. In various embodiments, a primer binding site in the constant region can undergoes repeated cycles of primer hybridization and reverse transcription primed by the primer, thereby generating multiple cDNA molecules from the primer binding site. In some embodiments, the primer binding site is 3' to one or more other primer binding sites. In some embodiments, the multiple cDNA molecules comprising V(D)J sequences may be covalently or non-covalently linked to one or more molecules at the location of the antigen receptor transcript in the sample, such as to the antigen receptor transcript, to other cDNA molecules at the location, to a cellular or synthetic matrix, and/or to other molecules such as nucleic acids and/or proteins at the location of the sample.

In some embodiments, at least 2, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 200, at least 300, at least 400, at least 500, at least 1,000, at least 5,000, or more than 5,000 cDNA molecules comprising complements of a V(D)J sequence or a portion there of (e.g., a portion comprising the D segment sequence) are generated from an antigen receptor transcript comprising the V(D)J sequence. The cDNA molecules can be generated using any one or more or all of the plurality of primers targeting the C region of the antigen receptor transcript. In some embodiments, at least some or all of the cDNA molecules comprise complements of the J segment sequence or a portion thereof of the antigen receptor transcript. In some embodiments, at least some or all of the cDNA molecules comprise complements of the D segment sequence or a portion thereof of the antigen receptor transcript. In some embodiments, at least some or all of the cDNA molecules comprise complements of the V segment sequence or a portion thereof of the antigen receptor transcript. In some embodiments, at least some or all of the cDNA molecules comprise a 3' poly(C) sequence, such as 3' CCC, as shown in FIG. 1 and FIG. 2.

In some embodiments, at least some or all of the cDNA molecules can be used as templates for polymerization, e.g., using one, two, or more PCR primers. In some embodiments, the antigen receptor transcript comprises a sequence 5' to the V segment, and one or more cDNA products of the antigen receptor transcript can comprise a sequence complementary to the sequence 5' to the V segment. In some embodiments, the sequence 5' to the V segment comprises an L (leader) sequence and/or an adaptor sequence. In some embodiments, an adaptor sequence is introduced upstream (5') of transcript V segments prior to reverse transcription (e.g., by RNA ligation) or concordant with reverse transcription (e.g., by template switch). In some embodiments, the adaptor is a common adaptor introduced to two or more different antigen receptor transcripts in a sample. In some embodiments, two or more common adaptors are contacted with the sample, and subsets of antigen receptor transcripts in the sample can be tagged with different adaptors. In some embodiments, the adaptor sequence is an invariable sequence ligated to the 5' end of the V segment in the antigen receptor transcript. In some embodiments, the adaptor sequence is a universal adaptor. In some embodiments, the antigen receptor transcript is reverse transcribed to generate a cDNA molecule comprising 3' poly-C, and a template switching oligonucleotide comprising an adaptor sequence and 3' poly-G is hybridized to the cDNA molecule to introduce a complement of the adaptor sequence into the cDNA molecule. In some embodiments, the antigen receptor transcript is reverse transcribed to generate a sequence complementary to an adaptor sequence ligated to 5' to the V segment using RNA ligation. In either case, the adaptor sequence can be used as a primer to amplify the cDNA, for example, using a DNA polymerase described here. In some embodiments, a complement strand of the cDNA can be unwound from the cDNA template, for example, using a helicase described here, in order to generate a single-stranded nucleic acid for subsequent in situ detection. Exemplary methods for PCR reactions include but are not limited to those described in Calis and Rosenberg, Trends Immunol. (2014) 35(12): 581-590, incorporated herein by reference in its entirety.

III. Immobilization of Nucleic Acid Molecules

In some embodiments, the generation of multiple cDNA molecules (or amplification products of the cDNA molecules) comprising the V(D)J sequence in an antigen receptor transcript enriches nucleic acid molecules that can be detected in situ in order to detect the V(D)J sequence. In some embodiments, the nucleic acid molecules (e.g., cDNA or amplification products thereof) generated from antigen receptor transcripts in a sample are kept in place and prevented from diffusing away from the corresponding antigen receptor transcript at a location in a biological sample. In some embodiments, the methods provided herein comprise immobilization of the nucleic acid comprising a V(D)J sequence to the location in the biological sample. The extension products of the primers (e.g., cDNA molecules comprising V(D)J sequences) and/or RCA products (e.g., as described in Section V) may be immobilized by covalently or non-covalently linking an extension product and/or an RCA product to one or more molecules at the location. In some embodiments, the one or more molecules are endogenous in the biological sample.

In some embodiments, the one or more molecules are in a matrix in or embedding the biological sample, thus the nucleic acid molecules are attached to molecules of the matrix at the location of an antigen receptor transcript, thereby enriching detectable V(D)J sequences at the location. The products of the primers (e.g., cDNA molecules comprising V(D)J sequences) may be immobilized within the matrix by covalent or noncovalent bonding, e.g., by crosslinking mediated by reactions between functional groups. In some embodiments, the extension products of the primers comprise functional groups capable of reacting with each other and/or with functional groups in the one or more molecules, e.g., endogenous molecules in the biological sample or a matrix in or embedding the biological sample. In some embodiments, the extension products of the primers comprise one or more modified nucleotides each comprising one or more functional groups. In some aspects, various molecules (e.g., endogenous molecules, primers, probes, and/or generated products) can be immobilized using a combination of various suitable functional groups.

In some embodiments, modified nucleotides are incorporated into the extension products (e.g., cDNA) of the one or more primers during reverse transcription and/or during amplification of the cDNA, and functional groups in the modified nucleotides are capable of reacting with each other and/or with functional groups in a cellular matrix and/or a polymeric matrix in or embedding the biological sample. In some embodiments, a modified nucleotide, such as an amine-modified nucleotide, can be incorporated into the cDNA products of an antigen receptor transcript and/or amplification products of the cDNA molecules. Exemplary amine-modified nucleotides include but are not limited to a 5-Aminoallyl-dUTP moiety modification, a 5-Propargylamino-dCTP moiety modification, a $N^6$-6-Aminohexyl-dATP moiety modification, or a 7-Deaza-7-Propargylamino-dATP moiety modification. In some embodiments, amine-modified nucleotides such as aminoallyl-dUTP residues incorporated into a cDNA or amplification product can be subsequently coupled to an N-hydroxysuccinimide (NHS) derivatized molecule. In some embodiments, the nucleic acid molecules (e.g., cDNA) comprising amine-modified nucleotides can be crosslinked to one another and/or to other molecules in the biological sample using a crosslinker, such as BS(PEG)$_9$ which is a bis-succinimide ester-activated PEG compound for crosslinking between primary amines (NH$_2$) in proteins (such as in lysine residues) and/or in a matrix (e.g., a polymer matrix such as a hydrogel) and in the amine-modified nucleotides. Other exemplary crosslinkers include N-hydroxysuccinimide ester of acrylic acid (ANHS) which reacts with amine groups in proteins (such as in lysine residues) and/or in a matrix (e.g., a polymer matrix such as a hydrogel) and in the amine-modified nucleotides.

In some embodiments, functional groups in the cDNA or amplification products thereof (e.g., in modified nucleotides incorporated into cDNA via reverse transcription) can be reacted with other functional groups, for example, via condensation of amines and activated carboxylic esters (e.g., N-hydroxysuccinimide esters); condensation of amine and aldehydes under reductive amination conditions; and cycloaddition reactions such as the Diels-Alder [4+2] reaction, 1,3-dipolar cycloaddition reactions, and [2+2] cycloaddition reactions. In some embodiments, an azide modified nucleotide and/or an alkyne modified nucleotide can be incorporated into cDNA via reverse transcription, and azide functional groups and/or alkyne functional groups can be provided in other molecules in the sample (e.g., proteins in the sample), a matrix (e.g., a polymer matrix such as a hydrogel), and/or a crosslinking reagent. In some embodiments, the cDNA or amplification products thereof may be functionalized by adding nucleotide triphosphate analogs comprising functional moieties for immobilization. In some examples, the nucleotide triphosphate analogs include, but are not limited to, amino-allyl dUTP, 5-TCO-PEG4-dUTP, C8-Alkyne-dUTP, 5-Azidomethyl-dUTP, 5-Vinyl-dUTP, 5-Ethynyl dUTP, and other nucleotide triphosphate analogs comprising a functional group for immobilization by crosslinking, or forming a chemical bond between the molecule and other molecules in the sample (e.g., proteins in the sample), a matrix (e.g., a polymer matrix such as a hydrogel), and/or a crosslinking reagent.

In some embodiments, a crosslinking reagent can be used to link functional groups in the cDNA or amplification products thereof to functional groups in the cDNA or amplification products thereof or other molecules in the sample or a matrix. In some embodiments, the crosslinking reagent is a multivalent (e.g., bivalent or trivalent) reagent comprising functional groups selected from the group consisting of a thiol, epoxide, amine, alcohol, hydrazide, hydroxylamine, and isocyanate.

In some embodiments, functional groups in the cDNA or amplification products thereof (e.g., in modified nucleotides incorporated into cDNA via reverse transcription) can include functional groups for click chemistry reactions, including [3+2] cycloaddition reactions (e.g., Huisgen 1,3-dipolar cycloaddition reaction and copper(I)-catalyzed azide-alkyne cycloaddition (CuAAC)); thiol-ene reactions; the Diels-Alder reaction and inverse electron demand Diels-Alder reaction; [4+1] cycloaddition of isonitriles and tetrazines; and nucleophilic ring-opening of small carbocycles (e.g., epoxide opening with amino oligonucleotides). In some embodiments, functional groups in modified nucleotides can include, for example, maleimides and thiols; and para-nitrophenyl ester-functionalized oligonucleotides and polylysine-functionalized substrate. In some embodiments, functional groups in modified nucleotides can include functional groups for disulfide reactions; radical reactions (see, e.g., U.S. Pat. No. 5,919,626, the entire contents of which are herein incorporated by reference); and reactions involving hydrazide functional groups and aldehyde functional groups (see, e.g., Yershov et al. (1996) Proc. Natl. Acad. Sci. USA 93, 4913-4918, the entire contents of which are herein incorporated by reference).

Functional groups that react with functional groups in the cDNA or amplification products thereof can be provided in other molecules in the sample (e.g., proteins in the sample), a matrix (e.g., a polymer matrix such as a hydrogel), and/or one or more crosslinking reagents. In some embodiments, the functional groups that participate in the click reactions between the cDNA or amplification products thereof and other molecules in the sample or a matrix and optionally one or more crosslinking reagents may comprise, but are not limited to, azido/alkynyl; azido/cyclooctynyl; tetrazine/dienophile; thiol/alkynyl; cyano/1,2-amino thiol; and, nitrone/cyclooctynyl.

In some embodiments, modified nucleotides incorporated into the cDNA or amplification products thereof can comprise binding moieties for non-covalent binding. Methods for non-covalent binding include, for example, using biotin-functionalized nucleotides and streptavidin-functionalized molecules. In some embodiments, binding moieties for non-covalent binding can include, but are not limited to, biotin, antibody epitopes, His-tags, streptavidin, avidin, strep-tactin, polyhistidine, peptides, haptens and metal ion chelates etc. Exemplary pairs of binding moieties for non-covalent binding include, but are not limited to, biotin/streptavidin, biotin/avidin, biotin/neutravidin, biotin/strep-tactin, poly-His/metal ion chelate, peptide/antibody, glutathione-S-transferase/glutathione, epitope/antibody, maltose binding protein/amylase, and maltose binding protein/maltose.

In some embodiments, modified nucleotides are spiked in the reverse transcription reaction and/or amplification of cDNA molecules. In some embodiments, modified nucleotides account for between about 0.1% and about 90% of total nucleotides added to the sample for reverse transcription and/or amplification of cDNA. In some embodiments, modified nucleotides account for between about 1% and about 2%, between about 2% and about 4%, between about 4% and about 6%, between about 6% and about 8%, between about 8% and about 10%, between about 12% and about 14%, between about 14% and about 16%, between about 16% and about 18%, or between about 18% and about 20% of total nucleotides provided for the reverse transcription reaction and/or amplification of cDNA. In some embodiments, modified nucleotides account for 20%, 30%, 40%, 50%, 60%, or more of total nucleotides provided for the reverse transcription reaction and/or amplification of cDNA.

In some embodiments, the modified nucleotides, once incorporated into nucleic acid molecules, are crosslinked to each other and/or to other molecules. In some embodiments, the modified nucleotides are crosslinked after the reverse transcription and/or amplification of cDNA. In some embodiments, the modified nucleotides are crosslinked during the reverse transcription and/or amplification of cDNA.

In some embodiments, the modified nucleotides are cross-linked to a high molecular weight molecule or complex, such as PEG or the like, which comprises functional groups that can react with the modified nucleotides. The high molecular weight molecule or complex can be added during the reverse transcription. The nucleic acid molecules (e.g., cDNA) can be crosslinked to a macromolecule (such as a high molecular weight PEG) or complex thereof to slow down diffusion rate of the nucleic acid molecules.

In some embodiments, reverse transcription from the primers and/or amplification of cDNA is allowed to proceed slowly and/for a short time, thereby limiting the number of nucleic acid product molecules that can branch off and diffuse, followed by fixing and/or crosslinking the sample to keep the nucleic acid products in place. In some embodiments, reverse transcription from the primers and/or amplification of cDNA is allowed to proceed for no more than 10 minutes, no more than 30 minutes, no more than 1 hour, no more than 2 hours, no more than 3 hours, no more than 6 hours, or no more than 12 hours, thereby limiting diffusion of the nucleic acid product molecules from the template antigen receptor transcript or cDNA. In some embodiments, reverse transcription from the primers and/or amplification of cDNA is allowed to proceed at a temperature of about 4° C., about 8° C., about 12° C., about 16° C., about 20° C., about 24° C., about 28° C., about 32° C., or about 36° C., or in a range between any of the aforementioned temperatures, thereby limiting diffusion of the nucleic acid product molecules from the template antigen receptor transcript or cDNA.

Immobilization of the nucleic acid molecules provide benefits. For instance, by cross-linking the nucleic acid molecules such as cDNA molecules to each other and/or other molecules at the location of the template, the spatial relationship between the nucleic acid molecules and the antigen receptor transcript in the sample can be maintained. By being immobilized, such as by covalent bonding or cross-linking, the nucleic acid molecules are resistant to movement or unraveling under mechanical stress, for example, during circularizable probe hybridization, probe ligation, RCA of circularized probes, and one or more washing steps in between. Likewise, as detailed in Section V, RCA products can be immobilized, such as by covalent bonding or cross-linking, in order to resist movement during sequential probe hybridization and unhybridization (e.g., by stripping) cycles during in situ detection, e.g., as described in Section VI.

In some aspects, the extension products of the primers (e.g., cDNAs comprising V(D)J sequences) are copolymerized and/or covalently attached to a surrounding natural matrix or synthetic matrix, thereby preserving their spatial relationship and any information inherent thereto. In some embodiments, the matrix is a cellular matrix. In some embodiments, the matrix is a polymeric matrix. The matrix may be in or embedding the biological sample.

In some aspects, the cDNA or amplification products thereof can be crosslinked to a polymer matrix. For example, the polymer matrix can be a hydrogel. In some embodiments, the cDNA or amplification products thereof comprise functional groups that can react with functional groups in the polymer matrix. In some embodiments, the cDNA or amplification products thereof comprise functional groups that can react with functional groups in one or more molecules (e.g., a crosslinking reagent, an oligonucleotide, etc.) which in turn react with and/or bind to the polymer matrix. In some embodiments, one or more oligonucleotides probe(s) can be modified to contain functional groups that can be used as an anchoring site to attach the cDNA or amplification products thereof to a polymer matrix.

Exemplary modifications and polymer matrix that can be employed in accordance with the provided embodiments comprise those described in, for example, US 2016/0024555, US 2018/0251833, US 2016/0024555, US 2018/0251833, US 2017/0219465, and US 2020/0071751, each of which is herein incorporated by reference in its entirety. In some examples, the polymer matrix comprises a scaffold having modifications or functional groups that can react with and/or bind to the modifications or functional groups of the cDNA or amplification products thereof. In some examples, the scaffold can comprise oligonucleotides, polymers or chemical groups, to provide a matrix and/or support structures.

In some embodiments, the matrix comprises one or more types of functional groups, wherein the functional groups can react with the functional groups of the cDNA or amplification products thereof, thereby immobilizing the cDNA or amplification products thereof. For example, amino-allyl dUTP in the cDNA or amplification products thereof may be cross-linked to endogenous free amine groups present in proteins and other biomolecules present within the endogenous or exogenous cellular matrix, or present in a modified synthetic hydrogel matrix, such as an amine-functionalized polyacrylamide hydrogel formed by copolymerization of polyacrylamide and N-(3-aminopropyl)-methacrylamide. In some cases, azide functional moieties in the cDNA or amplification products thereof may be cross-linked to a synthetic hydrogel matrix comprising alkyne functional moieties, such as that formed by copolymerization of acrylamide and propargyl acrylamide. In some cases, the cDNA or amplification products thereof may be tethered via a click reaction to a click reactive group functionalized hydrogel matrix (e.g., click gel). For example, 5-azidomethyl-dUTP can be incorporated into the cDNA or amplification products thereof and then immobilized to the hydrogel matrix functionalized with alkyne groups. Various click reactions may be used. In some embodiments, the tethering comprise providing conditions and buffer suitable for catalyzing the functional immobilization linkage between the cDNA and/or amplification products thereof and the matrix. Crosslinking reagents comprising one or more click functional groups can be used to react with the cDNA or amplification products thereof and the matrix, thereby tethering the cDNA or amplification products thereof to the matrix. Additional examples of polymer matrices such as hydrogels are described in Section V and Section VII.

In some aspects, one or more of the primers disclosed herein comprise a 5' overhang upon hybridization to the antigen receptor transcript. In some embodiments, the 5' overhang is configured to be linked to one another, other molecules (e.g., one or more crosslinking reagents, such as PEG comprising functional groups), molecules in the sample, and/or a matrix in or embedding the sample (e.g., a cellular matrix or a hydrogel matrix). In some embodiments, the 5' overhangs of the primers comprise one or more functional groups, e.g., amine-modified nucleotides that can react with an acrylic acid N-hydroxysuccinimide moiety and/or one or more click functional groups. In some embodiments, after primer hybridization to an antigen receptor transcript, the 5' overhangs of the primers are crosslinked to one another and/or to other molecules, thereby immobilizing the primers in the sample. Extensions of the primers by a polymerase (e.g., a reverse transcriptase with strand displacement activity) can incorporate unmodified nucleotides into the extension product, thereby generating cDNA and prevent diffusion of the cDNA without the need of crosslinking the incorporated nucleotides. In some embodiments, crosslinking the 5' overhangs of the primers can generate a high molecular weight product of the cDNA molecules that are less likely to diffuse away from the antigen receptor transcript. In some embodiments, strand displacement of the cDNA molecules allows additional primer molecules to hybridize to the antigen receptor transcript, and the 5' overhangs of the additional primer molecules can be crosslinked to one another, to the already generated cDNA molecules, and/or to other molecules in the sample, before additional cDNA molecules are generated from the additional primer molecules.

Figure 4B:
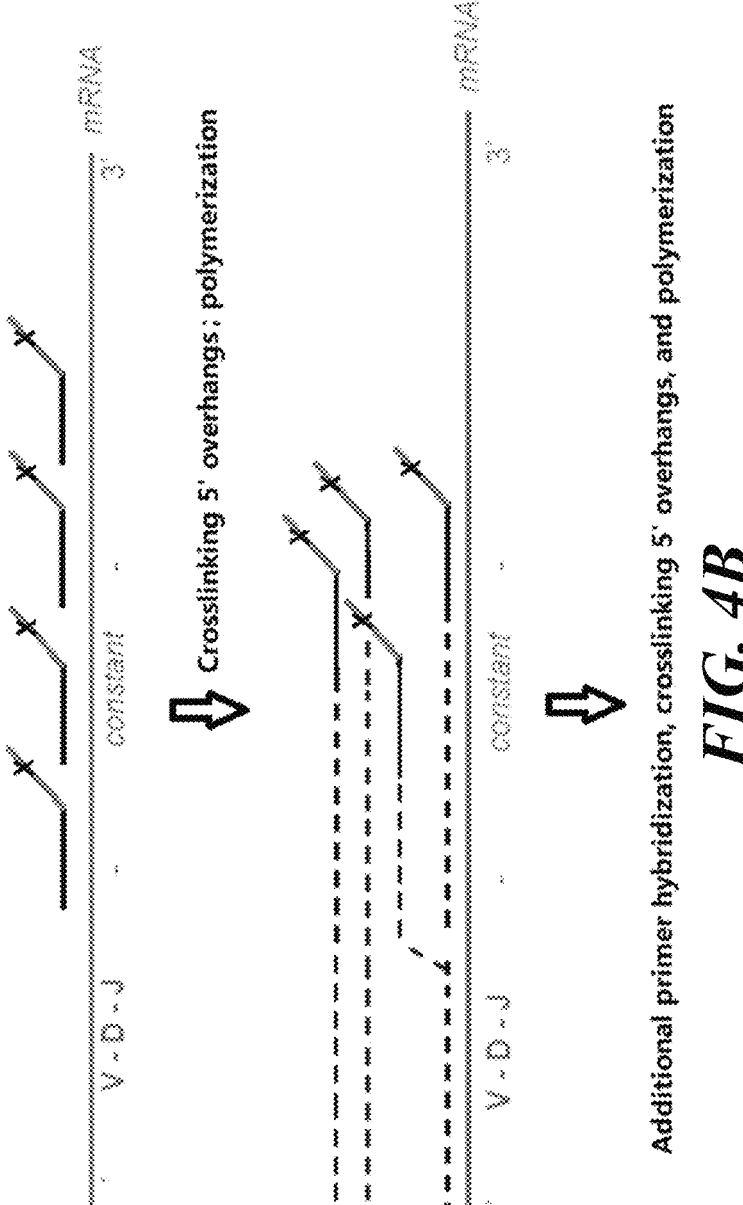
FIG. 4B shows that the plurality of primers can comprise 5' overhangs that can be crosslinked (indicated by "X") to one another, to other molecules in the sample, and/or to a matrix embedding the sample.

As shown in FIG. 4A, cDNAs comprising functionalized groups (e.g., functional groups in modified nucleotides) can be crosslinked (e.g., as illustrated by "X" in the figure), thereby immobilizing the cDNA molecules at the location of the antigen receptor transcript. FIG. 4B shows the 5' overhangs of primers can be crosslinked (e.g., as illustrated by "X" in the figure) before, during, and/or after the generation of cDNA molecules, thereby immobilizing the generated cDNA molecules at the location of the antigen receptor transcript. Generation and immobilization of multiple cDNA molecules can enrich detectable V(D)J sequences, preserve the spatial information of the cDNA relative to the antigen receptor transcript within the cell or sample, and allow in situ detection of a cellular and/or subcellular localization or distribution pattern of various antigen receptor transcripts. During or after cDNA immobilization, probes can be contacted with the sample to hybridize to the immobilized cDNA for in situ detection. For example, circularizable probes or probe sets can be hybridized to the immobilized cDNA for in situ RCA-based detection.

IV. Circularizing Probe or Nucleic Acid Molecules

In some embodiments, provide herein are molecules that can be circularized. In some embodiments, a nucleic acid molecule comprising a V(D)J sequence, e.g., a cDNA of an antigen receptor transcript, is circularizable to generate a circularized molecule. In some embodiments, a circularizable probe or probe set is hybridized to a nucleic acid molecule comprising a V(D)J sequence, and the circularizable probe or probe set is circularized to generate a circularized molecule. The circularized molecule comprising the V(D)J sequence or a complement thereof can be amplified (e.g., through RCA) and the amplification product can be detected in order to detect the V(D)J sequence.

Figure 5A:
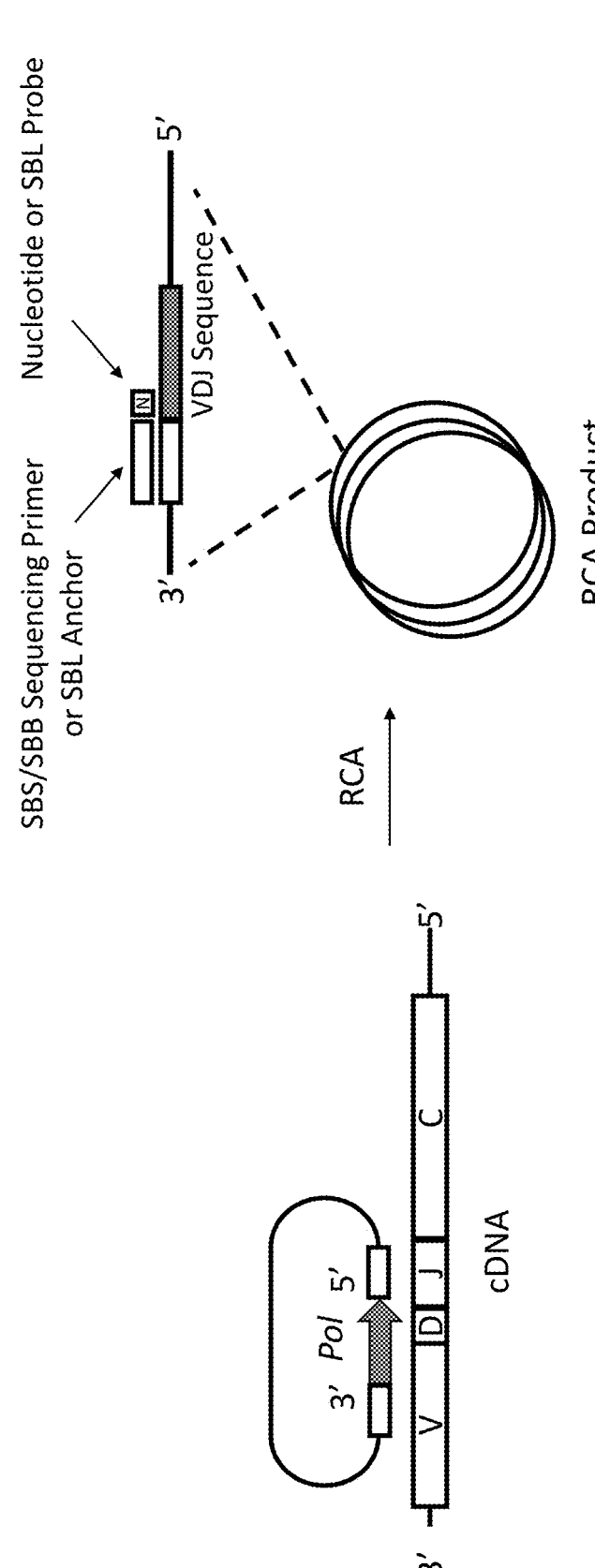
FIG. 5A shows an exemplary circularizable probe in which the gap is filled by a polymerase, thereby incorporating sequence information of the VDJ join into the circularized probe. The circularized probe can be amplified by RCA, and the VDJ sequence can be the RCA product is detected using sequencing by synthesis (SBS), sequencing by binding (SBB), or sequencing by ligation (SBL), etc.
Figure 5B:
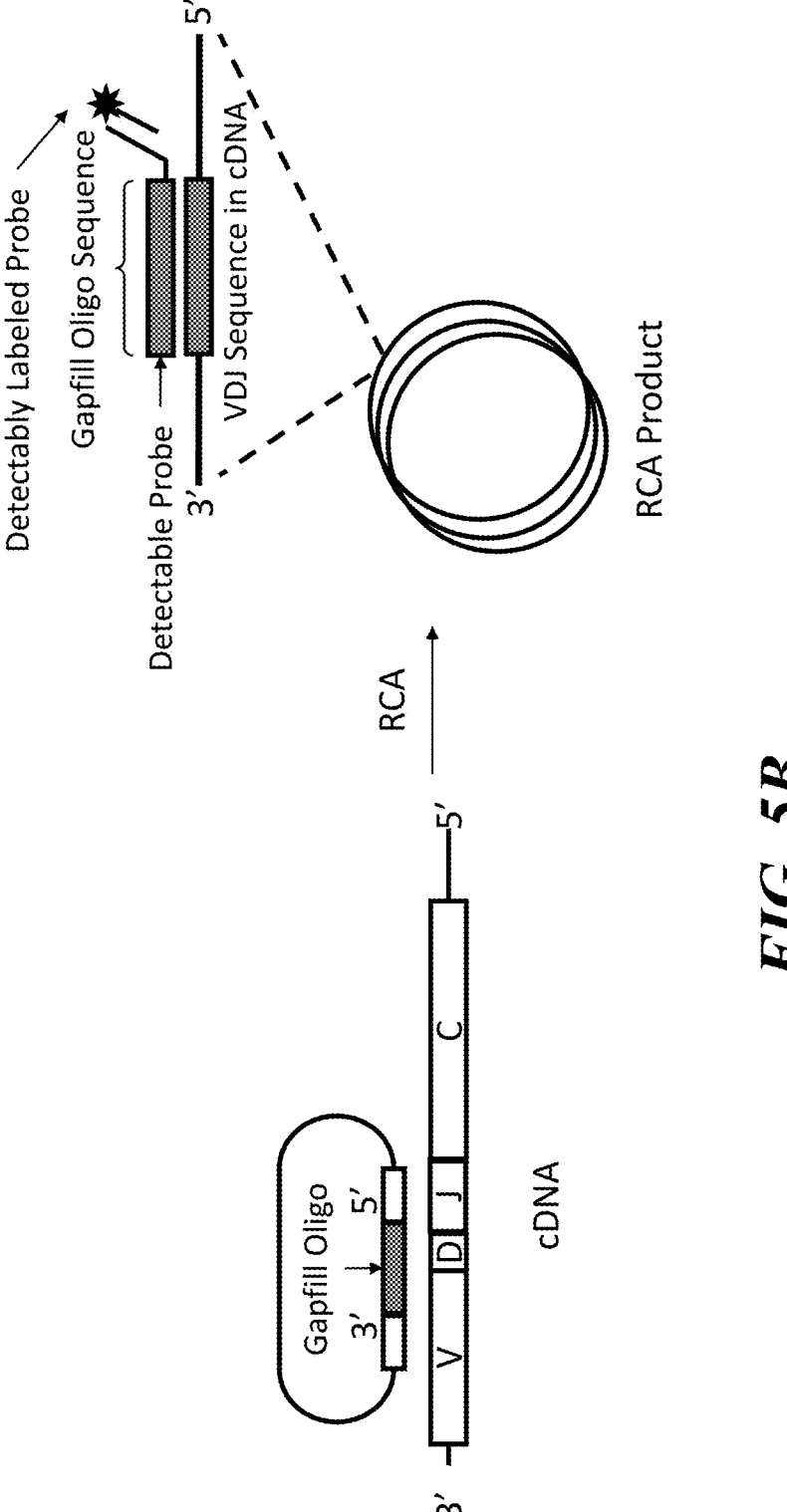
FIG. 5B shows an exemplary circularizable probe in which the gap is filled by a gapfill oligonucleotide complementary to the VDJ sequence in the cDNA. The circularized probe can be amplified by RCA, and the VDJ sequence in the RCA product can be detected using sequential hybridization of detectable probes having hybridization regions (e.g., recognition sequences) that share identical sequences with the gapfill oligonucleotides.

In some embodiments, the circularizable probe or probe set comprises a 3' region that hybridizes to a sequence in the V region (e.g., V segment) of the nucleic acid molecule (e.g., a cDNA), for instance, as shown in FIGS. 5A-5B. In some embodiments, the circularizable probe or probe set comprises a 3' region that hybridizes to a sequence 3' to the V segment of the nucleic acid molecule (e.g., a cDNA). In some embodiments, the circularizable probe or probe set comprises a 3' region that hybridizes to the V segment or a portion thereof, as well as to a sequence 3' to the V segment of the nucleic acid molecule (e.g., a cDNA).

In some embodiments, the circularizable probe or probe set comprises a 5' region that hybridizes to a sequence in the J region (e.g., J segment) of the nucleic acid molecule (e.g., a cDNA), for instance, as shown in FIGS. 5A-5B. In some embodiments, the circularizable probe or probe set comprises a 5' region that hybridizes to a sequence 5' to the J segment of the nucleic acid molecule (e.g., a cDNA). In some embodiments, the circularizable probe or probe set comprises a 5' region that hybridizes to the J segment or a portion thereof, as well as to a sequence 5' to the J segment of the nucleic acid molecule (e.g., a cDNA).

In some embodiments, the 3' region of the circularizable probe or probe set hybridizes to the V segment or a portion thereof in the cDNA and the 5' region of the circularizable probe or probe set hybridizes to the J segment or a portion thereof in the cDNA. In some embodiments, the 3' region of the circularizable probe or probe set hybridizes to a sequence 3' to the V segment in the cDNA and the 5' region of the circularizable probe or probe set hybridizes to a sequence 5' to the J segment in the cDNA.

In some embodiments, the sequence 3' to the V segment in the cDNA comprises an L (leader) sequence. In some embodiments, the sequence 3' to the V segment in the cDNA comprises an adaptor sequence. In some embodiments, the sequence 5' to the J segment in the cDNA comprises a C (constant) region sequence.

In some embodiments, the sequence 5' to the J segment in the cDNA comprises an IgH C region sequence or a portion thereof. In some embodiments, the sequence 5' to the J segment in the cDNA comprises an IgH Cμ region sequence or a portion thereof. In some embodiments, the sequence 5' to the J segment in the cDNA comprises an IgH Cδ region sequence or a portion thereof. In some embodiments, the sequence 5' to the J segment in the cDNA comprises an IgH Cγ region sequence or a portion thereof. In some embodiments, the sequence 5' to the J segment in the cDNA comprises an IgH Cα region sequence or a portion thereof. In some embodiments, the sequence 5' to the J segment in the cDNA comprises an IgH Cε region sequence or a portion thereof. In some embodiments, the sequence 5' to the J segment in the cDNA comprises an Igκ C region sequence or a portion thereof. In some embodiments, the sequence 5' to the J segment in the cDNA comprises an Igλ C region sequence or a portion thereof.

In some embodiments, the sequence 5' to the J segment in the cDNA comprises a TCR Cα region sequence or a portion thereof. In some embodiments, the sequence 5' to the J segment in the cDNA comprises a TCRβ C region sequence or a portion thereof. In some embodiments, the sequence 5' to the J segment in the cDNA comprises a TCR Cβ1 region sequence or a portion thereof. In some embodiments, the sequence 5' to the J segment in the cDNA comprises a TCR Cβ2 region sequence or a portion thereof. In some embodiments, the sequence 5' to the J segment in the cDNA comprises a TCRγ C region sequence or a portion thereof. In some embodiments, the sequence 5' to the J segment in the cDNA comprises a TCRδ C region sequence or a portion thereof.

In some embodiments, upon hybridization of a circularizable probe to the nucleic acid molecule (e.g., cDNA), the 3' terminal nucleotide and the 5' terminal nucleotide of the circularizable probe are not juxtaposed directly next to each other; as such, a ligase alone cannot catalyze the formation of a phosphodiester bond directly between the 5' phosphate of the 5' terminal nucleotide and the 3' hydroxyl of the 3' terminal nucleotide. In some embodiments, upon hybridization of a circularizable probe to the nucleic acid molecule (e.g., cDNA), the 3' terminal nucleotide and the 5' terminal nucleotide of the circularizable probe are separated from each other by a gap of between about 1 and about 500 nucleotides in length. In some embodiments, the gap is about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, or about 200 nucleotides in length, or of any integer (or range of integers) of nucleotides in between the indicated values. In some embodiments, the gap is between about 200 and about 300, between about 300 and about 400, or between about 400 and about 500 nucleotides in length. In some embodiments, one or more gaps between 3' and 5' ends of the circularizable probe or probe set are formed upon hybridization to the nucleic acid molecule (e.g., cDNA).

In some embodiments, a circularized nucleic acid disclosed herein comprises one or more barcode sequences. In some embodiments, a circularizable probe or probe set comprises one or more barcode sequences. In some embodiments, a splint used to circularize a cDNA comprises one or more barcode sequences. The barcode sequences, if present, may be of any length. If more than one barcode sequence is used, the barcode sequences may independently have the same or different lengths, such as at least 5, at least 10, at least 15, at least 20, at least 25, at least 30, at least 35, at least 40, at least 50 nucleotides in length. In some embodiments, the barcode sequence may be no more than 120, no more than 112, no more than 104, no more than 96, no more than 88, no more than 80, no more than 72, no more than 64, no more than 56, no more than 48, no more than 40, no more than 32, no more than 24, no more than 16, or no more than 8 nucleotides in length. Combinations of any of these are also possible, e.g., the barcode sequence may be between 5 and 10 nucleotides, between 8 and 15 nucleotides, etc.

The barcode sequence may be arbitrary or random. In certain cases, the barcode sequences are chosen so as to reduce or minimize homology with other components in a sample, e.g., such that the barcode sequences do not themselves bind to or hybridize with other nucleic acids suspected of being within the cell or other sample. In some embodiments, between a particular barcode sequence and another sequence (e.g., a cellular nucleic acid sequence in a sample or other barcode sequences in probes added to the sample), the homology may be less than 10%, less than 8%, less than 7%, less than 6%, less than 5%, less than 4%, less than 3%, less than 2%, or less than 1%. In some embodiments, the homology may be less than 20, 19, 18, 17, 16, 15, 14, 13, 12, 11, 10, 9, 8, 7, 6, 5, 4, 3, or 2 bases, and in some embodiments, the bases are consecutive bases.

In some embodiments, the number of distinct barcode sequences in a population of nucleic acid probes is less than the number of distinct targets of the nucleic acid probes, and yet the distinct targets may still be uniquely identified from one another, e.g., by encoding a probe with a different combination of barcode sequences. However, not all possible combinations of a given set of barcode sequences need be used. For instance, each probe may contain 1, 2, 3, 4, 5, 6, 7, 8, 9, 10, 11, 12, 13, 14, 15, etc. or more barcode sequences. In some embodiments, a population of nucleic acid probes may each contain the same number of barcode sequences, although in other cases, there may be different numbers of barcode sequences present on the various probes. In some embodiments, the barcode sequences or any subset thereof in the population of nucleic acid probes can be independently and/or combinatorially detected and/or decoded.

A. Gapfill Polymerization

In some embodiments, a gap in a circularizable probe hybridized to the nucleic acid molecule (e.g., cDNA comprising a V(D)J sequence) may be filled by extending a 3' end of the circularizable probe or probe set. In some embodiments, a polymerase is used to extend the 3' end using the nucleic acid molecule (e.g., cDNA) as a template, thereby filling the gap using nucleotide sequence in the nucleic acid molecule (e.g., cDNA). In some embodiments, gap filling by the polymerase incorporates nucleotides residues into the circularizable probe or probe set, and the incorporated nucleotide sequence is complementary to the V(D)J sequence or a portion thereof in the nucleic acid molecule (e.g., cDNA). In some embodiments, the incorporated nucleotide sequence is complementary to the V segment or a portion thereof in the cDNA. In some embodiments, the incorporated nucleotide sequence is complementary to the D region or a portion thereof in the cDNA. In some embodiments, the incorporated nucleotide sequence is complementary to the J segment or a portion thereof in the cDNA. In some embodiments, the incorporated nucleotide sequence is complementary to the D region or a portion thereof but not complementary to the V or J segment in the cDNA. In some embodiments, the incorporated nucleotide sequence is complementary to the V segment or a portion thereof, the D region, and the J segment or a portion thereof in the cDNA.

In some instances, the gap filling is performing using a polymerase (e.g., DNA polymerase) in the presence of appropriate dNTPs and other cofactors, under isothermal conditions or non-isothermal conditions. Exemplary DNA polymerases include but are not limited to: *E. coli* DNA polymerase I, Bsu DNA polymerase, Bst DNA polymerase, Taq DNA polymerase, VENT™ DNA polymerase, DEEP-VENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® Quick-Load® DNA polymerase, Hemo KlenTaq® DNA poly-merase, REDTaq® DNA polymerase, Phusion® DNA poly-merase, Phusion® High-Fidelity DNA polymerase, Platinum Pfx DNA polymerase, AccuPrime Pfx DNA poly-merase, Phi29 DNA polymerase, Klenow fragment, Pwo DNA polymerase, Pfu DNA polymerase, T4 DNA poly-merase and T7 DNA polymerase enzymes.

In some instances, the gap filling is performing using a DNA polymerase capable of incorporating at least about 25, at least about 50, at least about 100, at least about 125, at least about 150, at least about 175, at least about 200, at least about 225, at least about 250, at least about 300, at least about 400, at least about 500, at least about 600, or at least about 1,000 nucleotides in a single binding event before dissociating from the nucleic acid molecule (e.g., cDNA).

Incorporation of the correct nucleotides to a growing strand of DNA, as determined by the template, is known as sequence fidelity. Interestingly, there is wide variation in sequence fidelity among DNA polymerases. In some embodiments, a high fidelity DNA polymerase is used for gap filling and examples include but are not limited to: Taq DNA polymerase, Phusion® High-Fidelity DNA Poly-merase, KAPA Taq, KAPA Taq HotStart DNA Polymerase, KAPA HiFi, and/or Q5® High-Fidelity DNA Polymerase.

In some instances, the gap filling is performing using a polymerase having no or limited strand displacement activ-ity, such that an extended 3' region of the circularizable probe or probe set does not displace the 5' region hybridized to the nucleic acid molecule (e.g., cDNA). For example, T4 and T7 DNA Polymerases lack strand displacement activity and can be used for this purpose. In some embodiments, especially where the target nucleic acid is RNA, the poly-merase can be a reverse transcriptase. Reverse transcriptases having reduced strand displacement activity can be used, see, e.g., Martin-Alonso et al., *ACS Infect. Dis.* 2020, 6, 5, 1140-1153, which is incorporated herein by reference in its entirety.

In some embodiments, the 3' region of the circularizable probe extended by the polymerase can be juxtaposed to the 5' region of the circularizable probe, forming a nick. In some embodiments, the ligation involves template dependent liga-tion, e.g., using the V(D)J sequence in the cDNA as tem-plate. In some embodiments, the ligation involves template independent ligation.

The nick can be ligated using chemical ligation. In some embodiments, the chemical ligation involves click chemis-try.

In some embodiments, the ligation involves enzymatic ligation. In some embodiments, the enzymatic ligation involves use of a ligase. In some aspects, the ligase used herein comprises an enzyme that is commonly used to join polynucleotides together or to join the ends of a single polynucleotide. In some aspects, the ligase used herein is a DNA ligase. In some aspects, the ligase used herein is an ATP-dependent double-strand polynucleotide ligases, NAD-i-dependent double-strand DNA or RNA ligases and single-strand polynucleotide ligases, for example any of the ligases described in EC 6.5.1.1 (ATP-dependent ligases), EC 6.5.1.2 (NAD+-dependent ligases), EC 6.5.1.3 (RNA ligases). Spe-cific examples of ligases comprise bacterial ligases such as *E. coli* DNA ligase, Tth DNA ligase, *Thermococcus* sp. (strain 9° N) DNA ligase (9°N™ DNA ligase, New England Biolabs), Taq DNA ligase, Ampligase™ (Epicentre Biotech-nologies) and phage ligases such as T3 DNA ligase, T4 DNA ligase and T7 DNA ligase and mutants thereof. In some embodiments, the ligase is a T4 RNA ligase. In some embodiments, the ligase is a splintR ligase. In some embodi-ments, the ligase is a single stranded DNA ligase. In some embodiments, the ligase is a T4 DNA ligase. In some embodiments, the ligase is a ligase that has an DNA-splinted DNA ligase activity. In some embodiments, the ligase is a ligase that has an RNA-splinted DNA ligase activity. In some embodiments, the ligase is a ssDNA ligase. In some embodiments, the ssDNA ligase is a bacteriophage TS2126 RNA ligase or an archaebacterium RNA ligase or a variant or derivative thereof. In some embodiments, the ligase is *Methanobacterium thermoautotrophicum* RNA ligase 1, CircLigase™ I, CircLigase™ II, T4 RNA ligase 1, or T4 RNA ligase 2, or a variant or derivative thereof.

FIG. 5A shows an example of using a polymerase (Pol) to extend a 3' region of a circularizable probe using a V(D)J sequence in the cDNA as a template, followed by using a ligase to ligate the extended 3' region to the 5' region of the circularizable probe, thereby filling the gap, circularizing the circularizable probe, and incorporating sequence informa-tion of the V(D)J sequence into the circularized probe. In some embodiments, the circularized probe comprises a sequence complementary to the D segment of the V(D)J sequence in the cDNA. In some embodiments, the circular-ized probe comprises a VDJ sequence which comprises the D segment, a portion of the V segment, and a portion of the J segment, for instance, as shown in FIG. 5A.

In some embodiments, the circularized probe is amplified by RCA (e.g., as described in Section V), and the RCA product comprises multiple copies of the V(D)J sequence in the cDNA. In some embodiments, the V(D)J sequence or a portion thereof (e.g., a portion comprising the D segment) in the RCA product is determined in situ, e.g., by sequencing the V(D)J sequence using sequencing by synthesis (SBS), sequencing by ligation (SBL), sequencing by binding (SBB), sequential hybridization of detectable probes, etc., as described in Section VI.

B. Gapfill Oligonucleotide Ligation

In some embodiments, a gap in a circularizable probe hybridized to the nucleic acid molecule (e.g., cDNA com-prising a V(D)J sequence) may be filled by a gapfill oligo-nucleotide. The gapfill oligonucleotide can be provided in one part or two or more parts. In some embodiments, the gapfill oligonucleotide is ligated to the circularizable probe, and when the gapfill oligonucleotide comprises two or more parts, the parts can be ligated to one another, thereby circularizing the circularizable probe.

In some embodiments, upon hybridization to the nucleic acid molecule (e.g., cDNA), the 5' terminal nucleotide of the gapfill oligonucleotide is adjacent to the 3' terminal nucleo-tide of the circularizable probe, and the 3' terminal nucleo-tide of the gapfill oligonucleotide is adjacent to the 5' terminal nucleotide of the circularizable probe. In some embodiments, the 5' terminal nucleotide of the gapfill oli-gonucleotide and the 3' terminal nucleotide of the circular-izable probe are separated by a nick or a gap of one or more nucleotides, e.g., 1, 2, 3, 4, 5, 6, 7, 8, 9, 10, or more nucleotides. In some embodiments, the 3' terminal nucleo-tide of the gapfill oligonucleotide and the 5' terminal nucleo-tide of the circularizable probe are separated by a nick or a gap of one or more nucleotides, e.g., 1, 2, 3, 4, 5, 6, 7, 8, 9, 10, or more nucleotides. The nick can be ligated using any suitable ligase disclosed herein, and the gap can be filled using any suitable ligase polymerase followed by ligation, for example, as described in Section IV-A.

In some aspects, a high fidelity ligase, such as a thermo-stable DNA ligase (e.g., a Taq DNA ligase), is used. Ther-mostable DNA ligases are active at elevated temperatures, allowing further discrimination by incubating the ligation at a temperature near the melting temperature ($T_m$) of the DNA strands. This selectively reduces the concentration of annealed mismatched substrates (expected to have a slightly lower $T_m$ around the mismatch) over annealed fully base-paired substrates. Thus, high-fidelity ligation can be achieved through a combination of the intrinsic selectivity of the ligase active site and balanced conditions to reduce the incidence of annealed mismatched dsDNA.

In some embodiments, the gapfill oligonucleotide comprises a sequence complementary to the V(D)J sequence or a portion thereof in the nucleic acid molecule (e.g., cDNA). In some embodiments, the incorporated nucleotide sequence is complementary to the V segment or a portion thereof in the cDNA. In some embodiments, the gapfill oligonucleotide comprises a sequence complementary to the D region or a portion thereof in the cDNA. In some embodiments, the gapfill oligonucleotide comprises a sequence complementary to the J segment or a portion thereof in the cDNA. In some embodiments, the gapfill oligonucleotide comprises a sequence complementary to the D region or a portion thereof but no sequence complementary to the V or J segment in the cDNA. In some embodiments, the gapfill oligonucleotide comprises a sequence complementary to the V segment or a portion thereof, the D region, and the J segment or a portion thereof in the cDNA.

FIG. 5B shows an example of hybridizing a gapfill oligonucleotide (Gapfill Oligo) to the nucleic acid molecule (e.g., cDNA) between the 3' region and the 5' region of the circularizable probe, and using one or more ligases to ligate the gapfill oligonucleotide to the circularizable probe (with or without gapfilling prior to ligation at either or both ligation sites), thereby filling the gap, circularizing the circularizable probe, and incorporating sequence information of the V(D)J sequence in the cDNA into the circularized probe. In some embodiments, the gapfill oligonucleotide comprises a VDJ sequence which comprises the D segment, a portion of the V segment, and a portion of the J segment, for instance, as shown in FIG. 5B.

In some embodiments, the biological sample is contacted with a library of gapfill oligonucleotides. In some embodiments, the library comprises at least about 100, at least about 250, at least about 500, at least about 1,000, at least about 2,500, at least about 5,000, at least about 10,000, at least about 25,000, at least about 50,000, or more oligonucleotides of different sequences. In some embodiments, the sequence diversity of the gapfill oligonucleotides in the library is such that at least or about 5%, at least or about 10%, at least or about 15%, at least or about 20%, at least or about 25%, at least or about 30%, at least or about 35%, at least or about 40%, at least or about 45%, at least or about 50%, at least or about 55%, at least or about 60%, at least or about 65%, at least or about 70%, at least or about 75%, at least or about 80%, at least or about 85%, at least or about 90%, at least or about 95%, or about 100% of the V(D)J sequences in the antigen receptor transcripts in a sample have corresponding gapfill oligonucleotides in the library, e.g., the gapfill oligonucleotides comprise sequences that are identical to the V(D)J sequences in the antigen receptor transcripts.

The library of gapfill oligonucleotides may be randomly or partially randomly generated. In some embodiments, the library comprises oligonucleotides comprising one or more degenerate sequences. In some embodiments, the library is randomly generated. For instance, a degenerate collection of sequences can be randomly generated by synthesizing with a mixture of all four bases at each position. For example, if the gapfill oligonucleotides are 10-mers synthesized with a mixture of A, C, G, and T at each position, there are 410 possible sequences. In some embodiments, the library is partially randomly generated. In some embodiments, oligonucleotides with a diverse but pre-defined set of sequences can be synthesized and used as gapfill oligonucleotides. For example, one or more positions in the oligonucleotides can be fixed (e.g., containing only possible nucleotide) or less diverse (e.g., containing only two possible nucleotides) than one or more other positions (e.g., containing three or four possible nucleotides) in the oligonucleotides.

In some embodiments, the gap filling is performed under conditions permissive for specific hybridization of a gapfill oligonucleotide to its complementary sequence in the V(D)J sequence in the nucleic acid molecule (e.g., cDNA), and/or specific hybridization of a circularizable probe or probe set to the nucleic acid molecule. In some embodiments, the circularizable probe or probe set comprises hybridization regions that hybridize to the nucleic acid molecule at sequences outside the V(D)J sequence (e.g., at constant region sequences on the 5' of the J segment in cDNA and/or at adaptor sequences on the 3' of V segment), which are less diverse than the V(D)J sequence. In some embodiments, the circularizable probe or probe set comprises hybridization regions that hybridize to the nucleic acid molecule at the V segment and the J segment, which are less diverse in sequence than the D segment.

In some embodiments, the circularized probe is amplified by RCA (e.g., as described in Section V), and the RCA product comprises multiple copies of the V(D)J sequence in the cDNA. In some embodiments, a sequence in the V(D)J sequence in the RCA product is determined in situ, e.g., by sequencing the V(D)J sequence using SBS, SBB, SBL, or sequential hybridization of detectable probes, etc., as described in Section VI.

C. Circularization of cDNA

In some embodiments, the methods provided herein further comprises ligating the nucleic acid molecule (e.g., the cDNA generated by reverse transcription of the VDJ transcript) to generate a circularized molecule.

In some embodiments, the nucleic acid molecule is circularized using template-independent ligation. In some embodiments, the template-independent ligation is click chemistry ligation or enzymatic ligation. In some embodiments, the nucleic acid molecule (e.g. the cDNA) is circularized using a single-stranded DNA (ssDNA) ligase, such as a bacteriophage TS2126 RNA ligase or an archaebacterium RNA ligase or a variant or derivative thereof. Exemplary ligases include but are not limited to *Methanobacterium thermoautotrophicum* RNA ligase 1, CircLigase™ I, CircLigase™ II, T4 RNA ligase 1, and T4 RNA ligase 2.

In some embodiments, the nucleic acid molecule (e.g., the cDNA) is circularized using template-dependent ligation. In some embodiments, the template-dependent ligation is click chemistry ligation or enzymatic ligation. In some embodiments, the nucleic acid molecule is circularized using a splint that hybridizes to both ends of the nucleic acid molecule.

Figure 6:
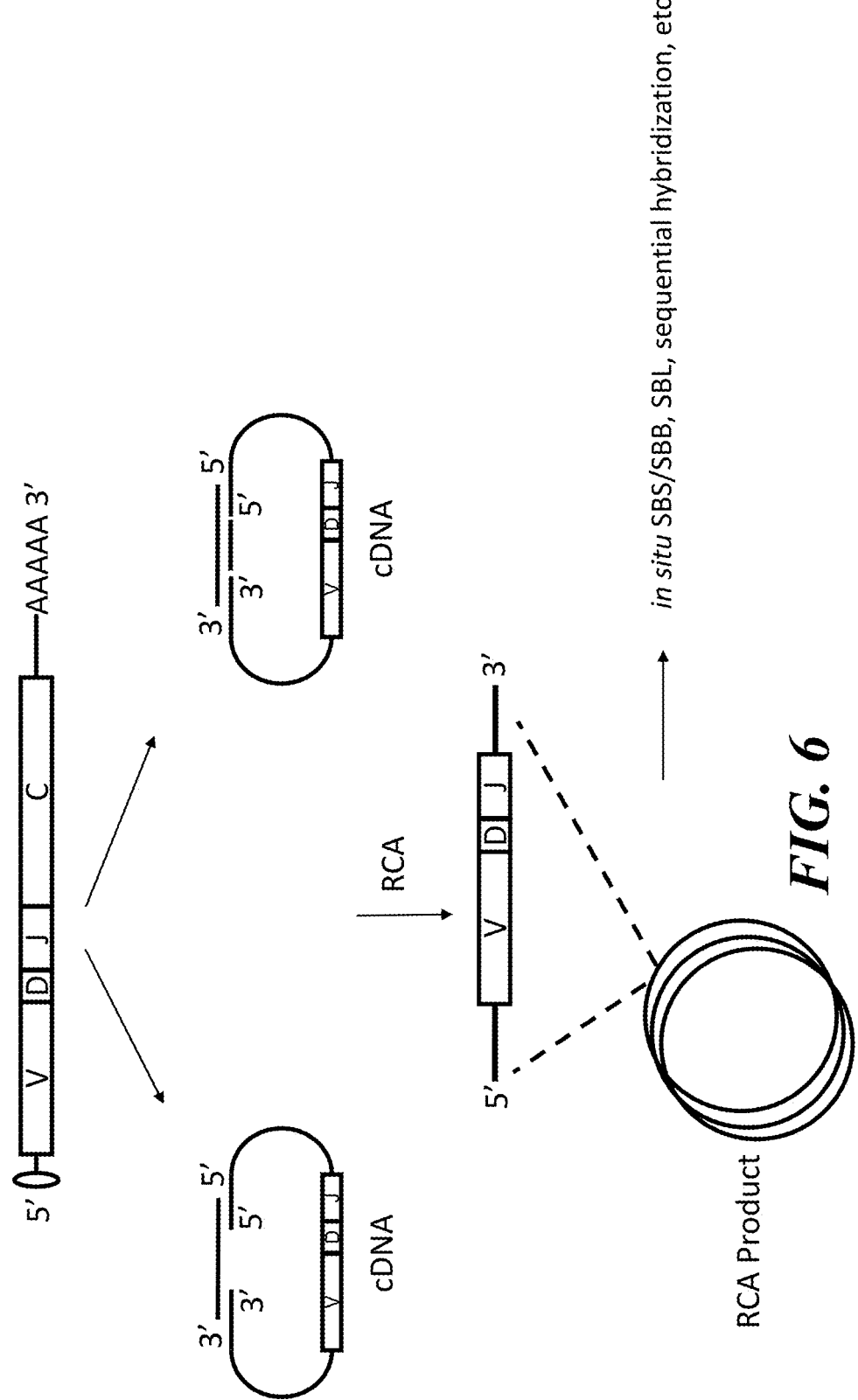
FIG. 6 shows examples of splinted ligation of the cDNA molecule to generate circularized cDNA for RCA-based in situ detection of VDJ sequences.

FIG. 6 shows non-limiting examples of template-dependent ligation of the cDNA molecule. In some aspects, a circularizable cDNA hybridized to a splint, wherein the splint comprises: a 3' region that hybridizes to a sequence in and/or 3' to the V segment of the cDNA molecule; and a 5' region that hybridizes to a sequence in and/or 5' to the J segment of the cDNA molecule. In some embodiments, the 3' region of the splint hybridizes to a sequence in the V segment and the 5' region of the splint hybridizes to a sequence in the J segment. In some embodiments, the 3' region of the splint hybridizes to a sequence 3' to the V segment and the 5' region of the splint hybridizes to a sequence 5' to the J segment in the cDNA. In some embodiments, the sequence 3' to the V segment is an adaptor sequence and the sequence 5' to the J segment is a C (constant) region sequence. The splint may be a single-stranded splint, or comprises single-stranded 3' and 5' regions flanking a double-stranded region. In some embodiments, the splint comprises a barcode region comprising one or more barcode sequences. The nucleic acid molecule may be circularized with or without gap filling prior to ligation using the splint as a template.

In some embodiments, the same splint can be used to circularize cDNA comprising different V(D)J sequences. For example, the splint can comprise a 3' end sequence that hybridizes to a common or universal adaptor sequence that is 3' to the V segment in a plurality of different cDNA molecules, and the splint can further comprise a 5' end sequence that hybridizes to a constant region sequence that is 5' to the J segment in the plurality of different cDNA molecules. The circularized cDNA molecules In some embodiments, the circularized cDNA is amplified by RCA (e.g., as described in Section V), and the RCA product comprises multiple copies of a sequence that is complementary to the V(D)J sequence in the cDNA. In some embodiments, a sequence in the RCA product is determined in situ, e.g., by sequencing the V(D)J sequence in the RCA product using SBS, SBB, or SBL, or sequential hybridization of detectable probes, etc., as described in Section VI.

V. Rolling Circle Amplification (RCA)

Following formation of the circularized nucleic acid molecule (e.g., generated from a cDNA or a circularizable probe hybridized to a cDNA), in some instances, a primer oligonucleotide is added for amplification. In some instances, the primer oligonucleotide is added with the circularizable probe or probe set. In some instances, the primer oligonucleotide is added before or after the circularizable probe or probe set is contacted with the sample. In some instances, the primer oligonucleotide for amplification of the circularized nucleic acid molecule may comprise a sequence complementary to a cDNA, as well as a sequence complementary to the circularizable probe that hybridizes to the cDNA. In some embodiments, a washing step is performed to remove any unbound probes, primers, etc. In some embodiments, the wash is a stringency wash. Washing steps can be performed at any point during the process to remove non-specifically bound probes, probes that have ligated, etc.

A primer oligonucleotide for amplification of the circularized nucleic acid molecule can comprise a single-stranded nucleic acid sequence having a 3' end that can be used as a substrate for a nucleic acid polymerase in a nucleic acid extension reaction. The primer oligonucleotide can comprise both RNA nucleotides and DNA nucleotides (e.g., in a random or designed pattern). The primer oligonucleotide can also comprise other natural or synthetic nucleotides described herein that can have additional functionality. The primer oligonucleotide can be about 6 bases to about 100 bases, such as about 25 bases.

In some instances, upon addition of a DNA polymerase in the presence of appropriate dNTP precursors and other cofactors, the amplification primer is elongated by replication of multiple copies of the template. The amplification step can utilize isothermal amplification or non-isothermal amplification. In some embodiments, after the formation of the hybridization complex and any subsequent circularization (such as ligation of, e.g., a padlock probe) the circularized nucleic acid molecule is rolling-circle amplified to generate a RCA product (e.g., amplicon) containing multiple copies of the sequence of the circularized nucleic acid molecule.

In some embodiments, rolling circle amplification products are generated using a polymerase selected from the group consisting of Phi29 DNA polymerase, Phi29-like DNA polymerase, M2 DNA polymerase, B103 DNA polymerase, GA-1 DNA polymerase, phi-PRD1 polymerase, Vent DNA polymerase, Deep Vent DNA polymerase, Vent (exo-) DNA polymerase, KlenTaq DNA polymerase, DNA polymerase I, Klenow fragment of DNA polymerase I, DNA polymerase III, T3 DNA polymerase, T4 DNA polymerase, T5 DNA polymerase, T7 DNA polymerase, Bst polymerase, rBST DNA polymerase, N29 DNA polymerase, TopoTaq DNA polymerase, T7 RNA polymerase, SP6 RNA polymerase, T3 RNA polymerase, and a variant or derivative thereof. In some embodiments, the polymerase is Phi29 DNA polymerase.

In some embodiments, the polymerase comprises a modified recombinant Phi29-type polymerase. In some embodiments, the polymerase comprises a modified recombinant Phi29, B103, GA-1, PZA, Phi15, BS32, M2Y, Nf, G1, Cp-1, PRD1, PZE, SF5, Cp-5, Cp-7, PR4, PRS, PR722, or L17 polymerase. In some embodiments, the polymerase comprises a modified recombinant DNA polymerase having at least one amino acid substitution or combination of substitutions as compared to a wildtype Phi29 polymerase. Exemplary polymerases are described in U.S. Pat. Nos. 8,257,954; 8,133,672; 8,343,746; 8,658,365; 8,921,086; and 9,279,155, all of which are herein incorporated by reference. In some embodiments, the polymerase is not directly or indirectly immobilized to a substrate, such as a bead or planar substrate (e.g., glass slide), prior to contacting a sample, although the sample may be immobilized on a substrate.

In some embodiments, the amplification is performed at a temperature between or between about 20° C. and about 60° C. In some embodiments, the amplification is performed at a temperature between or between about 30° C. and about 40° C. In some aspects, the amplification step, such as the rolling circle amplification (RCA) is performed at a temperature between at or about 25° C. and at or about 50° C., such as at or about 25° C., 27° C., 29° C., 31° C., 33° C., 35° C., 37° C., 39° C., 41° C., 43° C., 45° C., 47° C., or 49° C.

In some aspects, during the amplification step, modified nucleotides can be added to the reaction to incorporate the modified nucleotides in the amplification product (e.g., nanoball). Exemplary of the modified nucleotides comprise amine-modified nucleotides. In some aspects of the methods, for example, for anchoring or cross-linking of the generated amplification product (e.g., nanoball) to a scaffold, to cellular structures and/or to other amplification products (e.g., other nanoballs). In some aspects, the amplification products comprises a modified nucleotide, such as an amine-modified nucleotide. In some embodiments, the amine-modified nucleotide reacts with an acrylic acid N-hydroxysuccinimide moiety. Examples of other amine-modified nucleotides comprise, but are not limited to, a 5-Aminoallyl-dUTP moiety modification, a 5-Propargylamino-dCTP moiety modification, a $N^6$-6-Aminohexyl-dATP moiety modification, or a 7-Deaza-7-Propargylamino-dATP moiety modification. In some embodiments, the modified nucleotides comprises base modifications, such as azide and/or alkyne base modifications, dibenzylcyclooctyl (DBCO) modifications, vinyl modifications, trans-Cyclooctene (TCO), and so on.

In some embodiments, the primer extension reaction mixture can comprise a deoxynucleoside triphosphate (dNTP) or derivative, variant, or analogue thereof. In some embodiments, the primer extension reaction mixture can comprise a catalytic cofactor of the polymerase. In any of the preceding embodiments, the primer extension reaction mixture can comprise a catalytic di-cation, such as $Mg^{2+}$ and/or $Mn^{2+}$.

In some aspects, the amplification product (e.g., RCA product) can be anchored to a polymer matrix. The amplification products may be immobilized within the matrix generally at the location of the nucleic acid being amplified, thereby creating a localized colony of amplicons. The amplification products may be immobilized within the matrix by steric factors. The amplification products may also be immobilized within the matrix by covalent or noncovalent bonding. In this manner, the amplification products may be considered to be attached to the matrix. By being immobilized to the matrix, such as by covalent bonding or cross-linking, the size and spatial relationship of the original amplicons is maintained. By being immobilized to the matrix, such as by covalent bonding or cross-linking, the amplification products are resistant to movement or unraveling under mechanical stress.

In some aspects, the amplification products (e.g., RCA products) are copolymerized and/or covalently attached to the surrounding matrix thereby preserving their spatial relationship and any information inherent thereto. In some embodiments, the RCA products are generated from DNA or RNA within a cell embedded in the matrix. In some embodiments, the RCA products can also be functionalized to form covalent attachment to the matrix preserving their spatial information within the cell thereby providing a subcellular localization distribution pattern. In some embodiments, the provided methods involve embedding RCA products in the presence of hydrogel subunits to form one or more hydrogel-embedded amplification products. In some embodiments, the hydrogel-tissue chemistry described comprises covalently attaching nucleic acids to in situ synthesized hydrogel for tissue clearing, enzyme diffusion, and multiple-cycle sequencing or probe hybridization while an existing hydrogel-tissue chemistry method cannot. In some embodiments, to enable amplification product embedding in the tissue-hydrogel setting, amine-modified nucleotides are comprised in the amplification step (e.g., RCA), functionalized with an acrylamide moiety using acrylic acid N-hydroxysuccinimide esters, and copolymerized with acrylamide monomers to form a hydrogel.

VI. Detection and Analysis

In some aspects, the provided methods involve analyzing, e.g., detecting or determining, one or more nucleic acid sequences such as V(D)J sequences in antigen receptor transcripts. In some cases, the analysis is performed on one or more images captured, and may comprise processing the image(s) and/or quantifying signals observed. In some embodiments, the analysis comprises detecting a sequence (e.g., a V(D)J sequence) present in the sample. In some embodiments, the analysis comprises quantification of puncta (e.g., if amplification products are detected). In some embodiments, the obtained information may be compared to a positive and negative control, or to a threshold of a feature to determine if the sample exhibits a certain feature or phenotype. In some cases, the information may comprise signals from a cell, a region, and/or comprise readouts from multiple detectable labels. In some case, the analysis further comprises displaying the information from the analysis or detection step. In some embodiments, software may be used to automate the processing, analysis, and/or display of data.

In some embodiments, following amplification, the sequence of the amplicon (e.g., RCA product) or a portion thereof, is determined or otherwise analyzed, for example by using detectably labeled probes and imaging. The analysis of the amplification products can comprise sequencing by synthesis (SBS), sequencing by binding (SBB), sequencing by ligation (SBL), sequencing by hybridization, and/or fluorescent in situ hybridization, and/or wherein the in situ hybridization comprises sequential fluorescent in situ hybridization.

In some embodiments, the RCA product comprises a sequencing primer binding site 3' to the V(D)J sequence, and a sequencing primer can be hybridized to the sequencing primer binding site, for instance, as shown in FIG. 5A.

In examples where SBS or SBB is used to sequence the V(D)J sequence in the RCA product, the biological sample can be contacted with nucleotides in sequential cycles, where in each cycle a complex is formed, the complex comprising i) the sequencing primer or an extension product thereof hybridized to the sequencing primer binding site 3' to the V(D)J sequence, ii) a polymerase, and iii) a cognate nucleotide that base pairs with a nucleotide in the V(D)J sequence, and a signal (ON) and/or an absence of signal (OFF) associated with the cognate nucleotide and/or the polymerase in the complex is detected at a particular location in the biological sample, wherein the ON signal, the OFF signal, or a combination thereof corresponds to the base in the cognate nucleotide and the corresponding nucleotide in the V(D)J sequence. In some embodiments, a signal code corresponding to the ON signal, the OFF signal, or a combination thereof is detected at the particular location. In some embodiments, the signal code corresponds to a signal of a first color, a signal of a second color, a signal of a third color, or absence of signal, wherein the first, second, and third colors are different. In some embodiments, the signal code corresponds a combination of signals of a first or second color, or absence of signal, wherein the first and second colors are different. In some embodiments, the signal code corresponds to a combination of ON and/or OFF signals, wherein the combination of ON and/or OFF signals is detected in two or more imaging steps.

In some embodiments, the V(D)J sequence is sequenced by SBB using a polymerase that is fluorescently labeled and one or more nucleotides that are not fluorescently labeled. In some embodiments, during SBB, a cognate nucleotide is not incorporated by the polymerase into the sequencing primer or an extension product thereof. In some embodiments, incorporation of a cognate nucleotide by the polymerase into the sequencing primer or an extension product thereof is attenuated or inhibited.

In some embodiments, the V(D)J sequence is sequenced by SBS, comprising contacting the biological sample with a nucleotide mix comprising a fluorescently labeled nucleotide and a nucleotide that is not fluorescently labeled. In some embodiments, during SBS, a cognate nucleotide is incorporated by the polymerase into the sequencing primer or an extension product thereof, and the cognate nucleotide may or may not be fluorescently labeled.

Any of the RCA products disclosed herein, including those shown in FIG. 5A, FIG. 5B, and FIG. 6, can be analyzed in situ using SBS or SBB in order to detect the V(D)J join or a sequence thereof in the RCA product.

In examples where SBL is used to sequence the V(D)J sequence in the RCA product, the biological sample can be contacted with an anchor of known sequence and detectably labeled probes, one of which are complementary to a sequence in the V(D)J sequence in the RCA product, for instance, as shown in FIG. 5A. The anchor can be 3' or 5' to the V(D)J sequence to be sequence. After hybridization of the complementary detectably labeled probe to the V(D)J sequence, it can be ligated to the anchor or an extended product thereof, whereas detectably labeled probes that are not complementary to the V(D)J sequence are not ligated and can be removed, e.g., by washing the sample. Signals associated with the complementary detectably labeled probe ligated to the anchor or extension product thereof can be detected, thereby detecting the corresponding sequence in the V(D)J sequence.

Any of the RCA products disclosed herein, including those shown in FIG. 5A, FIG. 5B, and FIG. 6, can be analyzed in situ using SBL in order to detect the V(D)J join or a sequence thereof in the RCA product.

In some embodiments, the detection or determination comprises hybridizing one or more detectable probes to the probe (e.g., described in Section IV) or amplification products thereof (e.g., described in Section V). In some embodiments, the in situ detection herein can comprise sequential hybridization, e.g., sequencing by hybridization and/or sequential in situ fluorescence hybridization. Sequential fluorescence hybridization can involve sequential hybridization of the detectable probes disclosed herein. In some embodiments, a method disclosed herein comprises sequential hybridization of the detectable probes disclosed herein, including detectably labeled probes and/or detectable probes that are not detectably labeled per se but are capable of binding (e.g., via nucleic acid hybridization) and being detected by detectably labeled probes, such as detectable probes comprising detection regions capable of hybridizing to fluorescently labeled probes. Exemplary methods comprising sequential fluorescence hybridization of detectable probes are described in US 2019/0161796, US 2020/0224244, US 2022/0010358, US 2021/0340618, US 2022/0064697, and US 2023/0039899, all of which are incorporated herein by reference.

In some embodiments, the detection or determination comprises detecting V(D)J joins or a sequence thereof in a temporally sequential manner for in situ analysis in a biological sample, e.g., in an intact tissue. In some aspects, provided herein is a method for detecting the detectably labeled probes, thereby generating a signal code. In some instances, each signal code corresponds to a V(D)J sequence. In some instances, the probes may be optically detected (e.g., by detectably labeled probes) in a temporally-sequential manner. In some embodiments, the sample is contacted with a library of probes to detect the probes or products thereof (e.g., used or generated as described in Section IV) associated with the VDJ join in each different antigen receptor transcript. For example, each V(D)J joins or a sequence thereof is assigned a different signal code sequence and corresponds to an oligonucleotide of a library of oligonucleotides (e.g., a gapfill oligonucleotide from a library (e.g., described in Section IV)). In some instances, the probes or probe sets comprising various probe types may be applied to a sample simultaneously. In some instances, the probes or probe sets comprising various probe types may be applied to a sample sequentially. In some aspects, the method comprises sequential hybridization of labelled probes to create a spatiotemporal signal code that identifies the V(D)J sequence or portion thereof. In some instances, each gapfill oligonucleotide from a library (e.g., described in Section IV) is associated with a different spatiotemporal signal code.

In some embodiments, provided herein is a method of analyzing a sample, comprising: a) producing an RCA product in the sample, the RCA product comprising multiple copies of a V(D)J sequence, wherein the V(D)J sequence corresponds to a gapfill oligonucleotide sequence and is assigned a signal code sequence, and wherein the sample is a cell or tissue sample; b) contacting the sample with a first detectable probe (e.g., a detectable probe shown in FIG. 5B) and a first detectably labeled probe (e.g., a detectably labeled probe shown in FIG. 5B) to generate a first complex comprising the first detectable probe hybridized to the RCA product and the first detectably labeled probe hybridized to the first detectable probe, wherein the first detectable probe comprises (i) a hybridization region complementary to the V(D)J sequence and (ii) a first overhang sequence, and wherein the first detectably labeled probe comprises (i) a sequence complementary to the first overhang sequence and (ii) a first optically detectable moiety; c) imaging the sample to detect a first signal from the first optically detectable moiety, wherein the first signal corresponds to a first signal code in the signal code sequence; d) contacting the sample with a second detectable probe and a second detectably labeled probe to generate a second complex comprising the second detectable probe hybridized to the RCA product and the second detectably labeled probe hybridized to the second detectable probe, wherein the second detectable probe comprises (i) a hybridization region complementary to the V(D)J sequence and (ii) a second overhang sequence, and wherein the second detectably labeled probe comprises (i) a sequence complementary to the second overhang sequence and (ii) a second optically detectable moiety; and e) imaging the sample to detect a second signal from the second optically detectable moiety, wherein the second signal corresponds to a second signal code in the signal code sequence, wherein the signal code sequence comprising at least the first signal code and the second signal code is determined at a location in the sample, thereby decoding and identifying the V(D)J sequence at the location in the sample.

In some embodiments, the V(D)J sequence is among a plurality of V(D)J sequences, wherein the method comprises contacting the sample with a first pool of detectable probes and a universal pool of detectably labeled probes, wherein the first pool of detectable probes comprises the first detectable probe and the universal pool of detectably labeled probes comprises the first detectably labeled probe and the second detectably labeled probe, wherein each detectable probe in the first pool of detectable probes comprises (i) a hybridization region complementary to one of the plurality of V(D)J sequences and (ii) an overhang sequence complementary to a detectably labeled probe of the universal pool of detectably labeled probes; and the method comprises contacting the sample with a second pool of detectable probes and the universal pool of detectably labeled probes, wherein the second pool of detectable probes comprises the second detectable probe, and wherein each detectable probe in the second pool of detectable probes comprises (i) a hybridization region complementary to one of the plurality of V(D)J sequences and (ii) an overhang sequence complementary to a detectably labeled probe of the universal pool of detectably labeled probes.

In some embodiments, the method comprises identifying multiple different V(D)J sequences present at locations in the sample, wherein each different V(D)J sequence is assigned a different signal code sequence and is targeted by a circularizable probe or probe set and a gapfill oligonucleotide comprising a complement of a different V(D)J sequence of the plurality of V(D)J sequences. In some embodiments, the number of different detectable probes in each pool of detectable probes is greater than the number of different detectably labeled probes in the universal pool of detectably labeled probes. In some embodiments, the number of different detectably labeled probes in the universal pool of reporter probes is four. In some embodiments, the number of different detectable probes in each pool of detectable probes is about 10, about 20, about 50, about 100, about 200, about 500, about 1,000, about 2,000, about 5,000, or more.

In some embodiments, the different detectable probes in a pool of detectable probes correspond to a library of gapfill oligonucleotides, e.g., as described in Section IV-B. In some embodiments, the recognition sequence of a detectable probe is complementary to the V(D)J sequence in an RCA product and is the same as the corresponding V(D)J sequence in a cDNA which is used as a template to circularize the circularizable probe for the RCA. In some embodiments, the recognition sequence of a detectable probe comprises a sequence that is the same as the gapfill oligonucleotide sequence used to fill the gap of the circularizable probe hybridized to the cDNA. As such, in some embodiments, the recognition sequence of a detectable probe comprises a sequence that is the same as the V(D)J sequences in the antigen receptor transcript from which the cDNA is generated. An example in shown in FIG. 5B, where the recognition sequence of the detectable probe comprises a gapfill oligonucleotide sequence complementary to the VDJ join sequence in the cDNA.

Provided herein are methods involving the use of one or more probes (e.g., a detectable probe) for analyzing one or more target nucleic acid(s), such as V(D)J sequences in antigen receptor transcripts present in a cell or a biological sample, such as a tissue sample. In some aspects, the provided embodiments can be employed for in situ detection of V(D)J sequences in antigen receptor transcripts in a cell, e.g., in cells of a biological sample or a sample derived from a biological sample, such as a tissue section on a solid support, such as on a transparent slide.

In some aspects, provided herein are in situ assays using microscopy as a readout, e.g., hybridization, or other detection or determination methods involving an optical readout. In some aspects, detection or determination of a sequence of one, two, three, four, five, or more nucleotides of a V(D)J sequence in an antigen receptor transcript is performed in situ in a cell in an intact tissue. In some aspects, detection or determination of a sequence is performed such that the localization of the antigen receptor transcript (or product or a derivative thereof associated with the antigen receptor transcript) in the originating sample is detected. In some embodiments, the assay comprises detecting the presence or absence of an amplification product or a portion thereof (e.g., RCA product or hybridization complex). In some embodiments, a method for spatially profiling antigen receptor transcripts or a subset thereof in a biological sample is provided. In some embodiments, a provided method is quantitative and preserves the spatial information within a tissue sample without physically isolating cells or using homogenates. In some embodiments, the present disclosure provides methods for high-throughput profiling antigen receptor transcripts in situ in a large number of cells, tissues, organs or organisms.

In some aspects, the provided methods comprise imaging the amplification product (e.g., RCA product) via binding of the detectable probe and detecting the detectable label. In some embodiments, the detectable probe comprises a detectable label or binds a detectably labeled oligonucleotide that can be measured and quantitated. The terms "label" and "detectable label" comprise a directly or indirectly detectable moiety that is associated with (e.g., conjugated to) a molecule to be detected, e.g., a detectable probe, comprising, but not limited to, fluorophores, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like.

The term "fluorophore" comprises a substance or a portion thereof that is capable of exhibiting fluorescence in the detectable range. Particular examples of labels that may be used in accordance with the provided embodiments comprise, but are not limited to phycoerythrin, Alexa dyes, fluorescein, YPet, CyPet, Cascade blue, allophycocyanin, Cy3, Cy5, Cy7, rhodamine, dansyl, umbelliferone, Texas red, luminol, acradimum esters, biotin, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), firefly luciferase, *Renilla* luciferase, NADPH, beta-galactosidase, horseradish peroxidase, glucose oxidase, alkaline phosphatase, chloramphenical acetyl transferase, and urease.

Fluorescence detection in tissue samples can often be hindered by the presence of strong background fluorescence. "Autofluorescence" is the general term used to distinguish background fluorescence (that can arise from a variety of sources, including aldehyde fixation, extracellular matrix components, red blood cells, lipofuscin, and the like) from the desired immunofluorescence from the fluorescently labeled antibodies or probes. Tissue autofluorescence can lead to difficulties in distinguishing the signals due to fluorescent antibodies or probes from the general background. In some embodiments, a method disclosed herein utilizes one or more agents to reduce tissue autofluorescence, for example, Autofluorescence Eliminator (Sigma/EMD Millipore), TrueBlack Lipofuscin Autofluorescence Quencher (Biotium), MaxBlock Autofluorescence Reducing Reagent Kit (MaxVision Biosciences), and/or a very intense black dye (e.g., Sudan Black, or comparable dark chromophore).

Examples of detectable labels comprise but are not limited to various radioactive moieties, enzymes, prosthetic groups, fluorescent markers, luminescent markers, bioluminescent markers, metal particles, protein-protein binding pairs and protein-antibody binding pairs. Examples of fluorescent proteins comprise, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride and phycoerythrin.

Examples of bioluminescent markers comprise, but are not limited to, luciferase (e.g., bacterial, firefly and click beetle), luciferin, aequorin and the like. Examples of enzyme systems having visually detectable signals comprise, but are not limited to, galactosidases, glucorimidases, phosphatases, peroxidases and cholinesterases. Identifiable markers also comprise radioactive compounds such as $^{125}$I, $^{35}$S, $^{14}$C, or $^{3}$H. Identifiable markers are commercially available from a variety of sources.

Examples of fluorescent labels and nucleotides and/or polynucleotides conjugated to such fluorescent labels comprise those described in, for example, Hoagland, Handbook of Fluorescent Probes and Research Chemicals, Ninth Edition (Molecular Probes, Inc., Eugene, 2002); Keller and Manak, DNA Probes, 2nd Edition (Stockton Press, New York, 1993); Eckstein, editor, Oligonucleotides and Analogues: A Practical Approach (IRL Press, Oxford, 1991); and Wetmur, Critical Reviews in Biochemistry and Molecular Biology, 26:227-259 (1991), all of which are herein incorporated by reference in their entireties. In some embodiments, exemplary techniques and methods methodologies applicable to the provided embodiments comprise those described in, for example, U.S. Pat. Nos. 4,757,141, 5,151, 507 and 5,091,519 both of which are herein incorporated by reference in their entireties. In some embodiments, one or more fluorescent dyes are used as labels for labeled target sequences, for example, as described in U.S. Pat. No. 5,188,934 (4,7-dichlorofluorescein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); U.S. Pat. No. 5,066,580 (xanthine dyes); and U.S. Pat. No. 5,688,648 (energy transfer dyes), all of which are herein incorporated by reference in their entireties. Labelling can also be carried out with quantum dots, as described in U.S. Pat. Nos. 6,322,901, 6,576,291, 6,423,551, 6,251,303, 6,319,426, 6,426,513, 6,444,143, 5,990,479, 6,207,392, US 2002/0045045 and US 2003/0017264, all of which are herein incorporated by reference in their entireties. In some embodiments, fluorescent label comprises a signaling moiety that conveys information through the fluorescent absorption and/or emission properties of one or more molecules. Exemplary fluorescent properties comprise fluorescence intensity, fluorescence lifetime, emission spectrum characteristics and energy transfer.

In some embodiments, the detectable probe comprises one or more detectably labelled, e.g., fluorescent, nucleotides. In some embodiments, the one or more detectably labelled nucleotides are incorporated into the concatemeric region of the detectable probe during generation of the detectable probe, e.g., during RCA. Examples of commercially available fluorescent nucleotide analogues readily incorporated into nucleotide and/or polynucleotide sequences comprise, but are not limited to, Cy3-dCTP, Cy3-dUTP, Cy5-dCTP, Cy5-dUTP (Amersham Biosciences, Piscataway, N.J.), fluorescein-12-dUTP, tetramethylrhodamine-6-dUTP, TEXAS RED™-5-dUTP, CASCADE BLUE™-7-dUTP, BODIPY TMFL-14-dUTP, BODIPY TMR-14-dUTP, BODIPY TMTR-14-dUTP, RHOD AMINE GREEN™-5-dUTP, OREGON GREENR™ 488-5-dUTP, TEXAS RED™-12-dUTP, BODIPY™ 630/650-14-dUTP, BODIPY™ 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethyl-rhodamine-6-UTP, TEXAS RED™-5-UTP, mCherry, CASCADE BLUE™-7-UTP, BODIPY™ FL-14-UTP, BODIPY TMR-14-UTP, BODIPY™ TR-14-UTP, RHOD AMINE GREEN™-5-UTP, ALEXA FLUOR™ 488-5-UTP, and ALEXA FLUOR™ 546-14-UTP (Molecular Probes, Inc. Eugene, Oreg.). For exemplary methods for custom synthesis of nucleotides having other fluorophores, see, Henegariu et al. (2000) Nature Biotechnol. 18:345.

Other fluorophores available for post-synthetic attachment comprise, but are not limited to, ALEXA FLUOR™ 350, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, Texas Red (available from Molecular Probes, Inc., Eugene, Oreg.), Cy2, Cy3.5, Cy5.5, and Cy7 (Amersham Biosciences, Piscataway, N.J.). FRET tandem fluorophores may also be used, comprising, but not limited to, PerCP-Cy5.5, PE-Cy5, PE-Cy5.5, PE-Cy7, PE-Texas Red, APC-Cy7, PE-Alexa dyes (610, 647, 680), and APC-Alexa dyes.

In some cases, metallic silver or gold particles may be used to enhance signal from fluorescently labeled nucleotide and/or polynucleotide sequences (Lakowicz et al. (2003) Bio Techniques 34:62, the content of which is herein incorporated by reference in its entirety).

Biotin, or a derivative thereof, may also be used as a label on a nucleotide and/or a polynucleotide sequence, and subsequently bound by a detectably labeled avidin/streptavidin derivative (e.g., phycoerythrin-conjugated streptavidin), or a detectably labeled anti-biotin antibody. Digoxigenin may be incorporated as a label and subsequently bound by a detectably labeled anti-digoxigenin antibody (e.g., fluoresceinated anti-digoxigenin). An aminoallyl-dUTP residue may be incorporated into a polynucleotide sequence and subsequently coupled to an N-hydroxy succinimide (NHS) derivatized fluorescent dye. In general, any member of a conjugate pair may be incorporated into a detection polynucleotide provided that a detectably labeled conjugate partner can be bound to permit detection. As used herein, the term antibody refers to an antibody molecule of any class, or any sub-fragment thereof, such as a Fab.

Other suitable labels for a polynucleotide sequence may comprise fluorescein (FAM), digoxigenin, dinitrophenol (DNP), dansyl, biotin, bromodeoxyuridine (BrdU), hexahistidine (6×His), and phosphor-amino acids (e.g., P-tyr, P-ser, P-thr). In some embodiments the following hapten/antibody pairs are used for detection, in which each of the antibodies is derivatized with a detectable label: biotin/a-biotin, digoxigenin/a-digoxigenin, dinitrophenol (DNP)/a-DNP, 5-Carboxyfluorescein (FAM)/a-FAM.

In some embodiments, a nucleotide and/or an polynucleotide sequence can be indirectly labeled, especially with a hapten that is then bound by a capture agent, e.g., as disclosed in U.S. Pat. Nos. 5,344,757, 5,702,888, 5,354,657, 5,198,537 and 4,849,336, and PCT publication WO 91/17160, all of which are herein incorporated by reference in their entireties. Many different hapten-capture agent pairs are available for use. Exemplary haptens comprise, but are not limited to, biotin, des-biotin and other derivatives, dinitrophenol, dansyl, fluorescein, Cy5, and digoxigenin. For biotin, a capture agent may be avidin, streptavidin, or antibodies. Antibodies may be used as capture agents for the other haptens (many dye-antibody pairs being commercially available, e.g., Molecular Probes, Eugene, Oreg.).

In some aspects, the detecting involves using detection methods such as flow cytometry; sequencing; probe binding and electrochemical detection; pH alteration; catalysis induced by enzymes bound to DNA tags; quantum entanglement; Raman spectroscopy; terahertz wave technology; and/or scanning electron microscopy. In some aspects, the flow cytometry is mass cytometry or fluorescence-activated flow cytometry. In some aspects, the detecting comprises performing microscopy, scanning mass spectrometry or other imaging techniques described herein. In such aspects, the detecting comprises determining a signal, e.g., a fluorescent signal.

In some aspects, the detection (comprising imaging) is carried out using any of a number of different types of microscopy, e.g., confocal microscopy, two-photon microscopy, light-field microscopy, intact tissue expansion microscopy, and/or CLARITY™-optimized light sheet microscopy (COLM).

In some embodiments, fluorescence microscopy is used for detection and imaging of the detectable probe and/or a detectably labeled oligonucleotide bound thereto. In some aspects, a fluorescence microscope is an optical microscope that uses fluorescence and phosphorescence instead of, or in addition to, reflection and absorption to study properties of organic or inorganic substances. In fluorescence microscopy, a sample is illuminated with light of a wavelength which excites fluorescence in the sample. The fluoresced light, which is usually at a longer wavelength than the illumination, is then imaged through a microscope objective. Two filters may be used in this technique; an illumination (or excitation) filter which ensures the illumination is near monochromatic and at the correct wavelength, and a second emission (or barrier) filter which ensures none of the excitation light source reaches the detector. Alternatively, these functions may both be accomplished by a single dichroic filter. The "fluorescence microscope" comprises any microscope that uses fluorescence to generate an image, whether it is a more simple set up like an epifluorescence microscope, or a more complicated design such as a confocal microscope, which uses optical sectioning to get better resolution of the fluorescent image.

In some embodiments, confocal microscopy is used for detection and imaging of the detectable probe and/or a detectably labeled oligonucleotide bound thereto. Confocal microscopy uses point illumination and a pinhole in an optically conjugate plane in front of the detector to eliminate out-of-focus signal. As only light produced by fluorescence very close to the focal plane can be detected, the image's optical resolution, particularly in the sample depth direction, is much better than that of wide-field microscopes. However, as much of the light from sample fluorescence is blocked at the pinhole, this increased resolution is at the cost of decreased signal intensity—so long exposures are often required. As only one point in the sample is illuminated at a time, 2D or 3D imaging requires scanning over a regular raster (i.e., a rectangular pattern of parallel scanning lines) in the specimen. The achievable thickness of the focal plane is defined mostly by the wavelength of the used light divided by the numerical aperture of the objective lens, but also by the optical properties of the specimen. The thin optical sectioning possible makes these types of microscopes particularly good at 3D imaging and surface profiling of samples. CLARITY™-optimized light sheet microscopy (COLM) provides an alternative microscopy for fast 3D imaging of large clarified samples. COLM interrogates large immunostained tissues, permits increased speed of acquisition and results in a higher quality of generated data.

Other types of microscopy that can be employed comprise bright field microscopy, oblique illumination microscopy, dark field microscopy, phase contrast, differential interference contrast (DIC) microscopy, interference reflection microscopy (also known as reflected interference contrast, or RIC), single plane illumination microscopy (SPIM), super-resolution microscopy, laser microscopy, electron microscopy (EM), Transmission electron microscopy (TEM), Scanning electron microscopy (SEM), reflection electron microscopy (REM), Scanning transmission electron microscopy (STEM) and low-voltage electron microscopy (LVEM), scanning probe microscopy (SPM), atomic force microscopy (ATM), ballistic electron emission microscopy (BEEM), chemical force microscopy (CFM), conductive atomic force microscopy (C-AFM), electrochemical scanning tunneling microscope (ECS™), electrostatic force microscopy (EFM), fluidic force microscope (FluidFM), force modulation microscopy (FMM), feature-oriented scanning probe microscopy (FOSPM), kelvin probe force microscopy (KPFM), magnetic force microscopy (MFM), magnetic resonance force microscopy (MRFM), near-field scanning optical microscopy (NSOM) (or SNOM, scanning near-field optical microscopy, SNOM, Piezoresponse Force Microscopy (PFM), PS™, photon scanning tunneling microscopy (PS™), PTMS, photothermal microspectroscopy/microscopy (PTMS), SCM, scanning capacitance microscopy (SCM), SECM, scanning electrochemical microscopy (SECM), SGM, scanning gate microscopy (SGM), SHPM, scanning Hall probe microscopy (SHPM), SICM, scanning ion-conductance microscopy (SICM), SPSM spin polarized scanning tunneling microscopy (SPSM), SSRM, scanning spreading resistance microscopy (SSRM), SThM, scanning thermal microscopy (SThM), STM, scanning tunneling microscopy (STM), STP, scanning tunneling potentiometry (STP), SVM, scanning voltage microscopy (SVM), and synchrotron x-ray scanning tunneling microscopy (SXS™), and intact tissue expansion microscopy (exM).

VII. Samples and Sample Processing

A sample disclosed herein can be derived from any biological sample. The sample may not be limited to any specific source, but may be peripheral blood mononuclear cells, tumors, tissue, bone marrow, biopsies, serum, blood, plasma, saliva, lymph fluid, pleura fluid, cerebrospinal and synovial fluid. The sample may be extracted from a subject. Samples extracted from individuals may be subjected to the methods described herein to identify and evaluate immune responses during cancer and disease or subsequent to immunotherapy. In the present context, the term "sample" refers to any solution or solid fraction that comprises a population of immune cells (e.g., T cells). The T cell population may contain multiple clones of T cells with different antigen specificities.

Methods and compositions disclosed herein may be used for analyzing a biological sample, which may be obtained from a subject using any of a variety of techniques including, but not limited to, biopsy, surgery, and laser capture microscopy (LCM), and generally includes cells and/or other biological material from the subject. A biological sample can also be obtained from a eukaryote, such as a tissue sample, a patient derived organoid (PDO) or patient derived xenograft (PDX). A biological sample from an organism may comprise one or more other organisms or components therefrom. For example, a mammalian tissue section may comprise a prion, a viroid, a virus, a bacterium, a fungus, or components from other organisms, in addition to mammalian cells and non-cellular tissue components.

Subjects from which biological samples can be obtained can be healthy or asymptomatic individuals, individuals that have or are suspected of having a disease (e.g., a patient with a disease such as cancer) or a pre-disposition to a disease, and/or individuals in need of therapy or suspected of needing therapy.

In some embodiments, the biological sample corresponds to cells (e.g., derived from a cell culture, a tissue sample, or cells deposited on a surface). In a cell sample with a plurality of cells, individual cells can be naturally unaggregated. For example, the cells can be derived from a suspension of cells (e.g., a body fluid such as blood) and/or disassociated or disaggregated cells from a tissue or tissue section. The number of cells in the biological sample can vary. Some biological samples comprise large numbers of cells, e.g., blood samples, while other biological samples comprise smaller or only a small number of cells or may only be suspected of containing cells, e.g., plasma, serum, urine, saliva, synovial fluids, amniotic fluid, lachrymal fluid, lymphatic fluid, liquor, cerebrospinal fluid and the like.

In some embodiments, a cell-containing biological sample can comprise a body fluid or a cell-containing sample derived from the body fluid, e.g., whole blood, samples derived from blood such as plasma or serum, buffy coat, urine, sputum, lachrymal fluid, lymphatic fluid, sweat, liquor, cerebrospinal fluid, ascites, milk, stool, bronchial lavage, saliva, amniotic fluid, nasal secretions, vaginal secretions, semen/seminal fluid, wound secretions, cell culture and swab samples, or any cell-containing sample derived from the aforementioned samples. In some embodiments, a cell-containing biological sample can be a body fluid, a body secretion or body excretion, e.g., lymphatic fluid, blood, buffy coat, plasma or serum. In some embodiments, a cell-containing biological sample can be a circulating body fluid such as blood or lymphatic fluid, e.g., peripheral blood obtained from a mammal such as human.

The biological sample can include any number of macromolecules, for example, cellular macromolecules and organelles (e.g., mitochondria and nuclei). The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions. In some embodiments, the biological sample may comprise cells which are deposited on a surface. In some embodiments, a biological sample disclosed herein can be or comprise a portion of a tissue sample (e.g., an FFPE tissue block), a cell pellet, or a cell block. In some embodiments, the biological sample may comprises transcripts of antigen receptor molecules.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells. Biological samples can also include fetal cells and immune cells.

Biological samples can include analytes (e.g., protein, RNA, and/or DNA) embedded in a 3D matrix. In some embodiments, amplicons (e.g., rolling circle amplification products) derived from or associated with analytes (e.g., protein, RNA, and/or DNA) can be embedded in a 3D matrix. In some embodiments, a 3D matrix may comprise a network of natural molecules and/or synthetic molecules that are chemically and/or enzymatically linked, e.g., by crosslinking. In some embodiments, a 3D matrix may comprise a synthetic polymer. In some embodiments, a 3D matrix comprises a hydrogel.

In some embodiments, a substrate herein can be any support that is insoluble in aqueous liquid and which allows for positioning of biological samples, analytes, features, and/or reagents (e.g., probes) on the support. In some embodiments, a biological sample can be attached to a substrate. Attachment of the biological sample can be irreversible or reversible, depending upon the nature of the sample and subsequent steps in the analytical method. In certain embodiments, the sample can be attached to the substrate reversibly by applying a suitable polymer coating to the substrate, and contacting the sample to the polymer coating. The sample can then be detached from the substrate, e.g., using an organic solvent that at least partially dissolves the polymer coating. Hydrogels are examples of polymers that are suitable for this purpose.

In some embodiments, the substrate can be coated or functionalized with one or more substances to facilitate attachment of the sample to the substrate. Suitable substances that can be used to coat or functionalize the substrate include, but are not limited to, lectins, polylysine, antibodies, and polysaccharides.

A variety of steps can be performed to prepare or process a biological sample for and/or during an assay. Except where indicated otherwise, the preparative or processing steps described below can generally be combined in any manner and in any order to appropriately prepare or process a particular sample for and/or analysis.

(i) Tissue Sectioning

A biological sample can be harvested from a subject (e.g., via surgical biopsy, whole subject sectioning) or grown in vitro on a growth substrate or culture dish as a population of cells, and prepared for analysis as a tissue slice or tissue section. Grown samples may be sufficiently thin for analysis without further processing steps. Alternatively, grown samples, and samples obtained via biopsy or sectioning, can be prepared as thin tissue sections using a mechanical cutting apparatus such as a vibrating blade microtome. As another alternative, in some embodiments, a thin tissue section can be prepared by applying a touch imprint of a biological sample to a suitable substrate material.

The thickness of the tissue section can be a fraction of (e.g., less than 0.9, 0.8, 0.7, 0.6, 0.5, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 µm thick.

More generally, the thickness of a tissue section typically depends on the method used to prepare the section and the physical characteristics of the tissue, and therefore sections having a wide variety of different thicknesses can be prepared and used. For example, the thickness of the tissue section can be at least 0.1, 0.2, 0.3, 0.4, 0.5, 0.7, 1.0, 1.5, 2, 3, 4, 5, 6, 7, 8, 9, 10, 12, 13, 14, 15, 20, 30, 40, or 50 µm. Thicker sections can also be used if desired or convenient, e.g., at least 70, 80, 90, or 100 µm or more. Typically, the thickness of a tissue section is between 1-100 µm, 1-50 µm, 1-30 µm, 1-25 µm, 1-20 µm, 1-15 µm, 1-10 µm, 2-8 µm, 3-7 µm, or 4-6 µm, but as mentioned above, sections with thicknesses larger or smaller than these ranges can also be analysed.

Multiple sections can also be obtained from a single biological sample. For example, multiple tissue sections can be obtained from a surgical biopsy sample by performing serial sectioning of the biopsy sample using a sectioning blade. Spatial information among the serial sections can be preserved in this manner, and the sections can be analysed successively to obtain three-dimensional information about the biological sample.

(ii) Freezing

In some embodiments, the biological sample (e.g., a tissue section as described above) can be prepared by deep freezing at a temperature suitable to maintain or preserve the integrity (e.g., the physical characteristics) of the tissue structure. The frozen tissue sample can be sectioned, e.g., thinly sliced, onto a substrate surface using any number of suitable methods. For example, a tissue sample can be prepared using a chilled microtome (e.g., a cryostat) set at a temperature suitable to maintain both the structural integrity of the tissue sample and the chemical properties of the nucleic acids in the sample. Such a temperature can be, e.g., less than –15° C., less than –20° C., or less than –25° C.

(iii) Fixation and Postfixation

In some embodiments, the biological sample can be prepared using formalin-fixation and paraffin-embedding (FFPE), which are established methods. In some embodiments, cell suspensions and other non-tissue samples can be prepared using formalin-fixation and paraffin-embedding. Following fixation of the sample and embedding in a paraffin or resin block, the sample can be sectioned as described above. Prior to analysis, the paraffin-embedding material can be removed from the tissue section (e.g., deparaffinization) by incubating the tissue section in an appropriate solvent (e.g., xylene) followed by a rinse (e.g., 99.5% ethanol for 2 minutes, 96% ethanol for 2 minutes, and 70% ethanol for 2 minutes).

As an alternative to formalin fixation described above, a biological sample can be fixed in any of a variety of other fixatives to preserve the biological structure of the sample prior to analysis. For example, a sample can be fixed via immersion in ethanol, methanol, acetone, paraformaldehyde (PFA)-Triton, and combinations thereof.

In some embodiments, acetone fixation is used with fresh frozen samples, which can include, but are not limited to, cortex tissue, mouse olfactory bulb, human brain tumor, human post-mortem brain, and breast cancer samples. When acetone fixation is performed, pre-permeabilization steps (described below) may not be performed. Alternatively, acetone fixation can be performed in conjunction with permeabilization steps.

In some embodiments, the methods provided herein comprises one or more post-fixing (also referred to as postfixation) steps. In some embodiments, one or more post-fixing step is performed after contacting a sample with a polynucleotide disclosed herein, e.g., one or more probes such as a circular or circularizable probe (e.g., padlock probe). In some embodiments, one or more post-fixing step is performed after a hybridization complex comprising a probe and a target is formed in a sample. In some embodiments, one or more post-fixing step is performed prior to a ligation reaction disclosed herein, such as the ligation to circularize a circularizable probe or probe set (e.g., padlock probe).

In some embodiments, one or more post-fixing step is performed after contacting a sample with a binding or labelling agent (e.g., an antibody or antigen binding fragment thereof) for a non-nucleic acid analyte such as a protein analyte. The labelling agent can comprise a nucleic acid molecule (e.g., reporter oligonucleotide) comprising a sequence corresponding to the labelling agent and therefore corresponds to (e.g., uniquely identifies) the analyte. In some embodiments, the labelling agent can comprise a reporter oligonucleotide comprising one or more barcode sequences.

A post-fixing step may be performed using any suitable fixation reagent disclosed herein, for example, 3% (w/v) paraformaldehyde in DEPC-PBS.

(iv) Embedding

As an alternative to paraffin embedding described above, a biological sample can be embedded in any of a variety of other embedding materials to provide structural substrate to the sample prior to sectioning and other handling steps. In some cases, the embedding material can be removed e.g., prior to analysis of tissue sections obtained from the sample. Suitable embedding materials include, but are not limited to, waxes, resins (e.g., methacrylate resins), epoxies, and agar.

In some embodiments, the biological sample can be embedded in a matrix (e.g., a hydrogel matrix). Embedding the sample in this manner typically involves contacting the biological sample with a hydrogel such that the biological sample becomes surrounded by the hydrogel. For example, the sample can be embedded by contacting the sample with a suitable polymer material, and activating the polymer material to form a hydrogel. In some embodiments, the hydrogel is formed such that the hydrogel is internalized within the biological sample.

In some embodiments, the biological sample is immobilized in the hydrogel via cross-linking of the polymer material that forms the hydrogel. Cross-linking can be performed chemically and/or photochemically, or alternatively by any other suitable method of hydrogel-formation.

The composition and application of the hydrogel-matrix to a biological sample typically depends on the nature and preparation of the biological sample (e.g., sectioned, non-sectioned, type of fixation). As one example, where the biological sample is a tissue section, the hydrogel-matrix can include a monomer solution and an ammonium persulfate (APS) initiator/tetramethylethylenediamine (TEMED) accelerator solution. As another example, where the biological sample consists of cells (e.g., cultured cells or cells disassociated from a tissue sample), the cells can be incubated with the monomer solution and APS/TEMED solutions. For cells, hydrogel-matrix gels are formed in compartments, including but not limited to devices used to culture, maintain, or transport the cells. For example, hydrogel-matrices can be formed with monomer solution plus APS/TEMED added to the compartment to a depth ranging from about 0.1 µm to about 2 mm.

Additional methods and aspects of hydrogel embedding of biological samples are described for example in Chen et al., Science 347(6221):543-548, 2015, the entire contents of which are incorporated herein by reference.

(v) Staining and Immunohistochemistry (IHC)

To facilitate visualization, biological samples can be stained using a wide variety of stains and staining techniques. In some embodiments, for example, a sample can be stained using any number of stains and/or immunohistochemical reagents. One or more staining steps may be performed to prepare or process a biological sample for an assay described herein or may be performed during and/or after an assay. In some embodiments, the sample can be contacted with one or more nucleic acid stains, membrane stains (e.g., cellular or nuclear membrane), cytological stains, or combinations thereof. In some examples, the stain may be specific to proteins, phospholipids, DNA (e.g., dsDNA, ssDNA), RNA, an organelle or compartment of the cell. The sample may be contacted with one or more labeled antibodies (e.g., a primary antibody specific for the analyte of interest and a labeled secondary antibody specific for the primary antibody). In some embodiments, cells in the sample can be segmented using one or more images taken of the stained sample.

In some embodiments, the stain is performed using a lipophilic dye. In some examples, the staining is performed with a lipophilic carbocyanine or aminostyryl dye, or analogs thereof (e.g, DiI, DiO, DiR, DiD). Other cell membrane stains may include FM and RH dyes or immunohistochemical reagents specific for cell membrane proteins. In some examples, the stain may include but is not limited to, acridine orange, acid fuchsin, Bismarck brown, carmine, Coomassie blue, cresyl violet, DAPI, eosin, ethidium bromide, acid fuchsine, haematoxylin, Hoechst stains, iodine, methyl green, methylene blue, neutral red, Nile blue, Nile red, osmium tetroxide, ruthenium red, propidium iodide, rhodamine (e.g., rhodamine B), or safranine, or derivatives thereof. In some embodiments, the sample may be stained with haematoxylin and eosin (H&E).

The sample can be stained using hematoxylin and eosin (H&E) staining techniques, using Papanicolaou staining techniques, Masson's trichrome staining techniques, silver staining techniques, Sudan staining techniques, and/or using Periodic Acid Schiff (PAS) staining techniques. PAS staining is typically performed after formalin or acetone fixation. In some embodiments, the sample can be stained using Romanowsky stain, including Wright's stain, Jenner's stain, Can-Grunwald stain, Leishman stain, and Giemsa stain.

In some embodiments, biological samples can be destained. Any suitable methods of destaining or discoloring a biological sample may be utilized, and generally depend on the nature of the stain(s) applied to the sample. For example, in some embodiments, one or more immunofluorescent stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., *J. Histochem. Cytochem.* 2017; 65(8): 431-444, Lin et al., *Nat Commun.* 2015; 6:8390, Pirici et al., *J. Histochem. Cytochem.* 2009; 57:567-75, and Glass et al., *J. Histochem. Cytochem.* 2009; 57:899-905, the entire contents of each of which are incorporated herein by reference.

(vi) Isometric Expansion

In some embodiments, a biological sample embedded in a matrix (e.g., a hydrogel) can be isometrically expanded. Isometric expansion methods that can be used include hydration, a preparative step in expansion microscopy, as described in Chen et al., *Science* 347(6221):543-548, 2015, the content of which is herein incorporated by reference in its entirety.

Isometric expansion can be performed by anchoring one or more components of a biological sample to a gel, followed by gel formation, proteolysis, and swelling. In some embodiments, analytes in the sample, products of the analytes, and/or probes associated with analytes in the sample can be anchored to the matrix (e.g., hydrogel). Isometric expansion of the biological sample can occur prior to immobilization of the biological sample on a substrate, or after the biological sample is immobilized to a substrate. In some embodiments, the isometrically expanded biological sample can be removed from the substrate prior to contacting the substrate with probes disclosed herein.

In general, the steps used to perform isometric expansion of the biological sample can depend on the characteristics of the sample (e.g., thickness of tissue section, fixation, cross-linking), and/or the analyte of interest (e.g., different conditions to anchor RNA, DNA, and protein to a gel).

In some embodiments, proteins in the biological sample are anchored to a swellable gel such as a polyelectrolyte gel. An antibody can be directed to the protein before, after, or in conjunction with being anchored to the swellable gel. DNA and/or RNA in a biological sample can also be anchored to the swellable gel via a suitable linker. Examples of such linkers include, but are not limited to, 6-((Acryloyl) amino) hexanoic acid (Acryloyl-X SE) (available from ThermoFisher, Waltham, MA), Label-IT Amine (available from MirusBio, Madison, WI) and Label X (described for example in Chen et al., Nat. Methods 13:679-684, 2016, the entire contents of which are incorporated herein by reference).

Isometric expansion of the sample can increase the spatial resolution of the subsequent analysis of the sample. The increased resolution in spatial profiling can be determined by comparison of an isometrically expanded sample with a sample that has not been isometrically expanded.

In some embodiments, a biological sample is isometrically expanded to a size at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded size. In some embodiments, the sample is isometrically expanded to at least 2× and less than 20× of its non-expanded size.

(vii) Crosslinking and De-Crosslinking

In some embodiments, the biological sample is reversibly cross-linked prior to or during an in situ assay. In some aspects, the analytes, polynucleotides and/or amplification product (e.g., amplicon) of an analyte or a probe bound thereto can be anchored to a polymer matrix. For example, the polymer matrix can be a hydrogel. In some embodiments, one or more of the polynucleotide probe(s) and/or amplification product (e.g., amplicon) thereof can be modified to contain functional groups that can be used as an anchoring site to attach the polynucleotide probes and/or amplification product to a polymer matrix. In some embodiments, a modified probe comprising oligo dT may be used to bind to mRNA molecules of interest, followed by reversible crosslinking of the mRNA molecules.

In some embodiments, the biological sample is immobilized in a hydrogel via cross-linking of the polymer material that forms the hydrogel. Cross-linking can be performed chemically and/or photochemically, or alternatively by any other suitable hydrogel-formation method. A hydrogel may include a macromolecular polymer gel including a network. Within the network, some polymer chains can optionally be cross-linked, although cross-linking does not always occur.

In some embodiments, a hydrogel can include hydrogel subunits, such as, but not limited to, acrylamide, bis-acrylamide, polyacrylamide and derivatives thereof, poly(ethylene glycol) and derivatives thereof (e.g., PEG-acrylate (PEG-DA), PEG-RGD), gelatin-methacryloyl (GelMA), methacrylated hyaluronic acid (MeHA), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose, and the like, and combinations thereof.

In some embodiments, a hydrogel includes a hybrid material, e.g., the hydrogel material includes elements of both synthetic and natural polymers. Examples of suitable hydrogels are described, for example, in U.S. Pat. Nos. 6,391,937, 9,512,422, and 9,889,422, and in U.S. Patent Application Publication Nos. 2017/0253918, 2018/0052081 and 2010/0055733, the entire contents of each of which are incorporated herein by reference.

In some embodiments, the hydrogel can form the substrate. In some embodiments, the substrate includes a hydrogel and one or more second materials. In some embodiments, the hydrogel is placed on top of one or more second materials. For example, the hydrogel can be pre-formed and then placed on top of, underneath, or in any other configuration with one or more second materials. In some embodiments, hydrogel formation occurs after contacting one or more second materials during formation of the substrate. Hydrogel formation can also occur within a structure (e.g., wells, ridges, projections, and/or markings) located on a substrate.

In some embodiments, hydrogel formation on a substrate occurs before, contemporaneously with, or after probes are provided to the sample. For example, hydrogel formation can be performed on the substrate already containing the probes.

In some embodiments, hydrogel formation occurs within a biological sample. In some embodiments, a biological sample (e.g., tissue section) is embedded in a hydrogel. In some embodiments, hydrogel subunits are infused into the biological sample, and polymerization of the hydrogel is initiated by an external or internal stimulus.

In embodiments in which a hydrogel is formed within a biological sample, functionalization chemistry can be used. In some embodiments, functionalization chemistry includes hydrogel-tissue chemistry (HTC). Any hydrogel-tissue backbone (e.g., synthetic or native) suitable for HTC can be used for anchoring biological macromolecules and modulating functionalization. Non-limiting examples of methods using HTC backbone variants include CLARITY, PACT, ExM, SWITCH and ePACT. In some embodiments, hydrogel formation within a biological sample is permanent. For example, biological macromolecules can permanently adhere to the hydrogel allowing multiple rounds of interrogation. In some embodiments, hydrogel formation within a biological sample is reversible.

In some embodiments, additional reagents are added to the hydrogel subunits before, contemporaneously with, and/or after polymerization. For example, additional reagents can include but are not limited to oligonucleotides (e.g., probes), endonucleases to fragment DNA, fragmentation buffer for DNA, DNA polymerase enzymes, dNTPs used to amplify the nucleic acid and to attach the barcode to the amplified fragments. Other enzymes can be used, including without limitation, RNA polymerase, ligase, proteinase K, and DNAse. Additional reagents can also include reverse transcriptase enzymes, including enzymes with terminal transferase activity, primers, and switch oligonucleotides. In some embodiments, optical labels are added to the hydrogel subunits before, contemporaneously with, and/or after polymerization.

In some embodiments, HTC reagents are added to the hydrogel before, contemporaneously with, and/or after polymerization. In some embodiments, a cell labelling agent is added to the hydrogel before, contemporaneously with, and/or after polymerization. In some embodiments, a cell-penetrating agent is added to the hydrogel before, contemporaneously with, and/or after polymerization.

Hydrogels embedded within biological samples can be cleared using any suitable method. For example, electrophoretic tissue clearing methods can be used to remove biological macromolecules from the hydrogel-embedded sample. In some embodiments, a hydrogel-embedded sample is stored before or after clearing of hydrogel, in a medium (e.g., a mounting medium, methylcellulose, or other semi-solid mediums).

In some embodiments, a method disclosed herein comprises de-crosslinking the reversibly cross-linked biological sample. The de-crosslinking does not need to be complete. In some embodiments, only a portion of crosslinked molecules in the reversibly cross-linked biological sample are de-crosslinked and allowed to migrate.

(viii) Tissue Permeabilization and Treatment

In some embodiments, a biological sample can be permeabilized to facilitate transfer of species (such as probes) into the sample. If a sample is not permeabilized sufficiently, the amount of species (such as probes) in the sample may be too low to enable adequate analysis. Conversely, if the tissue sample is too permeable, the relative spatial relationship of the analytes within the tissue sample can be lost. Hence, a balance between permeabilizing the tissue sample enough to obtain good signal intensity while still maintaining the spatial resolution of the analyte distribution in the sample is desirable.

In general, a biological sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, Triton X100™ or Tween-20™), and enzymes (e.g., trypsin, proteases). In some embodiments, the biological sample can be incubated with a cellular permeabilizing agent to facilitate permeabilization of the sample. Additional methods for sample permeabilization are described, for example, in Jamur et al., Method Mol. Biol. 588:63-66, 2010, the entire contents of which are incorporated herein by reference. Any suitable method for sample permeabilization can generally be used in connection with the samples described herein.

In some embodiments, the biological sample can be permeabilized by adding one or more lysis reagents to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes.

Other lysis agents can additionally or alternatively be added to the biological sample to facilitate permeabilization. For example, surfactant-based lysis solutions can be used to lyse sample cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

In some embodiments, the biological sample can be permeabilized by non-chemical permeabilization methods. Suitable non-chemical permeabilization methods can be used. For example, non-chemical permeabilization methods that can be used include, but are not limited to, physical lysis techniques such as electroporation, mechanical permeabilization methods (e.g., bead beating using a homogenizer and grinding balls to mechanically disrupt sample tissue structures), acoustic permeabilization (e.g., sonication), and thermal lysis techniques such as heating to induce thermal permeabilization of the sample.

Additional reagents can be added to a biological sample to perform various functions prior to analysis of the sample. In some embodiments, DNase and RNase inactivating agents or inhibitors such as proteinase K, and/or chelating agents such as EDTA, can be added to the sample. For example, a method disclosed herein may comprise a step for increasing accessibility of a nucleic acid for binding, e.g., a denaturation step to open up DNA in a cell for hybridization by a probe. For example, proteinase K treatment may be used to free up DNA with proteins bound thereto.

(ix) Selective Enrichment of RNA or cDNA Species

In some embodiments, where RNA or cDNA is the analyte, one or more RNA or cDNA analyte species of interest can be selectively enriched. For example, one or more species of RNA or cDNA of interest can be selected by addition of one or more oligonucleotides to the sample. In some embodiments, the additional oligonucleotide is a sequence used for priming a reaction by an enzyme (e.g., a polymerase). For example, one or more primer sequences with sequence complementarity to one or more RNAs or cDNAs of interest can be used to amplify the one or more RNAs or cDNAs of interest, thereby selectively enriching these RNAs or cDNAs.

In some aspects, when two or more analytes are analyzed, a first and second probe that is specific for (e.g., specifically hybridizes to) each RNA or cDNA analyte are used. For example, in some embodiments of the methods provided herein, templated ligation is used to detect gene expression in a biological sample. An analyte of interest (such as a protein), bound by a labelling agent or binding agent (e.g., an antibody or epitope binding fragment thereof), wherein the binding agent is conjugated or otherwise associated with a reporter oligonucleotide comprising a reporter sequence that identifies the binding agent, can be targeted for analysis. Probes may be hybridized to the reporter oligonucleotide and ligated in a templated ligation reaction to generate a product for analysis. In some embodiments, gaps between the probe oligonucleotides may first be filled prior to ligation, using, for example, Mu polymerase, DNA polymerase, RNA polymerase, reverse transcriptase, VENT polymerase, Taq polymerase, and/or any combinations, derivatives, and variants (e.g., engineered mutants) thereof. In some embodiments, the assay can further include amplification of templated ligation products (e.g., by multiplex PCR).

In some embodiments, an oligonucleotide with sequence complementarity to the complementary strand of captured RNA (e.g., cDNA) can bind to the cDNA. For example, biotinylated oligonucleotides with sequence complementary to one or more cDNA of interest binds to the cDNA and can be selected using biotinylation-strepavidin affinity using any of a variety of methods known to the field (e.g., streptavidin beads).

In some embodiments, the analytes may be further enriched for in situ readout by immobilization at a location in the biological sample. In a non-limiting example, the analytes may comprise one or more fragments that are specific to a location in the biological sample.

Alternatively, one or more species of RNA can be down-selected (e.g., removed) using any of a variety of methods. For example, probes can be administered to a sample that selectively hybridize to ribosomal RNA (rRNA), thereby reducing the pool and concentration of rRNA in the sample. Additionally and alternatively, duplex-specific nuclease (DSN) treatment can remove rRNA (see, e.g., Archer, et al, Selective and flexible depletion of problematic sequences from RNA-seq libraries at the cDNA stage, *BMC Genomics*, 15 401, (2014), the entire contents of which are incorporated herein by reference). Furthermore, hydroxyapatite chromatography can remove abundant species (e.g., rRNA) (see, e.g., Vandernoot, V.A., cDNA normalization by hydroxyapatite chromatography to enrich transcriptome diversity in RNA-seq applications, *Biotechniques*, 53(6) 373-80, (2012), the entire contents of which are incorporated herein by reference).

A biological sample may comprise one or a plurality of analytes of interest. Methods for performing multiplexed assays to analyze two or more different analytes in a single biological sample are provided.

VIII. Compositions, Kits, and Systems

Provided herein are kits, for example comprising one or more oligonucleotides, e.g., any described in Sections I-VI, and instructions for performing the methods provided herein. In some embodiments, the kits further comprise one or more reagents for performing the methods provided herein (e.g., one or more modified nucleotides, a library of gapfill oligonucleotides, etc.). In some embodiments, the kits further comprise one or more reagents required for one or more steps comprising hybridization, ligation, extension, amplification, detection, and/or sample preparation as described herein. In some embodiments, the kit further comprises any detectable probes and detectably labeled oligonucleotides, e.g., as described in Sections VI. In some embodiments, any or all of the oligonucleotides are DNA molecules. In some embodiments, the kit further comprises an enzyme such as a ligase and/or a polymerase described herein. In some embodiments, the ligase has DNA-splinted DNA ligase activity. In some embodiments, the kit comprises a polymerase, for instance for performing extension of the primers to incorporate modified nucleotides into cDNA products of antigen receptor transcripts. In some embodiments, the kits may contain reagents for forming a functionalized matrix (e.g., a hydrogel), such as any suitable functional moieties. In some examples, also provided are buffers and reagents for tethering the modified primers, cDNA products, and/or RCA products to the functionalized matrix. The various components of the kit may be present in separate containers or certain compatible components may be pre-combined into a single container. In some embodiments, the kits further contain instructions for using the components of the kit to practice the provided methods.

In some embodiments, the kits can contain reagents and/or consumables required for performing one or more steps of the provided methods. In some embodiments, the kits contain reagents for fixing, embedding, and/or permeabilizing the biological sample. In some embodiments, the kits contain reagents, such as enzymes and buffers for ligation and/or amplification, such as ligases and/or polymerases. In some aspects, the kit can also comprise any of the reagents described herein, e.g., wash buffer and ligation buffer. In some embodiments, the kits contain reagents for detection and/or sequencing, such as detectably labeled oligonucleotides or detectable labels. In some embodiments, the kits optionally contain other components, for example nucleic acid primers, enzymes and reagents, buffers, nucleotides, modified nucleotides, reagents for additional assays.

IX. Applications

In some aspects, the provided embodiments can be applied in an in situ method of analyzing nucleic acid sequences of V(D)J transcripts, such as an in situ immuno-profiling of VDJ sequences, for example from intact tissues or samples in which the spatial information has been preserved. In some aspects, the embodiments can be applied in an imaging or detection method for multiplexed nucleic acid analysis. In some aspects, the provided embodiments can be used to identify or detect V(D)J transcripts comprising a particular sequence of interest, for example, sequences that encode CDR3 sequences in a TCR or BCR/antibody. In some aspects, the provided embodiments can be used to crosslink the cDNA, the circularizable probe or probe set, or the RCA products via modified nucleotides, e.g., to a matrix, to increase the stability of the cDNA, the circularizable probe or probe set, or the RCA products in situ.

In some aspects, the embodiments can be applied in investigative and/or diagnostic applications, for example, for characterization or assessment of particular cell or a tissue from a subject. Applications of the provided method can comprise biomedical research and clinical diagnostics. For example, in biomedical research, applications comprise, but are not limited to, spatially resolved gene expression analysis for biological investigation or drug screening. In clinical diagnostics, applications comprise, but are not limited to, detecting gene markers such as disease, immune responses, bacterial or viral DNA/RNA for patient samples. In some aspects, the embodiments can be applied to visualize the distribution of genetically encoded markers in whole tissue at subcellular resolution.

X. Terminology

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

The terms "polynucleotide," "polynucleotide," and "nucleic acid molecule", used interchangeably herein, refer to polymeric forms of nucleotides of any length, either ribonucleotides or deoxyribonucleotides. Thus, this term comprises, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups.

"Hybridization" as used herein may refer to the process in which two single-stranded polynucleotides bind non-covalently to form a stable double-stranded polynucleotide. In one aspect, the resulting double-stranded polynucleotide can be a "hybrid" or "duplex." "Hybridization conditions" typically include salt concentrations of approximately less than 1 M, often less than about 500 mM and may be less than about 200 mM. A "hybridization buffer" includes a buffered salt solution such as 5% SSPE, or other such buffers can be used. Hybridization temperatures can be as low as 5° C., but are typically greater than 22° C., and more typically greater than about 30° C., and typically in excess of 37° C. Hybridizations are often performed under stringent conditions, i.e., conditions under which a sequence will hybridize to its target sequence but will not hybridize to other, non-complementary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the $T_m$ for the specific sequence at a defined ionic strength and pH. The melting temperature $T_m$ can be the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation, $T_m=81.5+0.41$ (% G+C), when a nucleic acid is in aqueous solution at 1 M NaCl (see e.g., Anderson and Young, Quantitative Filter Hybridization, in *Nucleic Acid Hybridization* (1985), the content of which is herein incorporated by reference in its entirety). Other references (e.g., Allawi and SantaLucia, Jr., Biochemistry, 36:10581-94 (1997), the entire content of which is herein incorporated by reference in its entirety) include alternative methods of computation which take structural and environmental, as well as sequence characteristics into account for the calculation of $T_m$.

In general, the stability of a hybrid is a function of the ion concentration and temperature. Typically, a hybridization reaction is performed under conditions of lower stringency, followed by washes of varying, but higher, stringency. Exemplary stringent conditions include a salt concentration of at least 0.01 M to no more than 1 M sodium ion concentration (or other salt) at a pH of about 7.0 to about 8.3 and a temperature of at least 25° C. For example, conditions of 5×SSPE (750 mM NaCl, 50 mM sodium phosphate, 5 mM EDTA at pH 7.4) and a temperature of approximately 30° C. are suitable for allele-specific hybridizations, though a suitable temperature depends on the length and/or GC content of the region hybridized. In one aspect, "stringency of hybridization" in determining percentage mismatch can be as follows: 1) high stringency: 0.1×SSPE, 0.1% SDS, 65° C.; 2) medium stringency: 0.2×SSPE, 0.1% SDS, 50° C. (also referred to as moderate stringency); and 3) low stringency: 1.0×SSPE, 0.1% SDS, 50° C. It is understood that equivalent stringencies may be achieved using alternative buffers, salts and temperatures. For example, moderately stringent hybridization can refer to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions can be conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C. Low stringency hybridization can refer to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M EDTA. Other suitable moderate stringency and high stringency hybridization buffers and conditions are well known to those of skill in the art and are described, for example, in Sambrook et al., Molecular Cloning: A Laboratory Manual, 2nd ed., Cold Spring Harbor Press, Plainview, N.Y. (1989); and Ausubel et al., Short Protocols in Molecular Biology, 4th ed., John Wiley & Sons (1999).

Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See M. Kanehisa, Nucleic Acids Res. 12:203 (1984).

A "primer" used herein can be an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers usually are extended by a DNA polymerase.

"Ligation" may refer to the formation of a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide.

"Sequencing," "sequence determination" and the like means determination of information relating to the nucleotide base sequence of a nucleic acid. Such information may include the identification or determination of partial as well as full sequence information of the nucleic acid. Sequence information may be determined with varying degrees of statistical reliability or confidence. In one aspect, the term includes the determination of the identity and ordering of a plurality of contiguous nucleotides in a nucleic acid. "High throughput digital sequencing" or "next generation sequencing" means sequence determination using methods that determine many (typically thousands to billions) of nucleic acid sequences in an intrinsically parallel manner, i.e. where DNA templates are prepared for sequencing not one at a time, but in a bulk process, and where many sequences are read out preferably in parallel, or alternatively using an ultra-high throughput serial process that itself may be parallelized. Such methods include but are not limited to pyrosequencing (for example, as commercialized by 454 Life Sciences, Inc., Branford, Conn.); sequencing by ligation (for example, as commercialized in the SOLiD™ technology, Life Technologies, Inc., Carlsbad, Calif.); sequencing by synthesis using modified nucleotides (such as commercialized in TruSeq™ and HiSeq™ technology by Illumina, Inc., San Diego, Calif; HeliScope™ by Helicos Biosciences Corporation, Cambridge, Ma.; and PacBio RS by Pacific Biosciences of California, Inc., Menlo Park, Calif), sequencing by ion detection technologies (such as Ion Torrent™ technology, Life Technologies, Carlsbad, Calif); sequencing of DNA nanoballs (Complete Genomics, Inc., Mountain View, Calif.); nanopore-based sequencing technologies (for example, as developed by Oxford Nanopore Technologies, LTD, Oxford, UK), and like highly parallelized sequencing methods. "Multiplexing" or "multiplex assay" herein may refer to an assay or other analytical method in which the presence and/or amount of multiple targets, e.g., multiple nucleic acid target sequences, can be assayed simultaneously by using more than one probes, each of which has at least one different detection characteristic, e.g., fluorescence characteristic (for example excitation wavelength, emission wavelength, emission intensity, FWHM (full width at half maximum peak height), or fluorescence lifetime) or a unique nucleic acid or protein sequence characteristic.

"Fluorescent label" as used herein may comprise a signaling moiety that conveys information through the fluorescent absorption and/or emission properties of one or more molecules. Exemplary fluorescent properties comprise fluorescence intensity, fluorescence lifetime, emission spectrum characteristics and energy transfer.

The term "about" as used herein refers to the usual error range for the respective value readily known to the skilled person in this technical field. Reference to "about" a value or parameter herein comprises (and describes) embodiments that are directed to that value or parameter per se.

As used herein, the singular forms "a," "an," and "the" comprise plural referents unless the context clearly dictates otherwise. For example, "a" or "an" means "at least one" or "one or more."

Throughout the present disclosure, various aspects are presented in a range format. It should be understood that the description in range format is merely for convenience and brevity and should not be construed as an inflexible limitation on the scope of the present disclosure. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the present disclosure. The upper and lower limits of these smaller ranges may independently be comprised in the smaller ranges, and are also encompassed within the present disclosure, subject to any specifically excluded limit in the stated range. Where the stated range comprises one or both of the limits, ranges excluding either or both of those comprised limits are also comprised in the present disclosure. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

EXAMPLE

The following examples are included for illustrative purposes only and are not intended to limit the scope of the present disclosure.

Example 1: Enriching and Detecting V(D)J Sequences In Situ

A tissue sample is obtained and sectioned (e.g., cryosectioned) onto a glass slide for processing. Thin sections, e.g., with a thickness of 10 µm, are cut with a cryostat and collected on glass slides. Sections are fixed (e.g., by incubating in 3.7% paraformaldehyde (PFA)), washed, and permeabilized. After permeabilization, sections are washed, and dehydrated, e.g., using an escalating ethanol series. Secure seal chambers are mounted on the slides to cover the tissue sections, and the sections are hydrated by a brief wash. To prepare for primer and probe hybridization, a buffer is added to the tissue section.

Enrichment of V(D)J sequences in situ may be achieved by using several primers targeting the constant region that bind along the transcript and then using a reverse transcriptase with a strong strand displacement function to displace the cDNA molecules. Alternatively, a helicase can be used together with a reverse transcriptase. The cDNA molecules can be cross-linked to prevent them from diffusing away; circularizable probes may then be used for in situ analysis. In some embodiments during reverse transcription, modified nucleotides may be incorporated at low ratio (1-10%) with crosslinking moieties that could be cross-linked. High molecular weight PEG molecules may be crosslinked to the extension products which makes diffusion much slower and sterically hindered.

Circularizable probe hybridized to the cDNA molecules can be circularized using gapfill polymerization or gapfill oligonucleotide ligation, thereby incorporating sequence information of the V(D)J join in the cDNA molecules (e.g., the sequences that encode CDR3 sequences of TCRs or antibodies) into the circularized probe.

After primer extension or gapfill oligonucleotide hybridization, sections can be immersed in a ligation mixture containing buffer, BSA, RNAse inhibitor, and T4 DNA ligase, in order to ligate the circularizable probe. Ligation is optionally performed for 60 minutes at 37° C. After ligation, the sections are optionally washed.

For rolling circle amplification (RCA), the sections are immersed in an RCA mixture containing phi29 polymerase buffer, dNTPs, BSA, phi29 polymerase, glycerol, and the RCA primer. RCA is optionally performed for about 30 minutes, about one hour, about two hours, or about three hours at 37° C. After RCA, the sections are optionally washed.

Detection of sequences of the RCA product can be performed using sequencing by synthesis (SBS), sequencing by ligation (SBL), sequencing by binding (SBB), or sequential hybridization of detectable probes. Multiple cycles of contacting the sample with nucleotide mixes or probes and sequence determination can be performed. Fluorescent images can be obtained in each cycle, and one or more wash steps can be performed in a cycle or between cycles.

Example 2: Direct RNA Detection of V(D)J Transcript Sequences In Situ

A tissue sample is obtained and sectioned (e.g., cryosectioned) onto a glass slide and processed essentially as described in Example 1. V(D)J transcripts in the sample are analyzed using circularizable probes that hybridize to the mDNA molecules at regions that flank the V(D)J join. In some cases, a circularizable probe hybridizes to a region in the V segment and a region in the J segment which are less variable than the V(D)J join, and the circularizable probe can be circularized using gapfill polymerization (e.g., using a reverse transcriptase) or gapfill oligonucleotide ligation using the mRNA as a ligation template, thereby incorporating sequence information of the V(D)J join (e.g., the sequences that encode CDR3 sequences of TCRs or antibodies) into the circularized probe. A polymerase with no or limited strand displacement activity (e.g., those disclosed in Martin-Alonso et al., *ACS Infect. Dis.* 2020, 6, 5, 1140-1153) can be used to perform gapfill polymerization using the mRNA as a template.

After primer extension or gapfill oligonucleotide hybridization, sections can be immersed in a ligation mixture containing buffer, BSA, RNAse inhibitor, and an RNA-templated ligase, in order to ligate the circularizable probe. The circularizable probe (prior to or after extension by gapfill polymerization) and/or the gapfill oligonucleotide can comprise one or more ribonucleotides at or near a ligation junction (e.g., within 5 nucleotides from the ligation junction). Ligation is optionally performed for 60 minutes at 37° C. After ligation, the sections are optionally washed.

For rolling circle amplification (RCA), the sections are immersed in an RCA mixture containing phi29 polymerase buffer, dNTPs, BSA, phi29 polymerase, glycerol, and the RCA primer. RCA is optionally performed for about 30 minutes, about one hour, about two hours, or about three hours at 37° C. After RCA, the sections are optionally washed.

Detection of sequences of the RCA product can be performed using sequencing by synthesis (SBS), sequencing by ligation (SBL), sequencing by binding (SBB), or sequential hybridization of detectable probes. Multiple cycles of contacting the sample with nucleotide mixes or probes and sequence determination can be performed. Fluorescent images can be obtained in each cycle, and one or more wash steps can be performed in a cycle or between cycles.

The present disclosure is not intended to be limited in scope to the particular disclosed embodiments, which are provided, for example, to illustrate various aspects of the disclosure. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method for analyzing a biological sample, comprising:
(a) generating a plurality of nucleic acid molecules using a plurality of primers, wherein the generation comprises reverse transcribing an antigen receptor transcript at a location in the biological sample using a polymerase having strand displacement activity, wherein the plurality of primers specifically target different sequences of the antigen receptor transcript;
(b) immobilizing at least a nucleic acid molecule of the plurality of nucleic acid molecules at the location, wherein the nucleic acid molecule comprises a V (D) J join comprising a V (variable) segment, a J (joint) segment, and optionally a D (diversity) segment between the V and J segments;
(c) circularizing the nucleic acid molecule or a circularizable probe or probe set hybridized to the nucleic acid molecule to generate a circularized molecule;
(d) generating a rolling circle amplification (RCA) product of the circularized molecule; and
(e) detecting a signal associated with the RCA product, thereby detecting the antigen receptor transcript or a sequence thereof at the location in the biological sample.

2. The method of claim 1, wherein the nucleic acid molecule of the plurality of nucleic acid molecules comprises a complementary deoxyribonucleic acid (cDNA) sequence complementary to a sequence of the antigen receptor transcript.

3. The method of claim 1, wherein the antigen receptor transcript is reverse transcribed in the presence of a helicase having strand displacement activity.

4. The method of claim 1, wherein one or more primers of the plurality of primers comprise a 5' overhang upon hybridization to the antigen receptor transcript.

5. The method of claim 1, wherein the antigen receptor transcript is reverse transcribed using at least two primers of the plurality of primers that hybidize to adjacent sequences in a C (constant) region in the antigen receptor transcript.

6. The method of claim 5, wherein the adjacent sequences are non-overlapping with one another, and extension of a particular 5' primer displaces an extension product of one or more 3' primers hybridized to the antigen receptor transcript.

7. The method of claim 6, wherein the extension product is linked to one or more molecules at the location in the biological sample.

8. The method of claim 1, wherein the biological sample is contacted with the circularizable probe or probe set, wherein the circularizable probe or probe set comprises a barcode region comprising one or more barcode sequences, and the circularizable probe or probe set is ligated using the nucleic acid molecule as a template to generate the circularized molecule.

9. The method of claim 8, wherein the circularizable probe or probe set comprises: a 3' region that hybridizes to a sequence in, or 3' to, the V segment of the nucleic acid molecule; and a 5' region that hybridizes to a sequence in, or 5' to, the J segment of the nucleic acid molecule.

10. The method of claim 9, comprising using a polymerase to extend the 3' region using the nucleic acid molecule as a template to generate an extended 3' region, and using template-dependent ligation to ligate the extended 3' region to the 5' region, thereby filling a gap between the 3' region and the 5' region hybridized to the nucleic acid molecule.

11. The method of claim 9, comprising hybridizing an oligonucleotide comprising a 5' end and a 3' end to the nucleic acid molecule between the 3' region and the 5' region of the circularizable probe or probe set, and using a ligase to ligate the 3' region and the 5' region to the 5' end and the 3' end, respectively, of the oligonucleotide, thereby filling a gap between the 3' region and the 5' region hybridized to the nucleic acid molecule.

12. The method of claim 11, wherein the oligonucleotide comprises a sequence complementary to the V (D) J join or a portion thereof.

13. The method of claim 1, wherein the nucleic acid molecule is ligated to generate the circularized molecule.

14. The method of claim 1, wherein the circularized molecule comprises the D segment or a complement thereof.

15. The method of claim 1, wherein the RCA product is generated in situ in the biological sample or a matrix embedding the biological sample.

16. The method of claim 1, wherein the method comprises imaging the biological sample to detect the RCA product in situ in the biological sample or a matrix embedding the biological sample.

17. The method of claim 1, wherein the method comprises detecting the RCA product using sequential hybridization of detectable probes, sequencing by hybridization, sequencing by ligation, sequencing by synthesis, sequencing by binding, or a combination thereof.

18. The method of claim 1, wherein the RCA product comprises multiple copies of a unit sequence comprising a sequence of the V(D)J join, wherein a sequence of the V(D)J join in the unit sequence is assigned a signal code sequence, and detecting the sequence of the V(D)J join comprises:

(i) contacting the biological sample with a first detectable probe and a first detectably labeled oligonucleotide to generate a first complex comprising the first detectable probe hybridized to the unit sequence of the RCA product and the first detectably labeled oligonucleotide hybridized to the first detectable probe, wherein the first detectable probe comprises: a recognition sequence complementary to the unit sequence, and a first overhang sequence, and wherein the first detectably labeled oligonucleotide comprises: a sequence complementary to the first overhang sequence, and a first optically detectable moiety;

(ii) imaging the biological sample to detect a first signal from the first optically detectable moiety, wherein the first signal corresponds to a first signal code in the signal code sequence;

(iii) contacting the biological sample with a second detectable probe and a second detectably labeled oligonucleotide to generate a second complex comprising the second detectable probe hybridized to the unit sequence of the RCA product and the second detectably labeled oligonucleotide hybridized to the second detectable probe, wherein the second detectable probe comprises: a recognition sequence complementary to the unit sequence, and a second overhang sequence, and wherein the second detectably labeled oligonucleotide comprises: a sequence complementary to the second overhang sequence, and a second optically detectable moiety; and (iv) imaging the biological sample to detect a second signal from the second optically detectable moiety, wherein the second signal corresponds to a second signal code in the signal code sequence, wherein the signal code sequence comprising at least the first signal code and the second signal code is determined at a location in the biological sample, thereby detecting the sequence of the V(D)J join in the unit sequence and detecting the corresponding antigen receptor transcript at the location in the biological sample.

19. The method of claim 1, wherein the biological sample is a tissue section.

20. The method of claim 1, wherein the method comprises detecting the RCA product using sequencing by synthesis.

* * * * *